(12) United States Patent
Sareen et al.

(10) Patent No.: US 7,560,229 B2
(45) Date of Patent: Jul. 14, 2009

(54) METHODS OF USE OF THE ENZYMES OF MYCOTHIOL SYNTHESIS

(75) Inventors: Dipti Sareen, Bhopal (IN); Gerald L. Newton, San Diego, CA (US); Robert C. Fahey, Del Mar, CA (US); Nancy Buchmeier, Encinitas, CA (US); Micah Steffek, Simi Valley, CA (US); Yoseff Av-Gay, Vancouver (CA); Mamta Rawat, Fresno, CA (US); Teresa Koledin, San Diego, CA (US)

(73) Assignees: The Regents of the University of California, Oakland, CA (US); University of British Columbia, Vancouver (CA)

( * ) Notice: Subject to any disclaimer, the term of this patent is extended or adjusted under 35 U.S.C. 154(b) by 293 days.

(21) Appl. No.: 10/511,244

(22) PCT Filed: Apr. 15, 2003

(86) PCT No.: PCT/US03/11539

§ 371 (c)(1),
(2), (4) Date: Sep. 29, 2005

(87) PCT Pub. No.: WO03/089585

PCT Pub. Date: Oct. 30, 2003

(65) Prior Publication Data

US 2006/0183116 A1    Aug. 17, 2006

Related U.S. Application Data

(60) Provisional application No. 60/373,079, filed on Apr. 15, 2002, provisional application No. 60/373,890, filed on Apr. 19, 2002.

(51) Int. Cl.
| | |
|---|---|
| *C12Q 1/68* | (2006.01) |
| *A61K 49/00* | (2006.01) |
| *C12P 19/34* | (2006.01) |
| *G01N 33/566* | (2006.01) |
| *A01N 61/00* | (2006.01) |

(52) U.S. Cl. .............................. 435/6; 424/9.1; 424/9.2; 435/91.31; 435/375; 436/501; 514/1; 514/2; 536/24.5

(58) Field of Classification Search ................ 435/6, 435/91.1, 455, 375, 91.31; 514/1, 2, 44; 424/9.1, 9.2; 536/23.1, 23.2, 24.5; 436/501
See application file for complete search history.

(56) References Cited

OTHER PUBLICATIONS

Bornemann, C. et al., Biochem. J., vol. 325, pp. 623-629 (1997).*
Sareen et al., "Mycothiol is essential for growth of tuberculosis", *Journal of Bacteriology*, vol. 185(22), pp. 6736-6740, (2003).
Rawat et al., "Mycothiol-deficient Mycobacterium smegmatis mutants are hypersensitive to alkylating agents, free radicals, and antibiotics", *Antimicrobial Agents and Chemotherapy*, vol. 46(11) pp. 3348-3355, (2002).

* cited by examiner

*Primary Examiner*—Jane Zara
(74) *Attorney, Agent, or Firm*—DLA Piper LLP (US)

(57) ABSTRACT

The present invention utilizes three families of bacterial enzymes, which play a key role in mycothiol biosynthesis. The three families are bacterial cysteine:glucosaminyl inositol ligases (MshC) with catalytic ligase activity for ligation of glucosaminyl inositol and cysteine, bacterial acetyl-CoA: Cys-GlcN-Ins acetyltransferases (MshD) with catalytic activity for addition of an acetyl group to Cys-GlcN-Ins and bacterial MshA glycosyltransferase with catalytic activity for production of GlcNAc-Ins. The invention provides methods for using the mycothiol biosynthesis ligases, acetyltransferases or glycosyltransferases in drug screening assays to determine compounds that inhibit activity. The invention provides for treatment of actinomycete infections in mammals using antibiotics that inhibit production or activity of the enzymes of mycothiol biosynthesis, in particular MshC, MshD or MshA, and thereby reduce the production of mycothiol and the virulence of the infecting bacteria. Additionally, the invention provides a live mutant with a genome containing a modification in an endogenous enzyme of mycothiol biosynthesis gene. The invention also provides an expression vector comprising polynucleotides of mshA, mshB, mshC and mshD.

8 Claims, 30 Drawing Sheets

MshC nucleic acid sequence of *M. smegmatis*

ATGCAATCGTGGTCGGCACCGGCGATTCCGGTGGTTCCGGGACGTGGCCCTGCGCTG
CGCCTCTTCGACAGCGCTGATCGCCAGGTCCGGCCCGTCACACCGGGACCGACCGC
AACCATGTACGTGTGCGGCATCACCCCATACGACGCGACCCATCTGGGTCACGCCGC
GACCTATCTGACGTTCGACCTGGTGCATCGCCTATGGCTCGACGCCGGACACACCGT
GCAGTACGTCCAGAACGTCACCGACGTGGACGACCCGTTGTTCGAGCGTGCTGAGC
GCGACGGCATCGACTGGCGGACGCTGGGCGACCGCGAGACGCAGCTGTTCCGTGAG
GACATGGCCGCGTTGCGCGTGCTGCCCCCGCACGACTACGTCGCCGCGACCGACGC
GATCGCCGAGGTCGTCGAGATGGTCGAGAAGCTGCTGGCCTCGGGTGCGGCGTACA
TCGTCGAGGACGCCGAGTACCCCGACGTGTACTTCCGCGCCGACGCCACCGCGCAG
TTCGGGTACGAGTCCGGCTACGACCGCGACACCATGCTCACGTTGTTCGCCGAACGC
GGCGGGGACCCGGACCGCCCGGGCAAGTCCGATCAACTCGACGCGTTGCTGTGGCG
CGCCGAGCGTCCTGGCGAGCCCAGCTGGCCTTCGCCGTTCGGCCGGGGCCGGCCCG
GCTGGCACGTGGAATGTTCGGCGATCGCCCTGACGCGGATCGGCACCGGCCTCGAC
ATCCAGGGCGGCGGCAGCGACCTCATCTTCCCGCACCACGAGTATTCGGCCGCGCA
CGCCGAATCCGTCACCGGTGAGCGACGATTCGCACGCCACTACGTGCACACCGGCA
TGATCGGCTGGGACGGCCACAAGATGAGCAAGAGCCGCGGCAACCTGGTCCTGGTG
TCGCAGTTGCGCGCCCAGGGCGTCGACCCGTCGGCGATCCGGCTCGGCCTGTTCTCC
GGGCACTACCGCGAGGACCGGTTCTGGAGCAACGAGGTTCTCGACGAGGCCAACGC
GCGACTCGCGCGGTGGCGCAGTGCCACCGCATTGCCCGAGGCGCCCGATGCGACCG
ACGTGATCGCGCGCGTCCGGCAGTACCTGGCCGATGACCTGGACACGCCGAAAGCG
CTTGCCGCACTCGATGGTTGGTGTACCGACGCGCTGTCCTACGGTGGGCACGACACC
GAGTCGCCGCGGCTCGTGGCCACCACCGTCGACGCGTTGCTGGGTGTGGACCTC

Figure 2A

MshC amino acid sequence of *M. smegmatis* (PMshCMs)

MQSWSAPAIP VVPGRGPALR LFDSADRQVR PVTPGPTATM
YVCGITPYDA THLGHAATYL TFDLVHRLWL DAGHTVQYVQ
NVTDVDDPLF ERAERDGIDW RTLGDRETQL FREDMAALRV
LPPHDYVAAT DAIAEVVEMV EKLLASGAAY IVEDAEYPDV
YFRADATAQF GYESGYDRDT MLTLFAERGG DPDRPGKSDQ
LDALLWRAER PGEPSWPSPF GRGRPGWHVE CSAIALTRIG
TGLDIQGGGS DLIFPHHEYS AAHAESVTGE RRFARHYVHT
GMIGWDGHKM SKSRGNLVLV SQLRAQGVDP SAIRLGLFSG
HYREDRFWSN EVLDEANARL ARWRSATALP EAPDATDVIA
RVRQYLADDL DTPKALAALD GWCTDALSYG GHDTESPRLV
ATTVDALLGV DL (SEQ ID NO: 2)

Figure 2B

>cysS2: 1242 bp - M. tuberculosis - atgcagtcgtggtattgcccaccggttccggtgttgccgggacgaggcccgcagctacgg
ctgtacgacagcgccgaccggcaggtccgtccggtggcgcccggatctaaggccaccatg
tacgtctgcgggatcacgccctacgacgccacgcatctgggccatgctgccacctatgtg
acgttcgacctgatccatcggctgtggctggatctcggtcatgaattgcactatgtccag
aacatcaccgacatcgacgatccactatttgagcgcgcggatcgcgacggtgtcgactgg
cgtgaccttgcccaagccgaggtcgccctgttctgtgaggacatggcggcgctgcgggtg
ctaccaccgcaagactacgtgggggccaccgaagcgattgctgaaatggtcgagctcatc
gaaaaaatgctggcgtgcgggggcggcctatgtcatagaccgggaaatgggagagtaccag
gacatctacttccgcgctgacgccaccctgcagttcggctacgagtcagggtatgaccgt
gacaccatgctgcggctgtgcgaggaacgtggcggcgatccgcggcgccccggcaagagc
gacgaactcgacgcgttgttgtggcgggccgcgcggcccggtgagcccagctggccgtcc
ccgttcgggcctggccggccaggctggcatgtcgagtgcgcagccatcgcgctcagtcgt
atcggaagcggcctcgacatccagggcggtggtagcgatctgatctttccgcaccacgag
ttcaccgctgcgcacgccgaatgtgtcagcggcgaacggcgattcgcgcggcactacgtg
catgccgggatgatcggctgggacgggcacaagatgtcaaagagccgcggcaacctcgtg
ctggtgtcggcgctgcgtgcgcaggacgttgagccatcggcggttcggctgggtttgctc
gccggacactaccgagccgatcggttctggagccagcaggtgcttgacgaggcgaccgcc
cggctgcaccgttggcgcaccgcaaccgcacttcccgccggtccggccgcagttgacgtt
gtcgctcgggtgcgccgctacctggccgacgatctcgatacgcccaaagcgattgccgca
ctggatggttgggtcaccgatgcggtggagtacggcggccacgatgccggggcgccgaag
ttggtggcgacggcgatcgatgccctgctcggggtggacctg

Figure 2C

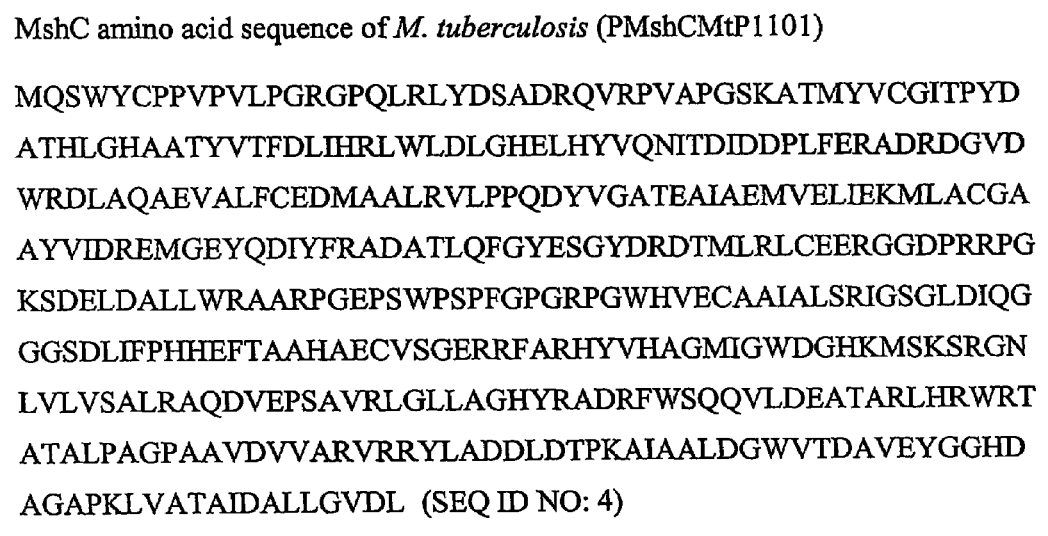

MshC amino acid sequence of *M. tuberculosis* (PMshCMtP1101)

MQSWYCPPVPVLPGRGPQLRLYDSADRQVRPVAPGSKATMYVCGITPYD
ATHLGHAATYVTFDLIHRLWLDLGHELHYVQNITDIDDPLFERADRDGVD
WRDLAQAEVALFCEDMAALRVLPPQDYVGATEAIAEMVELIEKMLACGA
AYVIDREMGEYQDIYFRADATLQFGYESGYDRDTMLRLCEERGGDPRRPG
KSDELDALLWRAARPGEPSWPSPFGPGRPGWHVECAAIALSRIGSGLDIQG
GGSDLIFPHHEFTAAHAECVSGERRFARHYVHAGMIGWDGHKMSKSRGN
LVLVSALRAQDVEPSAVRLGLLAGHYRADRFWSQQVLDEATARLHRWRT
ATALPAGPAAVDVVARVRRYLADDLDTPKAIAALDGWVTDAVEYGGHD
AGAPKLVATAIDALLGVDL (SEQ ID NO: 4)

Figure 2D

MshC amino acid sequence of *Corynebacterium striatum* (AAG03366) (PMshC-Cor.s-GB)

MHAWPDPSVPAVAGTPVPLKLFDTADQRVKEVDTTPDANGEVGMYVCGI
TPYDSTHLGHAATYLTFDLAQRQLLANGHKVHYVQNITDVDDPLFERAER
DGVDWRELGTSQINLFRSDMEILSVIPPCDYIGAMESVDEVIAMVQQLLDA
GAAYELDQGDIYASIDATEQFGYESNLDRATMEEYFAERGGDPDREGKRD
PLDALVWRGHREGEPAWDSPFGPGRPGWHVECSAIATNRLGSHFAIQGGG
SDLAFPHHEFSAAHAEAALKVERMAGHYVHAGMIALDGVKMSKSLGNL
VFVHKLSEAGHDPSAIRLAVFAGHYREDRDFSDAILAEAEERLTRWREQL
AGEVSEAEATEVVDKLRAILADDLNTPEALSLLDGAAGDCNQIIATALDGL
LGVRI (SEQ ID NO: 5)

Figure 2E

MshC amino acid sequence of *Streptomyces coelicolor* A3(2) (CAC36366) (PMshCScGB1101)

MHAWPASEVPALPGQGRDLRIHDTATGGPVTLDPGPVARIYVCGITPYD
ATHMGHAATYNAFDLVQRVWLDTKRQVHYVQNVTDVDDPLLERAVR
DGVDWTALAEQETALFREDMTALRMLPPQHYIGAVEAIPGIVPLVERLR
DAGAAYELEGDVYFSVEADPHFGGVSHLDAATMRLLSAERGGDPDRP
GKKNPLDPMLWMAAREGEPSWDGGTLGRGRPGWHIECVAIALDHLGM
GFDVQGGGSDLAFPHHEMGASHAQALTGEFPMAKAYVHAGMVGLDG
EKMSKSKGNLVFVSQLRREGVDPAAIRLTLLAHHYRSDWEWTDQVLQ
DALARLDRWRAAVSRPDGPPAEALVEEIREALANDLDSPAALAAVDRW
AALQQESGGTDIGAPGVVSRAVDALLGVAL (SEQ ID NO: 6)

|  |  | 1 | 50 |
|---|---|---|---|
| M. tuberculosis | (1) | -----------VTALDWRSALTADEQRSVRALVTATTAVDGVAPVGEQV- | |
| M. smegmatis | (1) | -----------VTSTEWRTGLTGAQQAEIRALIDAATTHDGVAPVGDQV- | |
| M. leprae | (1) | -----------MVLNWRFALSADEQRLVREIISAATEFDEVSPVGEQV- | |
| S. coelicolor | (1) | MTSDDTVRPGRPRSIETLAELTPEQTDAVLALLTEAARTDGQHAVSEQGR | |
| C. diphtheriae | (1) | -----------MIETSLASASAALRDRVDEILAAATREDGCAPLSESFL | |

|  |  | 51 | 100 |
|---|---|---|---|
| M. tuberculosis | (39) | --LRELGQQRTEHLLVAGSRPGGPIIGYLNLSPPRGAGGAMAELVVHPQS | |
| M. smegmatis | (39) | --LRELGRDRITHLLTTDD---DRVVGYLNLAPAEGDDPAMAELVVHPQA | |
| M. leprae | (38) | --LRELGYDRTEHLLVTDSRPYAPIIGYLNLSSPRDAGVAMAELVVHPRE | |
| S. coelicolor | (51) | LQLRGPAREGVVHLLLTLD--GGELVGYAQLEGTDPVEPPAAELVVHPSH | |
| C. diphtheriae | (39) | NGLRR-ADDGHVHSCVMDS--HDQVVG---VAARDGDS---AEVVVDPAF | |
|  |  | ----------------------pfam00583- | |

|  |  | 101 | 150 |
|---|---|---|---|
| M. tuberculosis | (87) | RRRGIGTAMARAALAKTAGRNQFWAHGTLDPARATASALGLVGVRELIQM | |
| M. smegmatis | (84) | RRRGIGAAMARTALAEGGPGARIWAHGNIAAAQAMASSLRLVVVRELLQM | |
| M. leprae | (86) | RRRGVGAAMVRAALAKTGGRNRFWAHGTLASARATASVLGLVPVRELVQM | |
| S. coelicolor | (99) | RGQGHGRALGSALLAASGKRLRIWAHGGHSAARHLAQVLGLSLFRELRQL | |
| C. diphtheriae | (80) | RRQGYGSFLIRHVVSQGVKN--VWAHGDGAGAKAVAKALQLEQTRQLLVM | |

|  |  | 151 | 200 |
|---|---|---|---|
| M. tuberculosis | (137) | RRPL-R--DIPEFTIPD--GVVI----RTYAGTSD-DAELLRVNNAAFAG | |
| M. smegmatis | (134) | RRPL-T--DLP-P-VPDTPGVRI----ATYAGPGD-DAEILRVNNAAFSW | |
| M. leprae | (136) | QRSL-R--TIPDPMVPDQLGWWV----RTYVGTVD-DAELLRVNNAAFAG | |
| S. coelicolor | (149) | RRPL-TGLDLPEPRLEE--GVSV----RTFVPGQD-DAAWLAVNAAAFAH | |
| C. diphtheriae | (128) | AVEGDRLVESAQLQPS--GFRVLALNEAYESIPDIEQQWLRVNNNEAFEW | |

|  |  | 201 | 250 |
|---|---|---|---|
| M. tuberculosis | (177) | HPEQGGWTAVQLAERRGEAWF-DPDGLILAFGDSPRERPGRLLGFHWTKV | |
| M. smegmatis | (174) | HPEQGGWTEHEIDERRNEGWF-DPEGLFQAFD----EQTGSLLGFHWTKI | |
| M. leprae | (178) | HPEQGGWTATQLAERRSEPWF-DPAGLFLAFGDSSSNQPGKLLGFHWTKV | |
| S. coelicolor | (191) | HPEQGSLTQRDLDDRKAEPWF-DPAGFFLA------ERDGELIGFHWTKV | |
| C. diphtheriae | (176) | HPEQGGWDSARLAQARDTQWFRESDVLFLID-----TAKRTVAGFHWTKR | |

|  |  | 251 | 300 |
|---|---|---|---|
| M. tuberculosis | (226) | HPD--HPGLGEVYVLGVDPAAQRRGLGQMLTSIGIVSLARRLGGRKTLDP | |
| M. smegmatis | (219) | HD----ASLGEVYVLGVDPQAQGRGLGYTLTLIGLHHLAEKLAG-----P | |
| M. leprae | (227) | HAA--HPGLGEVYVLGVDPSAQGRGLGQMLTSIGIASLAQRLVG-----P | |
| S. coelicolor | (234) | HA---EERLGEVYVLGIRPDTQGGGLGKALTTIGLRHLEGQ--G------ | |
| C. diphtheriae | (221) | HGDLAEGADGEVYVVGLGSAYRRRGLGDLLIRMGLHHLEYEHAR------ | |
|  |  | ---------------------pfam00583------------- | |

|  |  | 301 | 343 |
|---|---|---|---|
| M. tuberculosis | (274) | AVPPAVLLYVESDNVAAVRTYQSLGFTTYSVDTAYALAGTDN- | |
| M. smegmatis | (260) | --EPTVLLYVEADNSAAVNTYRKLGFEVFSVDAAYAAN----- | |
| M. leprae | (270) | SAEPTVMLYVESDNVAAARTYERLGFTTYSVDTAYALARIDD- | |
| S. coelicolor | (273) | --LPTAMLYVDADNKAAVAVYERLGFVTHETDLMYRTET---- | |
| C. diphtheriae | (265) | --R--VILYVEGDNESARRAYDALGFHVVESHVTYSPQSSS-- | |

Figure 8

MshD amino acid sequence of *M. tuberculosis* (CAA17625.1) (Rv0819)

MTALDWRSALTADEQRSVRALVTATTAVDGVAPVGEQVLRELGQQRT
EHLLVAGSRPGGPIIGYLNLSPPRGAGGAMAELVVHPQSRRRGIGTAMA
RAALAKTAGRNQFWAHGTLDPARATASALGLVGVRELIQMRRPLRDIP
EPTIPDGVVIRTYAGTSDDAELLRVNNAAFAGHPEQGGWTAVQLAERR
GEAWFDPDGLILAFGDSPRERPGRLLGFHWTKVHPDHPGLGEVYVLGV
DPAAQRRGLGQMLTSIGIVSLARRLGGRKTLDPAVEPAVLLYVESDNVA
AVRTYQSLGFTTYSVDTAYALAGTDN (SEQ ID NO: 14)

Figure 10A

MshD amino acid sequence of *M. smegmatis* (PMshDMs-Tr)

VTSTEWRTGL TGAQQAEIRA LIDAATTHDG VAPVGDQVLR
ELGRDRTRHL LTTDDDRVVG YLNLAPAEGD DPAMAELVVH
PQARRRGIGA AMARTALAEG GPGARIWAHG NIAAAQAMAS
SLRLVVVREL LQMRRPLTDL PPVPDTPGVR IATYAGPGDD
AEILRVNNAA FSWHPEQGGW TEHEIDERRN EGWFDPEGLF
QAFDEQTGSL LGFHWTKIHD ASLGEVYVVG VDPQAQGRGL
GYTLTLIGLH HLAEKLAGPE PTVLLYVEAD NSAAVNTYRK
LGFEVFSVDA AYAAN (SEQ ID NO: 15)

Figure 10B

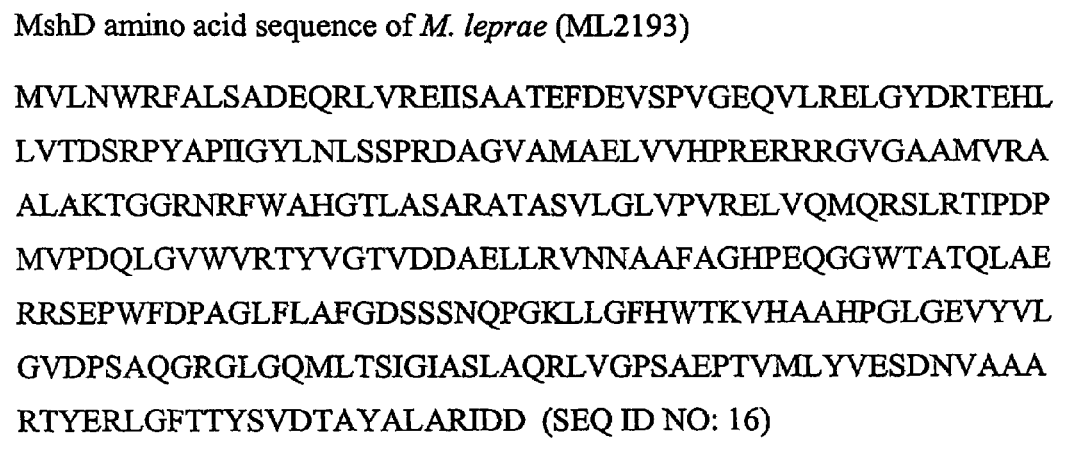

MshD amino acid sequence of *M. leprae* (ML2193)

MVLNWRFALSADEQRLVREIISAATEFDEVSPVGEQVLRELGYDRTEHL
LVTDSRPYAPIIGYLNLSSPRDAGVAMAELVVHPRERRRGVGAAMVRA
ALAKTGGRNRFWAHGTLASARATASVLGLVPVRELVQMQRSLRTIPDP
MVPDQLGVWVRTYVGTVDDAELLRVNNAAFAGHPEQGGWTATQLAE
RRSEPWFDPAGLFLAFGDSSSNQPGKLLGFHWTKVHAAHPGLGEVYVL
GVDPSAQGRGLGQMLTSIGIASLAQRLVGPSAEPTVMLYVESDNVAAA
RTYERLGFTTYSVDTAYALARIDD (SEQ ID NO: 16)

Figure 10C

MshD amino acid sequence of *Streptomyces coelicolor* (SCD84.18c, SCO4151)

MTSDDTVRPGRPRSIETLAELTPEQTDAVLALLTEAARTDGQHAVSEQG
RLQLRGPAREGVVHLLLTLDGGELVGYAQLEGTDPVEPPAAELVVHPS
HRGQGHGRALGSALLAASGKRLRIWAHGGHSAARHLAQVLGLSLFREL
RQLRRPLTGLDLPEPRLPEGVSVRTFVPGQDDAAWLAVNAAAFAHHPE
QGSLTQRDLDDRKAEPWFDPAGFFLAERDGELIGFHWTKVHAEERLGE
VYVLGIRPDTQGGGLGKALTTIGLRHLEGQGLPTAMLYVDADNKAAVA
VYERLGFVTHETDLMYRTET (SEQ ID NO: 17)

Figure 10D

MshD amino acid sequence of *Corynebacterium diphtheriae* (PMshDCd-Tr)

MIETSLASAS AALRDRVDEI LAAATREDGC APLSESFLNG
LRRADDGHVH SCVMDSHDQV VGVAARDGDS AEVVVDPAFR
RQGYGSFLIR HVVSQGVKNV WAHGDGAGAK AVAKALQLEQ
TRQLLVMAVE GDRLVESAQL QVPSGFRVLA LNEAYESIPD
IEQQWLRVNN EAFEWHPEQG GWDSARLAQA RDTQWFRESD
VLFLIDTAKR TVAGFHWTKR HGDLAEGADG EVYVVGLGSA
YRRRGLGDLL IRMGLHHLEY EHARRVILYV EGDNESARRA
YDALGFHVVE SHVTYSPQSS S (SEQ ID NO: 18)

Figure 10E

Nucleic acid sequence *mshD M. smegmatis*, including stop codon

GTGACCTCCACCGAGTGGCGCACCGGGCTCACGGGTGCCCAGCAGG
CAGAGATTCGCGCGCTGATCGACGCGGCCACCACGCACGACGGTGT
CGCGCCGGTCGGTGACCAAGTGCTGCGGGAACTGGGACGCGACCGC
ACCCGGCACCTGCTGACCACCGACGACGACCGCGTGGTCGGATACCT
CAACCTCGCGCCTGCCGAGGGGGACGATCCGGCGATGGCCGAACTC
GTCGTGCATCCGCAGGCCCGCCGGCGCGGTATCGGTGCGGCCATGGC
GCGCACCGCGCTGGCAGAGGGCGGGCCGGGCGCCCGTATCTGGGCG
CACGGCAACATCGCCGCCGCCCAGGCGATGGCGTCATCGCTTCGCCT
GGTGGTGGTGCGTGAGCTGCTGCAGATGCGCCGCCCCTGACCGATC
TGCCGCCGGTGCCGGACACCCCGGCGTGCGCATCGCGACCTACGCC
GGCCCCGGCGACGACGCCGAGATCCTGCGGGTCAACAACGCCGCGT
TCTCGTGGCACCCCGAGCAGGGCGTGA (SEQ ID NO: 48)

Figure 10F

```
                                                                                |-
MshA-Msmeg    1--------------------------------VRLATDLETPRRVAVLSVHTSPLAQPGTGDA
MshA-Mtub     1MAGVRHDDGSGLIAQRRPVRGEGATRSRGPSGPSNRNVSAADDPRRVALLAVHTSPLAQPGTGDA
SpsA-Anab     1--------------------------------------MFQNKKHRIALISVSGDPAVEIGQEEA
PimB-Mtub     1--------------------------------------------VCGVRVAIVAESFLPQVN------
              *-BOX I--|
MshA-Msmeg   32GGMNVYVLQTALQLARRGVEVEVFTRATSSADAPVVPVAPGVLVRNVVAGPFEGLDKNDLPTQLC
MshA-Mtub    66GGMNVYMLCSALHLARRGIEVEIFTRATASADPPVVRVAPGVLVRNVVAGPFEGLDKYDLPTQLC
SpsA-Anab    28GCQNVYVREVGYALAEQGWQVDMFTRRISPDQAEIVQHSPNCRTIRLQAGPVEFIGRDHVFDYLP
PimB-Mtub    19-GVSNSVVKVLEHLRRTGHEALVIAPDTPPGEDRAERLHDGVRVHRVPSRMEPKVT--TLPLGVP MshA-Msmeg   97AFTAGVLRAEATHEPGY-YDVVHSHY-WLSGQVGWLARDRWAVPLVHTAHTLAAVKNAALAAGDA
MshA-Mtub   131AFAAGVLRAEAVHEPGY-YDIVHSHY-WLSGQVGWLARDRWAVPLVHTAHTLAAVKNAALADGDG
SpsA-Anab    93EFVAEFQRFQK--RQGYNYQLIHTNY-WLSSWVGMQLKKQQPLVLVHTYHSLGAIKYQTIA--DI
PimB-Mtub    81TKR--MLRALR----GFDPDVVHLASPALLGYGGLHAARRLGVETVAVYQTDVPGFASSYG---I
                                                            G242↓   ↓D244
MshA-Msmeg  160PEPPLRAVGEQQVVDEADRLIVNTEVEAQQLVSLHNADRSRIDVVHPGVDLDVETPGSRDAARAV
MshA-Mtub   194PEPPLRTVGEQQVVDEADRLIVNTDDEARQVISLHGADPARIDVVHPGVDLDVFRPGDRRAARAA
SpsA-Anab   153PAIANQRLAIEKACLESVDTVVATSPQEQQHMRALVSKKGRIEMIPCGTDINNFGNIEKSAAREK
PimB-Mtub   137EMTARAEWAWFRHLHRLADRTLAPSTATMESLIAQGIP--RVHRWARGVDVQRFAESARNEVLRR
                                             R273↓   ↓K278
MshA-Msmeg  225EGLPTDQKIVAFVGRIQPLKAPDILLRAAAK-----LPGVRVLIAGG--PSGSGLAQPDTLVRLA
MshA-Mtub   259LGLPVDERVVAFVGRIQPLKAPDIVLRAAAK-----LPGVRIIVAGG--PSGSGLASPDGLVRLA
SpsA-Anab   218LGIEPDAKMVFYVGRFDRRKGIETLVRAVAQSRLRGEANLQLVIGGGSREGQSDGRERDRIANIV
PimB-Mtub   200RWSPDGKPIVGFVGRLAPENHVLRLTGLAAS------GAVRLVIVG-----------DGIDRAR
                                                 E354↓--------BOX II---------|
MshA-Msmeg  283DELGISDRVTFLPPQSREQLVNVYRAADLVAVPSYSESFGLVAVEAQACGTPVVAAAVGGLPVAV
MshA-Mtub   317DELGISARVTFLPPQSHTDLATLFRAADLVAVPSYSESFGLVAVEAQACGTPVVAAAVGGLPVAV
SpsA-Anab   283AELELNDCTTEAGRLDHEILPYYAAADVCVVPSHYEPFGLVAIEAMASKTPVIASNVGGLQFTV
PimB-Mtub   247LQSAMPT-AVLTGARYGKELAEAYASMDVFVHSGEHETFCQVVQEALASGLPVIAPDAGGPRDLI MshA-Msmeg  348ADGVSGALVD-GHDIGDWADTISEVLDREPA----ALSRASAEHAAQFSWAHTVDALLASYSRAM
MshA-Mtub   382RDGITGTLVS-GHEVGQWADAIDHLLRLCAGPGRVMSRAAARHAATFSWENTTDALLASYRRAI
SpsA-Anab   348VPEVTGLLAE-PQDESAFATAIDRILANPTWR-DQLGTAARQRVETTFSWAGVASQLSQLYTHLL
PimB-Mtub   311TPHRTGLLLEVEEFEHRLPDAVAHLVHERQR-----YALAARRSVLGRSWPVVCDELLGHYEAVR MshA-Msmeg  408SDYRARHPRPA--------ARRSGRRFSMRRGVRT
MshA-Mtub   446GEYNAERQRRGGEVISDLVAVGKPRHWTPRRGVGA
SpsA-Anab   411TQNAPEKKEKE--------AVAA-----------
PimB-Mtub   371GRRTTQAA---------------------------
```

Figure 11

MshA amino acid sequence of *M. smegmatis* (PMshAMs-Tr)

VRLATDLETP RRVAVLSVHT SPLAQPGTGD AGGMNVYVLQ
TALQLARRGV EVEVFTRATS SADAPVVPVA PGVLVRNVVA
GPFEGLDKND LPTQLCAFTA GVLRAEATHE PGYYDVVHSH
YWLSGQVGWL ARDRWAVPLV HTAHTLAAVK NAALAAGDAP
EPPLRAVGEQ QVVDEADRLI VNTEVEAQQL VSLHNADRSR
IDVVHPGVDL DVFTPGSRDA ARAVFGLPTD QKIVAFVGRI
QPLKAPDILL RAAAKLPGVR VLIAGGPSGS GLAQPDTLVR
LADELGISDR VTFLPPQSRE QLVNVYRAAD LVAVPSYSES
FGLVAVEAQA CGTPVVAAAV GGLPVAVADG VSGALVDGHD
IGDWADTISE VLDREPAALS RASAEHAAQF SWAHTVDALL
ASYSRAMSDY RARHPRPAAR RSGRRFSMRR GVRT (SEQ ID NO: 19)

Figure 12A

MshA amino acid sequence of *M. tuberculosis* (PMshAMtG1002)

MAGVRHDDGS GLIAQRRPVR GEGATRSRGP SGPSNRNVSA
ADDPRRVALL AVHTSPLAQP GTGDAGGMNV YMLQSALHLA
RRGIEVEIFT RATASADPPV VRVAPGVLVR NVVAGPFEGL
DKYDLPTQLC AFAAGVLRAE AVHEPGYYDI VHSHYWLSGQ
VGWLARDRWA VPLVHTAHTL AAVKNAALAD GDGPEPPLRT
VGEQQVVDEA DRLIVNTDDE ARQVISLHGA DPARIDVVHP
GVDLDVFRPG DRRAARAALG LPVDERVVAF VGRIQPLKAP
DIVLRAAAKL PGVRIIVAGG PSGSGLASPD GLVRLADELG
ISARVTFLPP QSHTDLATLF RAADLVAVPS YSESFGLVAV
EAQACGTPVV AAAVGGLPVA VRDGITGTLV SGHEVGQWAD
AIDHLLRLCA GPRGRVMSRA AARHAATFSW ENTTDALLAS
YRRAIGEYNA ERQRRGGEVI SDLVAVGKPR HWTPRRGVGA (SEQ ID
NO: 20)

Figure 12B

Nucleic acid sequence *mshA M. smegmatis*, including stop codon

GTGCGTCTAGCGACAGACCT
CGAGACCCCCGCCGCGTGGCGGTGTTGTCGGTACACACCTCTCCGC
TGGCGCAGCCGGGCACCGGCGACGCGGGCGGCATGAACGTCTACGT
GTTGCAGACCGCGCTGCAACTGGCCCGGCGTGGCGTCGAGGTCGAG
GTCTTCACCAGGGCCACGTCGTCGGCCGATGCGCCGGTCGTGCCTGT
GGCGCCCGGTGTGCTGGTGCGCAACGTCGTGGCCGGCCCGTTCGAAG
GCCTCGACAAGAACGATCTGCCCACGCAGCTGTGCGCGTTCACCGCG
GGTGTGCTGCGCGCCGAGGCGACCCACGAGCCCGGCTACTACGACG
TCGTGCATTCGCACTACTGGCTGTCCGGCCAGGTCGGGTGGCTGGCG
CGCGACCGCTGGGCCGTGCCGCTGGTGCACACCGCGCACACGCTGG
CCGCGGTCAAGAACGCCGCACTCGCCGCGGGCGACGCACCCGAGCC
GCCGCTGCGCGCGGTGGGCGAACAACAGGTGGTCGACGAGGCCGAC
CGCCTCATCGTGAACACCGAAGTCGAAGCGCAGCAACTGGTCTCGTT
GCACAATGCCGACCGCTCACGCATCGACGTCGTGCACCCCGGCGTCG
ATCTCGACGTGTTCACCCCCGGTTCGCGCGACGCGGCGCGCGCGGTG
TTCGGGCTTCCCACCGACCAGAAGATCGTGGCGTTCGTGGGCCGCAT
CCAGCCGCTCAAGGCCCCCGACATCCTGCTGCGTGCCGCGGCGAAAC
TGCCCGGCGTGCGCGTGCTGATCGCCGGTGGACCCTCCGGATCGGGA
CTTGCCCAACCGGACACGCTGGTTCGGCTCGCCGACGAACTGGGTAT
CAGTGACCGGGTGACGTTCCTCCCGCCGCAGAGCCGCGAACAACTG
GTCAACGTGTACCGGGCGGCCGATCTGGTCGCGGTGCCGAGCTACTC
CGAGTCGTTCGGCCTGGTCGCCGTCGAGGCGCAGGCGTGCGGCACGC
CCGTCGTCGCCGCGGCCGTCGGCGGACTGCCGGTCGCGGTGGCCGAC
GGCGTCAGCGGGGCACTCGTCGACGGCCACGACATCGGCGACTGGG
CCGACACCATCAGCGAGGTGCTCGACCGCGAGCCCGCCGCGCTGAG
CCGCGCCTCCGCCGAACACGCCGCTCAGTTCTCGTGGGCGCACACCG
TCGACGCGCTGCTCGCCAGCTACAGCCGGGCCAT
GAGTGACTACCGGGCCCGTCATCCCAGACCCGCCGCGCGGCGTTCCG
GACGCCGGTTCTCGATGCGCAGGGGAGTACGCACGTGA (SEQ ID NO: 49)

Figure 12C

(a) First Half of Rossman fold:

```
M.smeg MshC   ( 40) --MYVCGITPYDATHLGHAATYLTFDL ( 64)
M.lepr Mshc   ( 11) ATMYVCGITPYDATHLGHAATYLAFDL ( 37)
S.coel.MshC   ( 40) --IYVCGITPYDATHMGHAATYNAFDL ( 64)
C.strt.MshC   ( 44) --MYVCGITPYDSTHLGHAATYLTFDL ( 68)
T.bifd.MshC   ( 40) --MYVCGITPYDAAHLGHAFTYLTFDL ( 64)
M.tubr CysS   ( 30) --IYLCGATVQGLPHIGHVRSGVAFDI ( 54)
E.coli CysS   ( 25) --MYVCGITVYDLCHIGHGRTFVAFDV ( 49)
```

(b) Second half of Rossman Fold:

```
M.smeg MshC   (218) SPFGRGRPGWHVECSAIALTRIGTGLDIQGGGSDLIFPHHEYSAAHAESVT
M.lepr Mshc   (190) SPFGPGRPGWHVECAAIALSRIGIGLDIQGGGSDLIFPHHEFTAAHAECVR
S.coel.MshC   (215) GTLGRGRPGWHIECVAIALDHLGMGFDVQGGGSDLAFPHHEMGASHAQALT
C.strt.MshC   (219) SPFGPGRPGWHVECSAIATNRLGSHFAIQGGGSDLAFPHHEFSAAHAEAAL
T.bifd.MshC   (198) TPLGRGRPGWHVECSAISVHELGMGFDLNGGGDDLIFPHHEMGAAEACCAT
M.tubr CysS   (214) TPWGRGRPGWHLECSAMARSYLGPEEDIHCGGMDLVFPHHENEIAQSRAAG
E.coli CysS   (196) SPWGAGRPGWHIECSAMNCKQLGNHFDIHGGGSDLMFPHHENEIAQSTCAH M.smeg MshC   GERRFARHYVHTGMIGWDGHKMSKS (293)
M.lepr Mshc   GERRFARHYVHAGMIGWDEHKRMSKS (265)
S.coel.MshC   GEFPMAKAYVHAGMVGLDGEKMSKS (290)
C.strt.MshC   KVERMAGHYVHAGMIALDGVKMSKS (294)
T.bifd.MshC   GSRPQARHYLHVAMVGLDGEKMSKS (289)
M.tubr CysS   DG--FARYWLHNGWVTMGGEKMSKS (271)
E.coli CysS   DGQ-YVNYWMHSGMVMVDREKMSKS (270)
```

Figure 18

SEQUENCE LISTING

```
<160> NUMBER OF SEQ ID NOS: 49

<210> SEQ ID NO 1
<211> LENGTH: 1236
<212> TYPE: DNA
```

<210> SEQ ID NO 1
<400> SEQUENCE: 1

```
atgcaatcgt ggtcggcacc ggcgattccg gtggttccgg gacgtggccc tgcgctgcgc      60
ctcttcgaca gcgctgatcg ccaggtccgg cccgtcacac cgggaccgac cgcaaccatg     120
tacgtgtgcg gcatcacccc atacgacgcg acccatctgg gtcacgccgc gacctatctg     180
acgttcgacc tggtgcatcg cctatggctc gacgccggac acaccgtgca gtacgtccag     240
aacgtcaccg acgtggacga cccgttgttc gagcgtgctg agcgcgacgg catcgactgg     300
cggacgctgg gcgaccgcga gacgcagctg ttccgtgagg acatggccgc gttgcgcgtg     360
ctgcccccgc acgactacgt cgccgcgacc gacgcgatcg ccgaggtcgt cgagatggtc     420
gagaagctgc tggcctcggg tgcggcgtac atcgtcgagg acgccgagta ccccgacgtg     480
tacttccgcg ccgacgccac cgcgcagttc gggtacgagt ccggctacga ccgcgacacc     540
atgctcacgt tgttcgccga acgcggcggg gacccgacc gccgggcaa gtccgatcaa     600
ctcgacgcgt tgctgtggcg cgccgagcgt cctggcgagc cagctggcc ttcgccgttc     660
ggccgggcc ggcccggctg gcacgtggaa tgttcggcga tcgccctgac gcggatcggc     720
accggcctcg acatccaggg cggcggcagc gacctcatct cccgcacca cgagtattcg     780
gccgcgcacg ccgaatccgt caccggtgag cgacgattcg cacgccacta cgtgcacacc     840
ggcatgatcg gctgggacgg ccacaagatg agcaagagcc gcggcaacct ggtcctggtg     900
tcgcagttgc gcgcccaggg cgtcgacccg tcggcgatcc ggctcggcct gttctccggg     960
cactaccgcg aggaccggtt ctggagcaac gaggttctcg acgaggccaa cgcgcgactc    1020
gcgcggtggc gcagtgccac cgcattgccc gaggcgcccg atgcgaccga cgtgatcgcg    1080
cgcgtccggc agtacctggc cgatgacctg gacacgccga aagcgcttgc cgcactcgat    1140
ggttggtgta ccgacgcgct gtcctacggt gggcacgaca ccgagtcgcc gcggctcgtg    1200
gccaccaccg tcgacgcgtt gctgggtgtg gacctc                              1236
```

<210> SEQ ID NO 2
<211> LENGTH: 412
<212> TYPE: PRT
<213> ORGANISM: Mycobacterium smegmatis

<400> SEQUENCE: 2

```
Met Gln Ser Trp Ser Ala Pro Ala Ile Pro Val Val Pro Gly Arg Gly
1               5                   10                  15

Pro Ala Leu Arg Leu Phe Asp Ser Ala Asp Arg Gln Val Arg Pro Val
            20                  25                  30

Thr Pro Gly Pro Thr Ala Thr Met Tyr Val Cys Gly Ile Thr Pro Tyr
        35                  40                  45

Asp Ala Thr His Leu Gly His Ala Ala Thr Tyr Leu Thr Phe Asp Leu
    50                  55                  60

Val His Arg Leu Trp Leu Asp Ala Gly His Thr Val Gln Tyr Val Gln
65                  70                  75                  80

Asn Val Thr Asp Val Asp Asp Pro Leu Phe Glu Arg Ala Glu Arg Asp
                85                  90                  95

Gly Ile Asp Trp Arg Thr Leu Gly Asp Arg Glu Thr Gln Leu Phe Arg
            100                 105                 110

Glu Asp Met Ala Ala Leu Arg Val Leu Pro Pro His Asp Tyr Val Ala
        115                 120                 125

Ala Thr Asp Ala Ile Ala Glu Val Val Glu Met Val Glu Lys Leu Leu
```

-continued

```
                130                 135                 140
Ala Ser Gly Ala Ala Tyr Ile Val Glu Asp Ala Glu Tyr Pro Asp Val
145                 150                 155                 160
Tyr Phe Arg Ala Asp Ala Thr Ala Gln Phe Gly Tyr Glu Ser Gly Tyr
                165                 170                 175
Asp Arg Asp Thr Met Leu Thr Leu Phe Ala Glu Arg Gly Gly Asp Pro
            180                 185                 190
Asp Arg Pro Gly Lys Ser Asp Gln Leu Asp Ala Leu Leu Trp Arg Ala
        195                 200                 205
Glu Arg Pro Gly Glu Pro Ser Trp Pro Ser Pro Phe Gly Arg Gly Arg
    210                 215                 220
Pro Gly Trp His Val Glu Cys Ser Ala Ile Ala Leu Thr Arg Ile Gly
225                 230                 235                 240
Thr Gly Leu Asp Ile Gln Gly Gly Ser Asp Leu Ile Phe Pro His
                245                 250                 255
His Glu Tyr Ser Ala Ala His Ala Glu Ser Val Thr Gly Glu Arg Arg
            260                 265                 270
Phe Ala Arg His Tyr Val His Thr Gly Met Ile Gly Trp Asp Gly His
        275                 280                 285
Lys Met Ser Lys Ser Arg Gly Asn Leu Val Leu Val Ser Gln Leu Arg
    290                 295                 300
Ala Gln Gly Val Asp Pro Ser Ala Ile Arg Leu Gly Leu Phe Ser Gly
305                 310                 315                 320
His Tyr Arg Glu Asp Arg Phe Trp Ser Asn Glu Val Leu Asp Glu Ala
                325                 330                 335
Asn Ala Arg Leu Ala Arg Trp Arg Ser Ala Thr Ala Leu Pro Glu Ala
            340                 345                 350
Pro Asp Ala Thr Asp Val Ile Ala Arg Val Arg Gln Tyr Leu Ala Asp
        355                 360                 365
Asp Leu Asp Thr Pro Lys Ala Leu Ala Ala Leu Asp Gly Trp Cys Thr
    370                 375                 380
Asp Ala Leu Ser Tyr Gly Gly His Asp Thr Glu Ser Pro Arg Leu Val
385                 390                 395                 400
Ala Thr Thr Val Asp Ala Leu Leu Gly Val Asp Leu
                405                 410
```

<210> SEQ ID NO 3
<211> LENGTH: 1242
<212> TYPE: DNA
<213> ORGANISM: Mycobacterium tuberculosis

<400> SEQUENCE: 3

```
atgcagtcgt ggtattgccc accggttccg gtgttgccgg acgaggccc gcagctacgg      60
ctgtacgaca cgccgaccg gcaggtccgt ccggtggcgc ccggatctaa ggccaccatg     120
tacgtctgcg ggatcacgcc ctacgacgcc acgcatctgg ccatgctgc cacctatgtg     180
acgttcgacc tgatccatcg gctgtggctg atctcggtc atgaattgca ctatgtccag     240
aacatcaccg acatcgacga tccactattt gagcgcgcgg atcgcgacgg tgtcgactgg     300
cgtgaccttg cccaagccga ggtcgccct ttctgtgagg acatggcgg gctgcgggtg     360
ctaccaccgc aagactacgt gggggccacc gaagcgattg ctgaaatggt cgagctcatc     420
gaaaaaatgc tggcgtgcgg ggcggcctat gtcatagacc gggaaatggg agagtaccag     480
gacatctact tccgcgctga cgccaccctg cagttcggct acgagtcagg gtatgaccgt     540
```

-continued

```
gacaccatgc tgcggctgtg cgaggaacgt ggcggcgatc cgcggcgccc cggcaagagc      600
gacgaactcg acgcgttgtt gtggcgggcc gcgcggcccg gtgagcccag ctggccgtcc      660
ccgttcgggc ctggccggcc aggctggcat gtcgagtgcg cagccatcgc gctcagtcgt      720
atcggaagcg gcctcgacat ccaggcggt ggtagcgatc tgatcttcc gcaccacgag        780 ttcaccgctg cgcacgccga atgtgtcagc ggcgaacggc gattcgcgcg cactacgtg       840 catgccggga tgatcggctg ggacgggcac aagatgtcaa agagccgcgg caacctcgtg      900
ctggtgtcgg cgctgcgtgc gcaggacgtt gagccatcgg cggttcggct gggtttgctc     960
gccggacact accgagccga tcggttctgg agccagcagg tgcttgacga ggcgaccgcc     1020
cggctgcacc gttggcgcac cgcaaccgca cttcccgccg gtccggccgc agttgacgtt     1080
gtcgctcggg tgcgccgcta cctggccgac gatctcgata cgcccaaagc gattgccgca     1140
ctggatggtt gggtcaccga tgcggtggag tacgcggcc acgatgccgg ggcgccgaag     1200
ttggtggcga cggcgatcga tgccctgctc ggggtggacc tg                        1242
```

<210> SEQ ID NO 4
<211> LENGTH: 414
<212> TYPE: PRT
<213> ORGANISM: Mycobacterium tuberculosis

<400> SEQUENCE: 4

```
Met Gln Ser Trp Tyr Cys Pro Pro Val Pro Val Leu Pro Gly Arg Gly
1               5                   10                  15

Pro Gln Leu Arg Leu Tyr Asp Ser Ala Asp Arg Gln Val Arg Pro Val
            20                  25                  30

Ala Pro Gly Ser Lys Ala Thr Met Tyr Val Cys Gly Ile Thr Pro Tyr
        35                  40                  45

Asp Ala Thr His Leu Gly His Ala Ala Thr Tyr Val Thr Phe Asp Leu
    50                  55                  60

Ile His Arg Leu Trp Leu Asp Leu Gly His Glu Leu His Tyr Val Gln
65                  70                  75                  80

Asn Ile Thr Asp Ile Asp Asp Pro Leu Phe Glu Arg Ala Asp Arg Asp
                85                  90                  95

Gly Val Asp Trp Arg Asp Leu Ala Gln Ala Glu Val Ala Leu Phe Cys
            100                 105                 110

Glu Asp Met Ala Ala Leu Arg Val Leu Pro Pro Gln Asp Tyr Val Gly
        115                 120                 125

Ala Thr Glu Ala Ile Ala Glu Met Val Glu Leu Ile Glu Lys Met Leu
    130                 135                 140

Ala Cys Gly Ala Ala Tyr Val Ile Asp Arg Glu Met Gly Glu Tyr Gln
145                 150                 155                 160

Asp Ile Tyr Phe Arg Ala Asp Ala Thr Leu Gln Phe Gly Tyr Glu Ser
                165                 170                 175

Gly Tyr Asp Arg Asp Thr Met Leu Arg Leu Cys Glu Glu Arg Gly Gly
            180                 185                 190

Asp Pro Arg Arg Pro Gly Lys Ser Asp Glu Leu Asp Ala Leu Leu Trp
        195                 200                 205

Arg Ala Ala Arg Pro Gly Glu Pro Ser Trp Pro Ser Pro Phe Gly Pro
    210                 215                 220

Gly Arg Pro Gly Trp His Val Glu Cys Ala Ala Ile Ala Leu Ser Arg
225                 230                 235                 240

Ile Gly Ser Gly Leu Asp Ile Gln Gly Gly Gly Ser Asp Leu Ile Phe
                245                 250                 255
```

```
Pro His His Glu Phe Thr Ala Ala His Ala Glu Cys Val Ser Gly Glu
            260                 265                 270

Arg Arg Phe Ala Arg His Tyr Val His Ala Gly Met Ile Gly Trp Asp
        275                 280                 285

Gly His Lys Met Ser Lys Ser Arg Gly Asn Leu Val Leu Val Ser Ala
        290                 295                 300

Leu Arg Ala Gln Asp Val Glu Pro Ser Ala Val Arg Leu Gly Leu Leu
305                 310                 315                 320

Ala Gly His Tyr Arg Ala Asp Arg Phe Trp Ser Gln Gln Val Leu Asp
                325                 330                 335

Glu Ala Thr Ala Arg Leu His Arg Trp Arg Thr Ala Thr Ala Leu Pro
                340                 345                 350

Ala Gly Pro Ala Ala Val Asp Val Ala Arg Val Arg Arg Tyr Leu
                355                 360                 365

Ala Asp Asp Leu Asp Thr Pro Lys Ala Ile Ala Ala Leu Asp Gly Trp
370                 375                 380

Val Thr Asp Ala Val Glu Tyr Gly Gly His Asp Ala Gly Ala Pro Lys
385                 390                 395                 400

Leu Val Ala Thr Ala Ile Asp Ala Leu Leu Gly Val Asp Leu
                405                 410

<210> SEQ ID NO 5
<211> LENGTH: 404
<212> TYPE: PRT
<213> ORGANISM: Corynebacterium striatum

<400> SEQUENCE: 5

Met His Ala Trp Pro Asp Pro Ser Val Pro Ala Val Ala Gly Thr Pro
1               5                   10                  15

Val Pro Leu Lys Leu Phe Asp Thr Ala Asp Gln Arg Val Lys Glu Val
                20                  25                  30

Asp Thr Thr Pro Asp Ala Asn Gly Glu Val Gly Met Tyr Val Cys Gly
            35                  40                  45

Ile Thr Pro Tyr Asp Ser Thr His Leu Gly His Ala Ala Thr Tyr Leu
    50                  55                  60

Thr Phe Asp Leu Ala Gln Arg Gln Leu Leu Ala Asn Gly His Lys Val
65                  70                  75                  80

His Tyr Val Gln Asn Ile Thr Asp Val Asp Asp Pro Leu Phe Glu Arg
                85                  90                  95

Ala Glu Arg Asp Gly Val Asp Trp Arg Glu Leu Gly Thr Ser Gln Ile
            100                 105                 110

Asn Leu Phe Arg Ser Asp Met Glu Ile Leu Ser Val Ile Pro Pro Cys
        115                 120                 125

Asp Tyr Ile Gly Ala Met Glu Ser Val Asp Glu Val Ile Ala Met Val
    130                 135                 140

Gln Gln Leu Leu Asp Ala Gly Ala Ala Tyr Glu Leu Asp Gln Gly Asp
145                 150                 155                 160

Ile Tyr Ala Ser Ile Asp Ala Thr Glu Gln Phe Gly Tyr Glu Ser Asn
                165                 170                 175

Leu Asp Arg Ala Thr Met Glu Glu Tyr Phe Ala Glu Arg Gly Gly Asp
            180                 185                 190

Pro Asp Arg Glu Gly Lys Arg Asp Pro Leu Asp Ala Leu Val Trp Arg
        195                 200                 205

Gly His Arg Glu Gly Glu Pro Ala Trp Asp Ser Pro Phe Gly Pro Gly
```

```
            210                 215                 220
Arg Pro Gly Trp His Val Glu Cys Ser Ala Ile Ala Thr Asn Arg Leu
225                 230                 235                 240

Gly Ser His Phe Ala Ile Gln Gly Gly Gly Ser Asp Leu Ala Phe Pro
                245                 250                 255

His His Glu Phe Ser Ala Ala His Ala Glu Ala Ala Leu Lys Val Glu
                260                 265                 270

Arg Met Ala Gly His Tyr Val His Ala Gly Met Ile Ala Leu Asp Gly
                275                 280                 285

Val Lys Met Ser Lys Ser Leu Gly Asn Leu Val Phe Val His Lys Leu
                290                 295                 300

Ser Glu Ala Gly His Asp Pro Ser Ala Ile Arg Leu Ala Val Phe Ala
305                 310                 315                 320

Gly His Tyr Arg Glu Asp Arg Asp Phe Ser Asp Ala Ile Leu Ala Glu
                325                 330                 335

Ala Glu Glu Arg Leu Thr Arg Trp Arg Glu Gln Leu Ala Gly Glu Val
                340                 345                 350

Ser Glu Ala Glu Ala Thr Glu Val Val Asp Lys Leu Arg Ala Ile Leu
                355                 360                 365

Ala Asp Asp Leu Asn Thr Pro Glu Ala Leu Ser Leu Leu Asp Gly Ala
                370                 375                 380

Ala Gly Asp Cys Asn Gln Ile Ile Ala Thr Ala Leu Asp Gly Leu Leu
385                 390                 395                 400

Gly Val Arg Ile

<210> SEQ ID NO 6
<211> LENGTH: 409
<212> TYPE: PRT
<213> ORGANISM: Streptomyces coelicolor

<400> SEQUENCE: 6

Met His Ala Trp Pro Ala Ser Glu Val Pro Ala Leu Pro Gly Gln Gly
1               5                   10                  15

Arg Asp Leu Arg Ile His Asp Thr Ala Thr Gly Gly Pro Val Thr Leu
                20                  25                  30

Asp Pro Gly Pro Val Ala Arg Ile Tyr Val Cys Gly Ile Thr Pro Tyr
            35                  40                  45

Asp Ala Thr His Met Gly His Ala Ala Thr Tyr Asn Ala Phe Asp Leu
        50                  55                  60

Val Gln Arg Val Trp Leu Asp Thr Lys Arg Gln Val His Tyr Val Gln
65                  70                  75                  80

Asn Val Thr Asp Val Asp Asp Pro Leu Leu Glu Arg Ala Val Arg Asp
                85                  90                  95

Gly Val Asp Trp Thr Ala Leu Ala Glu Gln Glu Thr Ala Leu Phe Arg
                100                 105                 110

Glu Asp Met Thr Ala Leu Arg Met Leu Pro Pro Gln His Tyr Ile Gly
                115                 120                 125

Ala Val Glu Ala Ile Pro Gly Ile Val Pro Leu Val Glu Arg Leu Arg
                130                 135                 140

Asp Ala Gly Ala Ala Tyr Glu Leu Glu Gly Asp Val Tyr Phe Ser Val
145                 150                 155                 160

Glu Ala Asp Pro His Phe Gly Gly Val Ser His Leu Asp Ala Ala Thr
                165                 170                 175

Met Arg Leu Leu Ser Ala Glu Arg Gly Gly Asp Pro Asp Arg Pro Gly
```

-continued

```
                    180                 185                 190
Lys Lys Asn Pro Leu Asp Pro Met Leu Trp Met Ala Ala Arg Glu Gly
            195                 200                 205
Glu Pro Ser Trp Asp Gly Gly Thr Leu Gly Arg Gly Arg Pro Gly Trp
        210                 215                 220
His Ile Glu Cys Val Ala Ile Ala Leu Asp His Leu Gly Met Gly Phe
225                 230                 235                 240
Asp Val Gln Gly Gly Gly Ser Asp Leu Ala Phe Pro His His Glu Met
                245                 250                 255
Gly Ala Ser His Ala Gln Ala Leu Thr Gly Glu Phe Pro Met Ala Lys
            260                 265                 270
Ala Tyr Val His Ala Gly Met Val Gly Leu Asp Gly Glu Lys Met Ser
        275                 280                 285
Lys Ser Lys Gly Asn Leu Val Phe Val Ser Gln Leu Arg Arg Glu Gly
    290                 295                 300
Val Asp Pro Ala Ala Ile Arg Leu Thr Leu Leu Ala His His Tyr Arg
305                 310                 315                 320
Ser Asp Trp Glu Trp Thr Asp Gln Val Leu Gln Asp Ala Leu Ala Arg
                325                 330                 335
Leu Asp Arg Trp Arg Ala Ala Val Ser Arg Pro Asp Gly Pro Pro Ala
            340                 345                 350
Glu Ala Leu Val Glu Glu Ile Arg Glu Ala Leu Ala Asn Asp Leu Asp
        355                 360                 365
Ser Pro Ala Ala Leu Ala Ala Val Asp Arg Trp Ala Ala Leu Gln Gln
    370                 375                 380
Glu Ser Gly Gly Thr Asp Ile Gly Ala Pro Gly Val Val Ser Arg Ala
385                 390                 395                 400
Val Asp Ala Leu Leu Gly Val Ala Leu
                405

<210> SEQ ID NO 7
<211> LENGTH: 20
<212> TYPE: PRT
<213> ORGANISM: Mycobacterium smegmatis

<400> SEQUENCE: 7

Met Gln Ser Trp Ser Ala Pro Ala Ile Pro Val Val Pro Gly Arg Gly
1               5                   10                  15

Pro Ala Leu Arg
            20

<210> SEQ ID NO 8
<211> LENGTH: 18
<212> TYPE: PRT
<213> ORGANISM: Mycobacterium smegmatis
<220> FEATURE:
<221> NAME/KEY: MISC_FEATURE
<222> LOCATION: (1)..(1)
<223> OTHER INFORMATION: Xaa is Gly, Ser or Met
<220> FEATURE:
<221> NAME/KEY: MISC_FEATURE
<222> LOCATION: (2)..(2)
<223> OTHER INFORMATION: Xaa is Glu or Gln
<220> FEATURE:
<221> NAME/KEY: MISC_FEATURE
<222> LOCATION: (13)..(13)
<223> OTHER INFORMATION: Xaa is Ser, Asp or Pro

<400> SEQUENCE: 8

Xaa Xaa His Leu Lys Val Asp Ala Met Gln Ser Trp Xaa Ala Pro Ala
```

<210> SEQ ID NO 9
<211> LENGTH: 18
<212> TYPE: PRT
<213> ORGANISM: Mycobacterium smegmatis

<400> SEQUENCE: 9

Ser Glu His Leu Lys Val Asp Ala Met Gln Ser Trp Ser Ala Pro Ala
1               5                   10                  15
Ile Pro

<210> SEQ ID NO 10
<211> LENGTH: 28
<212> TYPE: DNA
<213> ORGANISM: Artificial sequence
<220> FEATURE:
<223> OTHER INFORMATION: PCR primer

<400> SEQUENCE: 10
gcggatccat gcagtcgtgg tattgccc                                      28

<210> SEQ ID NO 11
<211> LENGTH: 28
<212> TYPE: DNA
<213> ORGANISM: Artificial sequence
<220> FEATURE:
<223> OTHER INFORMATION: PCR primer

<400> SEQUENCE: 11
ccaagcttct acaggtccac cccgagca                                      28

<210> SEQ ID NO 12
<211> LENGTH: 469
<212> TYPE: PRT
<213> ORGANISM: Mycobacterium tuberculosis

<400> SEQUENCE: 12

Met Thr Asp Arg Ala Arg Leu Arg Leu His Asp Thr Ala Ala Gly Val
1               5                   10                  15

Val Arg Asp Phe Val Pro Leu Arg Pro Gly His Val Ser Ile Tyr Leu
                20                  25                  30

Cys Gly Ala Thr Val Gln Gly Leu Pro His Ile Gly His Val Arg Ser
            35                  40                  45

Gly Val Ala Phe Asp Ile Leu Arg Arg Trp Leu Leu Ala Arg Gly Tyr
        50                  55                  60

Asp Val Ala Phe Ile Arg Asn Val Thr Asp Ile Glu Asp Lys Ile Leu
65                  70                  75                  80

Ala Lys Ala Ala Ala Gly Arg Pro Trp Trp Glu Trp Ala Ala Thr
                85                  90                  95

His Glu Arg Ala Phe Thr Ala Ala Tyr Asp Ala Leu Asp Val Leu Pro
                100                 105                 110

Pro Ser Ala Glu Pro Arg Ala Thr Gly His Ile Thr Gln Met Ile Glu
            115                 120                 125

Met Ile Glu Arg Leu Ile Gln Ala Gly His Ala Tyr Thr Gly Gly Gly
        130                 135                 140

Asp Val Tyr Phe Asp Val Leu Ser Tyr Pro Glu Tyr Gly Gln Leu Ser
145                 150                 155                 160

Gly His Lys Ile Asp Asp Val His Gln Gly Glu Gly Val Ala Ala Gly
                165                 170                 175

Lys Arg Asp Gln Arg Asp Phe Thr Leu Trp Lys Gly Glu Lys Pro Gly
                180                 185                 190

Glu Pro Ser Trp Pro Thr Pro Trp Gly Arg Gly Arg Pro Gly Trp His
                195                 200                 205

Leu Glu Cys Ser Ala Met Ala Arg Ser Tyr Leu Gly Pro Glu Phe Asp
                210                 215                 220

Ile His Cys Gly Gly Met Asp Leu Val Phe Pro His His Glu Asn Glu
225                 230                 235                 240

Ile Ala Gln Ser Arg Ala Ala Gly Asp Gly Phe Ala Arg Tyr Trp Leu
                245                 250                 255

His Asn Gly Trp Val Thr Met Gly Gly Glu Lys Met Ser Lys Ser Leu
                260                 265                 270

Gly Asn Val Leu Ser Met Pro Ala Met Leu Gln Arg Val Arg Pro Ala
                275                 280                 285

Glu Leu Arg Tyr Tyr Leu Gly Ser Ala His Tyr Arg Ser Met Leu Glu
                290                 295                 300

Phe Ser Glu Thr Ala Met Gln Asp Ala Val Lys Ala Tyr Val Gly Leu
305                 310                 315                 320

Glu Asp Phe Leu His Arg Val Arg Thr Arg Val Gly Ala Val Cys Pro
                325                 330                 335

Gly Asp Pro Thr Pro Arg Phe Ala Glu Ala Leu Asp Asp Leu Ser
                340                 345                 350

Val Pro Ile Ala Leu Ala Glu Ile His His Val Arg Ala Glu Gly Asn
                355                 360                 365

Arg Ala Leu Asp Ala Gly Asp His Asp Gly Ala Leu Arg Ser Ala Ser
                370                 375                 380

Ala Ile Arg Ala Met Met Gly Ile Leu Gly Cys Asp Pro Leu Asp Gln
385                 390                 395                 400

Arg Trp Glu Ser Arg Asp Glu Thr Ser Ala Ala Leu Ala Ala Val Asp
                405                 410                 415

Val Leu Val Gln Ala Glu Leu Gln Asn Arg Glu Lys Ala Arg Glu Gln
                420                 425                 430

Arg Asn Trp Ala Leu Ala Asp Glu Ile Arg Gly Arg Leu Lys Arg Ala
                435                 440                 445

Gly Ile Glu Val Thr Asp Thr Ala Asp Gly Pro Gln Trp Ser Leu Leu
    450                 455                 460

Gly Gly Asp Thr Lys
465

<210> SEQ ID NO 13
<211> LENGTH: 461
<212> TYPE: PRT
<213> ORGANISM: Escherichia coli

<400> SEQUENCE: 13

Met Leu Lys Ile Phe Asn Thr Leu Thr Arg Gln Lys Glu Glu Phe Lys
1               5                   10                  15

Pro Ile His Ala Gly Glu Val Gly Met Tyr Val Cys Gly Ile Thr Val
                20                  25                  30

Tyr Asp Leu Cys His Ile Gly His Gly Arg Thr Phe Val Ala Phe Asp
                35                  40                  45

Val Val Ala Arg Tyr Leu Arg Phe Leu Gly Tyr Lys Leu Lys Tyr Val
                50                  55                  60

```
Arg Asn Ile Thr Asp Ile Asp Asp Lys Ile Ile Lys Arg Ala Asn Glu
 65                  70                  75                  80

Asn Gly Glu Ser Phe Val Ala Leu Val Asp Arg Met Ile Ala Glu Met
             85                  90                  95

His Lys Asp Phe Asp Ala Leu Asn Ile Leu Arg Pro Asp Met Glu Pro
            100                 105                 110

Arg Ala Thr His His Ile Ala Glu Ile Ile Glu Leu Thr Glu Gln Leu
        115                 120                 125

Ile Ala Lys Gly His Ala Tyr Val Ala Asp Asn Gly Asp Val Met Phe
130                 135                 140

Asp Val Pro Thr Asp Pro Thr Tyr Gly Val Leu Ser Arg Gln Asp Leu
145                 150                 155                 160

Asp Gln Leu Gln Ala Gly Ala Arg Val Asp Val Val Asp Asp Lys Arg
                165                 170                 175

Asn Pro Met Asp Phe Val Leu Trp Lys Met Ser Lys Glu Gly Glu Pro
            180                 185                 190

Ser Trp Pro Ser Pro Trp Gly Ala Gly Arg Pro Gly Trp His Ile Glu
        195                 200                 205

Cys Ser Ala Met Asn Cys Lys Gln Leu Gly Asn His Phe Asp Ile His
210                 215                 220

Gly Gly Gly Ser Asp Leu Met Phe Pro His His Glu Asn Glu Ile Ala
225                 230                 235                 240

Gln Ser Thr Cys Ala His Asp Gly Gln Tyr Val Asn Tyr Trp Met His
                245                 250                 255

Ser Gly Met Val Met Val Asp Arg Glu Lys Met Ser Lys Ser Leu Gly
            260                 265                 270

Asn Phe Phe Thr Val Arg Asp Val Leu Lys Tyr Tyr Asp Ala Glu Thr
        275                 280                 285

Val Arg Tyr Phe Leu Met Ser Gly His Tyr Arg Ser Gln Leu Asn Tyr
290                 295                 300

Ser Glu Glu Asn Leu Lys Gln Ala Arg Ala Ala Leu Glu Arg Leu Tyr
305                 310                 315                 320

Thr Ala Leu Arg Gly Thr Asp Lys Thr Val Ala Pro Ala Gly Gly Glu
                325                 330                 335

Ala Phe Glu Ala Arg Phe Ile Glu Ala Met Asp Asp Phe Asn Thr
            340                 345                 350

Pro Glu Ala Tyr Ser Val Leu Phe Asp Met Ala Arg Glu Val Asn Arg
        355                 360                 365

Leu Lys Val Glu Asp Met Ala Ala Asn Ala Met Ala Ser His Leu
370                 375                 380

Arg Lys Leu Ser Ala Val Leu Gly Leu Leu Glu Gln Glu Pro Glu Ala
385                 390                 395                 400

Phe Leu Gln Ser Gly Ala Gln Ala Asp Ser Glu Val Ala Glu Ile
                405                 410                 415

Glu Ala Leu Ile Gln Gln Arg Leu Asp Ala Arg Lys Ala Lys Asp Trp
            420                 425                 430

Ala Ala Ala Asp Ala Ala Arg Asp Arg Leu Asn Glu Met Gly Ile Val
        435                 440                 445

Leu Glu Asp Gly Pro Gln Gly Thr Thr Trp Arg Arg Lys
450                 455                 460

<210> SEQ ID NO 14
<211> LENGTH: 315
```

<212> TYPE: PRT
<213> ORGANISM: Mycobacterium tuberculosis

<400> SEQUENCE: 14

Met Thr Ala Leu Asp Trp Arg Ser Ala Leu Thr Ala Asp Glu Gln Arg
1               5                   10                  15

Ser Val Arg Ala Leu Val Thr Ala Thr Ala Val Asp Gly Val Ala
            20                  25                  30

Pro Val Gly Glu Gln Val Leu Arg Glu Leu Gly Gln Gln Arg Thr Glu
            35                  40                  45

His Leu Leu Val Ala Gly Ser Arg Pro Gly Pro Ile Ile Gly Tyr
    50                  55                  60

Leu Asn Leu Ser Pro Pro Arg Gly Ala Gly Ala Met Ala Glu Leu
65                  70                  75                  80

Val Val His Pro Gln Ser Arg Arg Gly Ile Gly Thr Ala Met Ala
                85                  90                  95

Arg Ala Ala Leu Ala Lys Thr Ala Gly Arg Asn Gln Phe Trp Ala His
                100                 105                 110

Gly Thr Leu Asp Pro Ala Arg Ala Thr Ala Ser Ala Leu Gly Leu Val
            115                 120                 125

Gly Val Arg Glu Leu Ile Gln Met Arg Arg Pro Leu Arg Asp Ile Pro
        130                 135                 140

Glu Pro Thr Ile Pro Asp Gly Val Val Ile Arg Thr Tyr Ala Gly Thr
145                 150                 155                 160

Ser Asp Asp Ala Glu Leu Leu Arg Val Asn Asn Ala Ala Phe Ala Gly
                165                 170                 175

His Pro Glu Gln Gly Gly Trp Thr Ala Val Gln Leu Ala Glu Arg Arg
            180                 185                 190

Gly Glu Ala Trp Phe Asp Pro Asp Gly Leu Ile Leu Ala Phe Gly Asp
        195                 200                 205

Ser Pro Arg Glu Arg Pro Gly Arg Leu Leu Gly Phe His Trp Thr Lys
    210                 215                 220

Val His Pro Asp His Pro Gly Leu Gly Glu Val Tyr Val Leu Gly Val
225                 230                 235                 240

Asp Pro Ala Ala Gln Arg Arg Gly Leu Gly Gln Met Leu Thr Ser Ile
                245                 250                 255

Gly Ile Val Ser Leu Ala Arg Arg Leu Gly Arg Lys Thr Leu Asp
            260                 265                 270

Pro Ala Val Glu Pro Ala Val Leu Leu Tyr Val Glu Ser Asp Asn Val
        275                 280                 285

Ala Ala Val Arg Thr Tyr Gln Ser Leu Gly Phe Thr Thr Tyr Ser Val
    290                 295                 300

Asp Thr Ala Tyr Ala Leu Ala Gly Thr Asp Asn
305                 310                 315

<210> SEQ ID NO 15
<211> LENGTH: 295
<212> TYPE: PRT
<213> ORGANISM: Mycobacterium smegmatis

<400> SEQUENCE: 15

Val Thr Ser Thr Glu Trp Arg Thr Gly Leu Thr Gly Ala Gln Gln Ala
1               5                   10                  15

Glu Ile Arg Ala Leu Ile Asp Ala Ala Thr Thr His Asp Gly Val Ala
            20                  25                  30

-continued

Pro Val Gly Asp Gln Val Leu Arg Glu Leu Gly Arg Asp Arg Thr Arg
           35                  40                  45

His Leu Leu Thr Thr Asp Asp Arg Val Val Gly Tyr Leu Asn Leu
 50                  55                  60

Ala Pro Ala Glu Gly Asp Pro Ala Met Ala Glu Leu Val Val His
 65                  70                  75                  80

Pro Gln Ala Arg Arg Gly Ile Gly Ala Met Ala Arg Thr Ala
               85                  90                  95

Leu Ala Glu Gly Gly Pro Gly Ala Arg Ile Trp Ala His Gly Asn Ile
              100                 105                 110

Ala Ala Ala Gln Ala Met Ala Ser Ser Leu Arg Leu Val Val Arg
              115                 120                 125

Glu Leu Leu Gln Met Arg Arg Pro Leu Thr Asp Leu Pro Pro Val Pro
 130                 135                 140

Asp Thr Pro Gly Val Arg Ile Ala Thr Tyr Ala Gly Pro Gly Asp Asp
 145                 150                 155                 160

Ala Glu Ile Leu Arg Val Asn Asn Ala Ala Phe Ser Trp His Pro Glu
                 165                 170                 175

Gln Gly Gly Trp Thr Glu His Glu Ile Asp Glu Arg Arg Asn Glu Gly
              180                 185                 190

Trp Phe Asp Pro Glu Gly Leu Phe Gln Ala Phe Asp Glu Gln Thr Gly
              195                 200                 205

Ser Leu Leu Gly Phe His Trp Thr Lys Ile His Asp Ala Ser Leu Gly
 210                 215                 220

Glu Val Tyr Val Val Gly Val Asp Pro Gln Ala Gln Gly Arg Gly Leu
225                 230                 235                 240

Gly Tyr Thr Leu Thr Leu Ile Gly Leu His His Leu Ala Glu Lys Leu
                 245                 250                 255

Ala Gly Pro Glu Pro Thr Val Leu Leu Tyr Val Glu Ala Asp Asn Ser
              260                 265                 270

Ala Ala Val Asn Thr Tyr Arg Lys Leu Gly Phe Glu Val Phe Ser Val
              275                 280                 285

Asp Ala Ala Tyr Ala Ala Asn
              290                 295

<210> SEQ ID NO 16
<211> LENGTH: 311
<212> TYPE: PRT
<213> ORGANISM: Mycobacterium leprae

<400> SEQUENCE: 16

Met Val Leu Asn Trp Arg Phe Ala Leu Ser Ala Asp Glu Gln Arg Leu
 1               5                  10                  15

Val Arg Glu Ile Ile Ser Ala Ala Thr Glu Phe Asp Glu Val Ser Pro
              20                  25                  30

Val Gly Glu Gln Val Leu Arg Glu Leu Gly Tyr Asp Arg Thr Glu His
              35                  40                  45

Leu Leu Val Thr Asp Ser Arg Pro Tyr Ala Pro Ile Ile Gly Tyr Leu
 50                  55                  60

Asn Leu Ser Ser Pro Arg Asp Ala Gly Val Ala Met Ala Glu Leu Val
 65                  70                  75                  80

Val His Pro Arg Glu Arg Arg Gly Val Gly Ala Ala Met Val Arg
              85                  90                  95

Ala Ala Leu Ala Lys Thr Gly Gly Arg Asn Arg Phe Trp Ala His Gly
              100                 105                 110

```
Thr Leu Ala Ser Ala Arg Ala Thr Ala Ser Val Leu Gly Leu Val Pro
            115                 120                 125

Val Arg Glu Leu Val Gln Met Gln Arg Ser Leu Arg Thr Ile Pro Asp
130                 135                 140

Pro Met Val Pro Asp Gln Leu Gly Val Trp Val Arg Thr Tyr Val Gly
145                 150                 155                 160

Thr Val Asp Asp Ala Glu Leu Leu Arg Val Asn Asn Ala Ala Phe Ala
                165                 170                 175

Gly His Pro Glu Gln Gly Gly Trp Thr Ala Thr Gln Leu Ala Glu Arg
            180                 185                 190

Arg Ser Glu Pro Trp Phe Asp Pro Ala Gly Leu Phe Leu Ala Phe Gly
        195                 200                 205

Asp Ser Ser Asn Gln Pro Gly Lys Leu Leu Gly Phe His Trp Thr
        210                 215                 220

Lys Val His Ala Ala His Pro Gly Leu Gly Glu Val Tyr Val Leu Gly
225                 230                 235                 240

Val Asp Pro Ser Ala Gln Gly Arg Gly Leu Gly Gln Met Leu Thr Ser
                245                 250                 255

Ile Gly Ile Ala Ser Leu Ala Gln Arg Leu Val Gly Pro Ser Ala Glu
            260                 265                 270

Pro Thr Val Met Leu Tyr Val Glu Ser Asp Asn Val Ala Ala Ala Arg
        275                 280                 285

Thr Tyr Glu Arg Leu Gly Phe Thr Thr Tyr Ser Val Asp Thr Ala Tyr
        290                 295                 300

Ala Leu Ala Arg Ile Asp Asp
305                 310

<210> SEQ ID NO 17
<211> LENGTH: 309
<212> TYPE: PRT
<213> ORGANISM: Streptomyces coelicolor

<400> SEQUENCE: 17

Met Thr Ser Asp Asp Thr Val Arg Pro Gly Arg Pro Arg Ser Ile Glu
1               5                   10                  15

Thr Leu Ala Glu Leu Thr Pro Glu Gln Thr Asp Ala Val Leu Ala Leu
            20                  25                  30

Leu Thr Glu Ala Ala Arg Thr Asp Gly Gln His Ala Val Ser Glu Gln
        35                  40                  45

Gly Arg Leu Gln Leu Arg Gly Pro Ala Arg Glu Gly Val Val His Leu
    50                  55                  60

Leu Leu Thr Leu Asp Gly Gly Glu Leu Val Gly Tyr Ala Gln Leu Glu
65                  70                  75                  80

Gly Thr Asp Pro Val Glu Pro Pro Ala Ala Glu Leu Val Val His Pro
                85                  90                  95

Ser His Arg Gly Gln Gly His Gly Arg Ala Leu Gly Ser Ala Leu Leu
            100                 105                 110

Ala Ala Ser Gly Lys Arg Leu Arg Ile Trp Ala His Gly Gly His Ser
        115                 120                 125

Ala Ala Arg His Leu Ala Gln Val Leu Gly Leu Ser Leu Phe Arg Glu
    130                 135                 140

Leu Arg Gln Leu Arg Arg Pro Leu Thr Gly Leu Asp Leu Pro Glu Pro
145                 150                 155                 160

Arg Leu Pro Glu Gly Val Ser Val Arg Thr Phe Val Pro Gly Gln Asp
```

```
                165                 170                 175
Asp Ala Ala Trp Leu Ala Val Asn Ala Ala Phe Ala His His Pro
            180                 185                 190

Glu Gln Gly Ser Leu Thr Gln Arg Asp Leu Asp Arg Lys Ala Glu
        195                 200                 205

Pro Trp Phe Asp Pro Ala Gly Phe Leu Ala Glu Arg Asp Gly Glu
    210                 215                 220

Leu Ile Gly Phe His Trp Thr Lys Val His Ala Glu Arg Leu Gly
225                 230                 235                 240

Glu Val Tyr Val Leu Gly Ile Arg Pro Asp Thr Gln Gly Gly Leu
            245                 250                 255

Gly Lys Ala Leu Thr Thr Ile Gly Leu Arg His Leu Glu Gly Gln Gly
        260                 265                 270

Leu Pro Thr Ala Met Leu Tyr Val Asp Ala Asp Asn Lys Ala Ala Val
    275                 280                 285

Ala Val Tyr Glu Arg Leu Gly Phe Val Thr His Glu Thr Asp Leu Met
290                 295                 300

Tyr Arg Thr Glu Thr
305

<210> SEQ ID NO 18
<211> LENGTH: 301
<212> TYPE: PRT
<213> ORGANISM: Corynebacterium diphtheriae

<400> SEQUENCE: 18

Met Ile Glu Thr Ser Leu Ala Ser Ala Ser Ala Ala Leu Arg Asp Arg
1               5                   10                  15

Val Asp Glu Ile Leu Ala Ala Ala Thr Arg Glu Asp Gly Cys Ala Pro
            20                  25                  30

Leu Ser Glu Ser Phe Leu Asn Gly Leu Arg Arg Ala Asp Asp Gly His
        35                  40                  45

Val His Ser Cys Val Met Asp Ser His Asp Gln Val Val Gly Val Ala
    50                  55                  60

Ala Arg Asp Gly Asp Ser Ala Glu Val Val Asp Pro Ala Phe Arg
65                  70                  75                  80

Arg Gln Gly Tyr Gly Ser Phe Leu Ile Arg His Val Val Ser Gln Gly
            85                  90                  95

Val Lys Asn Val Trp Ala His Gly Asp Gly Ala Gly Ala Lys Ala Val
        100                 105                 110

Ala Lys Ala Leu Gln Leu Glu Gln Thr Arg Gln Leu Leu Val Met Ala
    115                 120                 125

Val Glu Gly Asp Arg Leu Val Glu Ser Ala Gln Leu Gln Val Pro Ser
130                 135                 140

Gly Phe Arg Val Leu Ala Leu Asn Glu Ala Tyr Glu Ser Ile Pro Asp
145                 150                 155                 160

Ile Glu Gln Gln Trp Leu Arg Val Asn Asn Glu Ala Phe Glu Trp His
            165                 170                 175

Pro Glu Gln Gly Gly Trp Asp Ser Ala Arg Leu Ala Gln Ala Arg Asp
        180                 185                 190

Thr Gln Trp Phe Arg Glu Ser Asp Val Leu Phe Leu Ile Asp Thr Ala
    195                 200                 205

Lys Arg Thr Val Ala Gly Phe His Trp Thr Lys Arg His Gly Asp Leu
210                 215                 220
```

```
Ala Glu Gly Ala Asp Gly Glu Val Tyr Val Val Gly Leu Gly Ser Ala
225                 230                 235                 240

Tyr Arg Arg Arg Gly Leu Gly Asp Leu Leu Ile Arg Met Gly Leu His
            245                 250                 255

His Leu Glu Tyr Glu His Ala Arg Arg Val Ile Leu Tyr Val Glu Gly
        260                 265                 270

Asp Asn Glu Ser Ala Arg Arg Ala Tyr Asp Ala Leu Gly Phe His Val
    275                 280                 285

Val Glu Ser His Val Thr Tyr Ser Pro Gln Ser Ser Ser
    290                 295                 300
```

<210> SEQ ID NO 19
<211> LENGTH: 434
<212> TYPE: PRT
<213> ORGANISM: Mycobacterium smegmatis

<400> SEQUENCE: 19

```
Val Arg Leu Ala Thr Asp Leu Glu Thr Pro Arg Val Ala Val Leu
1               5                   10                  15

Ser Val His Thr Ser Pro Leu Ala Gln Pro Gly Thr Gly Asp Ala Gly
            20                  25                  30

Gly Met Asn Val Tyr Val Leu Gln Thr Ala Leu Gln Leu Ala Arg Arg
        35                  40                  45

Gly Val Glu Val Glu Val Phe Thr Arg Ala Thr Ser Ser Ala Asp Ala
    50                  55                  60

Pro Val Val Pro Val Ala Pro Gly Val Leu Val Arg Asn Val Val Ala
65                  70                  75                  80

Gly Pro Phe Glu Gly Leu Asp Lys Asn Asp Leu Pro Thr Gln Leu Cys
            85                  90                  95

Ala Phe Thr Ala Gly Val Leu Arg Ala Glu Ala Thr His Glu Pro Gly
        100                 105                 110

Tyr Tyr Asp Val Val His Ser His Tyr Trp Leu Ser Gly Gln Val Gly
    115                 120                 125

Trp Leu Ala Arg Asp Arg Trp Ala Val Pro Leu Val His Thr Ala His
130                 135                 140

Thr Leu Ala Ala Val Lys Asn Ala Ala Leu Ala Ala Gly Asp Ala Pro
145                 150                 155                 160

Glu Pro Pro Leu Arg Ala Val Gly Glu Gln Gln Val Val Asp Glu Ala
            165                 170                 175

Asp Arg Leu Ile Val Asn Thr Glu Val Glu Ala Gln Gln Leu Val Ser
        180                 185                 190

Leu His Asn Ala Asp Arg Ser Arg Ile Asp Val Val His Pro Gly Val
    195                 200                 205

Asp Leu Asp Val Phe Thr Pro Gly Ser Arg Ala Ala Arg Ala Val
    210                 215                 220

Phe Gly Leu Pro Thr Asp Gln Lys Ile Val Ala Phe Val Gly Arg Ile
225                 230                 235                 240

Gln Pro Leu Lys Ala Pro Asp Ile Leu Leu Arg Ala Ala Ala Lys Leu
            245                 250                 255

Pro Gly Val Arg Val Leu Ile Ala Gly Gly Pro Ser Gly Ser Gly Leu
        260                 265                 270

Ala Gln Pro Asp Thr Leu Val Arg Leu Ala Asp Glu Leu Gly Ile Ser
    275                 280                 285

Asp Arg Val Thr Phe Leu Pro Pro Gln Ser Arg Glu Gln Leu Val Asn
    290                 295                 300
```

```
Val Tyr Arg Ala Ala Asp Leu Val Ala Val Pro Ser Tyr Ser Glu Ser
305                 310                 315                 320

Phe Gly Leu Val Ala Val Glu Ala Gln Ala Cys Gly Thr Pro Val Val
                325                 330                 335

Ala Ala Ala Val Gly Gly Leu Pro Val Ala Val Ala Asp Gly Val Ser
                340                 345                 350

Gly Ala Leu Val Asp Gly His Asp Ile Gly Asp Trp Ala Asp Thr Ile
                355                 360                 365

Ser Glu Val Leu Asp Arg Glu Pro Ala Ala Leu Ser Arg Ala Ser Ala
            370                 375                 380

Glu His Ala Ala Gln Phe Ser Trp Ala His Thr Val Asp Ala Leu Leu
385                 390                 395                 400

Ala Ser Tyr Ser Arg Ala Met Ser Asp Tyr Arg Ala Arg His Pro Arg
                405                 410                 415

Pro Ala Ala Arg Arg Ser Gly Arg Arg Phe Ser Met Arg Arg Gly Val
                420                 425                 430

Arg Thr

<210> SEQ ID NO 20
<211> LENGTH: 480
<212> TYPE: PRT
<213> ORGANISM: Mycobacterium tuberculosis

<400> SEQUENCE: 20

Met Ala Gly Val Arg His Asp Asp Gly Ser Gly Leu Ile Ala Gln Arg
1               5                   10                  15

Arg Pro Val Arg Gly Glu Gly Ala Thr Arg Ser Arg Gly Pro Ser Gly
                20                  25                  30

Pro Ser Asn Arg Asn Val Ser Ala Ala Asp Pro Arg Arg Val Ala
                35                  40                  45

Leu Leu Ala Val His Thr Ser Pro Leu Ala Gln Pro Gly Thr Gly Asp
            50                  55                  60

Ala Gly Gly Met Asn Val Tyr Met Leu Gln Ser Ala Leu His Leu Ala
65                  70                  75                  80

Arg Arg Gly Ile Glu Val Glu Ile Phe Thr Arg Ala Thr Ala Ser Ala
                85                  90                  95

Asp Pro Pro Val Val Arg Val Ala Pro Gly Val Leu Val Arg Asn Val
                100                 105                 110

Val Ala Gly Pro Phe Glu Gly Leu Asp Lys Tyr Asp Leu Pro Thr Gln
                115                 120                 125

Leu Cys Ala Phe Ala Ala Gly Val Leu Arg Ala Glu Ala Val His Glu
            130                 135                 140

Pro Gly Tyr Tyr Asp Ile Val His Ser His Tyr Trp Leu Ser Gly Gln
145                 150                 155                 160

Val Gly Trp Leu Ala Arg Asp Arg Trp Ala Val Pro Leu Val His Thr
                165                 170                 175

Ala His Thr Leu Ala Ala Val Lys Asn Ala Ala Leu Ala Asp Gly Asp
                180                 185                 190

Gly Pro Glu Pro Pro Leu Arg Thr Val Gly Glu Gln Gln Val Val Asp
            195                 200                 205

Glu Ala Asp Arg Leu Ile Val Asn Thr Asp Asp Glu Ala Arg Gln Val
            210                 215                 220

Ile Ser Leu His Gly Ala Asp Pro Ala Arg Ile Asp Val Val His Pro
225                 230                 235                 240
```

```
Gly Val Asp Leu Asp Val Phe Arg Pro Gly Asp Arg Ala Ala Arg
            245                 250                 255

Ala Ala Leu Gly Leu Pro Val Asp Glu Arg Val Val Ala Phe Val Gly
            260                 265                 270

Arg Ile Gln Pro Leu Lys Ala Pro Asp Ile Val Leu Arg Ala Ala Ala
            275                 280                 285

Lys Leu Pro Gly Val Arg Ile Ile Val Ala Gly Pro Ser Gly Ser
            290                 295                 300

Gly Leu Ala Ser Pro Asp Gly Leu Val Arg Leu Ala Asp Glu Leu Gly
305                 310                 315                 320

Ile Ser Ala Arg Val Thr Phe Leu Pro Pro Gln Ser His Thr Asp Leu
                    325                 330                 335

Ala Thr Leu Phe Arg Ala Ala Asp Leu Val Ala Val Pro Ser Tyr Ser
                    340                 345                 350

Glu Ser Phe Gly Leu Val Ala Val Glu Ala Gln Ala Cys Gly Thr Pro
                355                 360                 365

Val Val Ala Ala Val Gly Gly Leu Pro Val Ala Val Arg Asp Gly
            370                 375                 380

Ile Thr Gly Thr Leu Val Ser Gly His Glu Val Gly Gln Trp Ala Asp
385                 390                 395                 400

Ala Ile Asp His Leu Leu Arg Leu Cys Ala Gly Pro Arg Gly Arg Val
                    405                 410                 415

Met Ser Arg Ala Ala Arg His Ala Ala Thr Phe Ser Trp Glu Asn
                420                 425                 430

Thr Thr Asp Ala Leu Leu Ala Ser Tyr Arg Arg Ala Ile Gly Glu Tyr
            435                 440                 445

Asn Ala Glu Arg Gln Arg Arg Gly Gly Glu Val Ile Ser Asp Leu Val
            450                 455                 460

Ala Val Gly Lys Pro Arg His Trp Thr Pro Arg Arg Gly Val Gly Ala
465                 470                 475                 480

<210> SEQ ID NO 21
<211> LENGTH: 425
<212> TYPE: PRT
<213> ORGANISM: Anabaena PCC7120

<400> SEQUENCE: 21

Met Phe Gln Asn Lys Lys His Arg Ile Ala Leu Ile Ser Val Ser Gly
1               5                   10                  15

Asp Pro Ala Val Glu Ile Gly Gln Glu Glu Ala Gly Gly Gln Asn Val
            20                  25                  30

Tyr Val Arg Glu Val Gly Tyr Ala Leu Ala Glu Gln Gly Trp Gln Val
        35                  40                  45

Asp Met Phe Thr Arg Arg Ile Ser Pro Asp Gln Ala Glu Ile Val Gln
    50                  55                  60

His Ser Pro Asn Cys Arg Thr Ile Arg Leu Gln Ala Gly Pro Val Glu
65                  70                  75                  80

Phe Ile Gly Arg Asp His Val Phe Asp Tyr Leu Pro Glu Phe Val Ala
                85                  90                  95

Glu Phe Gln Arg Phe Gln Lys Arg Gln Gly Tyr Asn Tyr Gln Leu Ile
            100                 105                 110

His Thr Asn Tyr Trp Leu Ser Ser Trp Val Gly Met Gln Leu Lys Lys
        115                 120                 125

Gln Gln Pro Leu Val Leu Val His Thr Tyr His Ser Leu Gly Ala Ile
```

```
            130                 135                 140
Lys Tyr Gln Thr Ile Ala Asp Ile Pro Ala Ile Ala Asn Gln Arg Leu
145                 150                 155                 160

Ala Ile Glu Lys Ala Cys Leu Glu Ser Val Asp Thr Val Ala Thr
                165                 170                 175

Ser Pro Gln Glu Gln Gln His Met Arg Ala Leu Val Ser Lys Lys Gly
                180                 185                 190

Arg Ile Glu Met Ile Pro Cys Gly Thr Asp Ile Asn Asn Phe Gly Asn
                195                 200                 205

Ile Glu Lys Ser Ala Ala Arg Glu Lys Leu Gly Ile Glu Pro Asp Ala
210                 215                 220

Lys Met Val Phe Tyr Val Gly Arg Phe Asp Pro Arg Lys Gly Ile Glu
225                 230                 235                 240

Thr Leu Val Arg Ala Val Ala Gln Ser Arg Leu Arg Gly Glu Ala Asn
                245                 250                 255

Leu Gln Leu Val Ile Gly Gly Ser Arg Pro Gly Gln Ser Asp Gly
                260                 265                 270

Arg Glu Arg Asp Arg Ile Ala Asn Ile Val Ala Glu Leu Glu Leu Asn
                275                 280                 285

Asp Cys Thr Thr Phe Ala Gly Arg Leu Asp His Glu Ile Leu Pro Tyr
                290                 295                 300

Tyr Tyr Ala Ala Ala Asp Val Cys Val Val Pro Ser His Tyr Glu Pro
305                 310                 315                 320

Phe Gly Leu Val Ala Ile Glu Ala Met Ala Ser Lys Thr Pro Val Ile
                325                 330                 335

Ala Ser Asn Val Gly Gly Leu Gln Phe Thr Val Val Pro Glu Val Thr
                340                 345                 350

Gly Leu Leu Ala Pro Pro Gln Asp Glu Ser Ala Phe Ala Thr Ala Ile
                355                 360                 365

Asp Arg Ile Leu Ala Asn Pro Thr Trp Arg Asp Gln Leu Gly Thr Ala
                370                 375                 380

Ala Arg Gln Arg Val Glu Thr Thr Phe Ser Trp Ala Gly Val Ala Ser
385                 390                 395                 400

Gln Leu Ser Gln Leu Tyr Thr His Leu Leu Thr Gln Asn Ala Pro Glu
                405                 410                 415

Lys Lys Glu Lys Glu Ala Val Ala Ala
                420                 425

<210> SEQ ID NO 22
<211> LENGTH: 378
<212> TYPE: PRT
<213> ORGANISM: Mycobacterium tuberculosis

<400> SEQUENCE: 22

Val Cys Gly Val Arg Val Ala Ile Val Ala Glu Ser Phe Leu Pro Gln
1               5                   10                  15

Val Asn Gly Val Ser Asn Ser Val Val Lys Val Leu Glu His Leu Arg
                20                  25                  30

Arg Thr Gly His Glu Ala Leu Val Ile Ala Pro Asp Thr Pro Pro Gly
            35                  40                  45

Glu Asp Arg Ala Glu Arg Leu His Asp Gly Val Arg Val His Arg Val
        50                  55                  60

Pro Ser Arg Met Phe Pro Lys Val Thr Thr Leu Pro Leu Gly Val Pro
65              70                  75                  80
```

```
Thr Phe Arg Met Leu Arg Ala Leu Arg Gly Phe Asp Pro Asp Val Val
                85                  90                  95

His Leu Ala Ser Pro Ala Leu Leu Gly Tyr Gly Leu His Ala Ala
            100                 105                 110

Arg Arg Leu Gly Val Pro Thr Val Ala Val Tyr Gln Thr Asp Val Pro
            115                 120                 125

Gly Phe Ala Ser Ser Tyr Gly Ile Pro Met Thr Ala Arg Ala Ala Trp
        130                 135                 140

Ala Trp Phe Arg His Leu His Arg Leu Ala Asp Arg Thr Leu Ala Pro
145                 150                 155                 160

Ser Thr Ala Thr Met Glu Ser Leu Ile Ala Gln Gly Ile Pro Arg Val
                165                 170                 175

His Arg Trp Ala Arg Gly Val Asp Val Gln Arg Phe Ala Pro Ser Ala
            180                 185                 190

Arg Asn Glu Val Leu Arg Arg Trp Ser Pro Asp Gly Lys Pro Ile
        195                 200                 205

Val Gly Phe Val Gly Arg Leu Ala Pro Glu Lys His Val Asp Arg Leu
    210                 215                 220

Thr Gly Leu Ala Ala Ser Gly Ala Val Arg Leu Val Ile Val Gly Asp
225                 230                 235                 240

Gly Ile Asp Arg Ala Arg Leu Gln Ser Ala Met Pro Thr Ala Val Phe
                245                 250                 255

Thr Gly Ala Arg Tyr Gly Lys Glu Leu Ala Glu Ala Tyr Ala Ser Met
            260                 265                 270

Asp Val Phe Val His Ser Gly Glu His Glu Thr Phe Cys Gln Val Val
        275                 280                 285

Gln Glu Ala Leu Ala Ser Gly Leu Pro Val Ile Ala Pro Asp Ala Gly
    290                 295                 300

Gly Pro Arg Asp Leu Ile Thr Pro His Arg Thr Gly Leu Leu Leu Pro
305                 310                 315                 320

Val Gly Glu Phe Glu His Arg Leu Pro Asp Ala Val Ala His Leu Val
                325                 330                 335

His Glu Arg Gln Arg Tyr Ala Leu Ala Ala Arg Arg Ser Val Leu Gly
            340                 345                 350

Arg Ser Trp Pro Val Val Cys Asp Glu Leu Leu Gly His Tyr Glu Ala
        355                 360                 365

Val Arg Gly Arg Arg Thr Thr Gln Ala Ala
    370                 375

<210> SEQ ID NO 23
<211> LENGTH: 31
<212> TYPE: DNA
<213> ORGANISM: Artificial sequence
<220> FEATURE:
<223> OTHER INFORMATION: PCR primer

<400> SEQUENCE: 23
ggcttgcagg tgacggcgct tgactggcgc t                             31

<210> SEQ ID NO 24
<211> LENGTH: 30
<212> TYPE: DNA
<213> ORGANISM: Artificial sequence
<220> FEATURE:
<223> OTHER INFORMATION: PCR primer

<400> SEQUENCE: 24
```

-continued

```
<210> SEQ ID NO 25
<211> LENGTH: 23
<212> TYPE: DNA
<213> ORGANISM: Artificial sequence
<220> FEATURE:
<223> OTHER INFORMATION: PCR primer

<400> SEQUENCE: 25
catatgcacg gtcggcaagg agg                                           23

<210> SEQ ID NO 26
<211> LENGTH: 25
<212> TYPE: DNA
<213> ORGANISM: Artificial Sequence
<220> FEATURE:
<223> OTHER INFORMATION: PCR primer

<400> SEQUENCE: 26
aggatccatg gcaggtgtgc ggcac                                         25

<210> SEQ ID NO 27
<211> LENGTH: 22
<212> TYPE: DNA
<213> ORGANISM: Artificial sequence
<220> FEATURE:
<223> OTHER INFORMATION: Amplification primer

<400> SEQUENCE: 27
gcaacgagaa ggccgtcgaa ct                                            22

<210> SEQ ID NO 28
<211> LENGTH: 22
<212> TYPE: DNA
<213> ORGANISM: Artificial sequence
<220> FEATURE:
<223> OTHER INFORMATION: Amplification primer

<400> SEQUENCE: 28
gtcctcgatg atcttcctga ca                                            22

<210> SEQ ID NO 29
<211> LENGTH: 20
<212> TYPE: DNA
<213> ORGANISM: Artificial sequence
<220> FEATURE:
<223> OTHER INFORMATION: Amplification primer

<400> SEQUENCE: 29
gcgtggcggt gttgtcggta                                               20

<210> SEQ ID NO 30
<211> LENGTH: 20
<212> TYPE: DNA
<213> ORGANISM: Artificial sequence
<220> FEATURE:
<223> OTHER INFORMATION: Amplification primer

<400> SEQUENCE: 30
gaccagttgt tcgcggctct                                               20

<210> SEQ ID NO 31
<211> LENGTH: 25
<212> TYPE: PRT
<213> ORGANISM: Mycobacterium smegmatis
```
ggaagcttgt tatccgtgcc agccagcgcg                                    30

-continued

```
<400> SEQUENCE: 31

Met Tyr Val Cys Gly Ile Thr Pro Tyr Asp Ala Thr His Leu Gly His
1               5                   10                  15

Ala Ala Thr Tyr Leu Thr Phe Asp Leu
            20                  25

<210> SEQ ID NO 32
<211> LENGTH: 27
<212> TYPE: PRT
<213> ORGANISM: Mycobacterium leprae

<400> SEQUENCE: 32

Ala Thr Met Tyr Val Cys Gly Ile Thr Pro Tyr Asp Ala Thr His Leu
1               5                   10                  15

Gly His Ala Ala Thr Tyr Leu Ala Phe Asp Leu
            20                  25

<210> SEQ ID NO 33
<211> LENGTH: 25
<212> TYPE: PRT
<213> ORGANISM: Streptomyces coelicolor

<400> SEQUENCE: 33

Ile Tyr Val Cys Gly Ile Thr Pro Tyr Asp Ala Thr His Met Gly His
1               5                   10                  15

Ala Ala Thr Tyr Asn Ala Phe Asp Leu
            20                  25

<210> SEQ ID NO 34
<211> LENGTH: 25
<212> TYPE: PRT
<213> ORGANISM: Corynebacterium striatum

<400> SEQUENCE: 34

Met Tyr Val Cys Gly Ile Thr Pro Tyr Asp Ser Thr His Leu Gly His
1               5                   10                  15

Ala Ala Thr Tyr Leu Thr Phe Asp Leu
            20                  25

<210> SEQ ID NO 35
<211> LENGTH: 25
<212> TYPE: PRT
<213> ORGANISM: Thermomonospora fusca

<400> SEQUENCE: 35

Met Tyr Val Cys Gly Ile Thr Pro Tyr Asp Ala Ala His Leu Gly His
1               5                   10                  15

Ala Phe Thr Tyr Leu Thr Phe Asp Leu
            20                  25

<210> SEQ ID NO 36
<211> LENGTH: 25
<212> TYPE: PRT
<213> ORGANISM: Mycobacterium tuberculosis

<400> SEQUENCE: 36

Ile Tyr Leu Cys Gly Ala Thr Val Gln Gly Leu Pro His Ile Gly His
1               5                   10                  15

Val Arg Ser Gly Val Ala Phe Asp Ile
            20                  25
```

```
<210> SEQ ID NO 37
<211> LENGTH: 25
<212> TYPE: PRT
<213> ORGANISM: Escherichia coli

<400> SEQUENCE: 37

Met Tyr Val Cys Gly Ile Thr Val Tyr Asp Leu Cys His Ile Gly His
1               5                   10                  15

Gly Arg Thr Phe Val Ala Phe Asp Val
            20                  25

<210> SEQ ID NO 38
<211> LENGTH: 76
<212> TYPE: PRT
<213> ORGANISM: Mycobacterium smegmatis

<400> SEQUENCE: 38

Ser Pro Phe Gly Arg Gly Arg Pro Gly Trp His Val Glu Cys Ser Ala
1               5                   10                  15

Ile Ala Leu Thr Arg Ile Gly Thr Gly Leu Asp Ile Gln Gly Gly Gly
            20                  25                  30

Ser Asp Leu Ile Phe Pro His His Glu Tyr Ser Ala Ala His Ala Glu
        35                  40                  45

Ser Val Thr Gly Glu Arg Arg Phe Ala Arg His Tyr Val His Thr Gly
    50                  55                  60

Met Ile Gly Trp Asp Gly His Lys Met Ser Lys Ser
65                  70                  75

<210> SEQ ID NO 39
<211> LENGTH: 76
<212> TYPE: PRT
<213> ORGANISM: Mycobacterium leprae

<400> SEQUENCE: 39

Ser Pro Phe Gly Pro Gly Arg Pro Gly Trp His Val Glu Cys Ala Ala
1               5                   10                  15

Ile Ala Leu Ser Arg Ile Gly Ile Gly Leu Asp Ile Gln Gly Gly Gly
            20                  25                  30

Ser Asp Leu Ile Phe Pro His His Glu Phe Thr Ala Ala His Ala Glu
        35                  40                  45

Cys Val Arg Gly Glu Arg Arg Phe Ala Arg His Tyr Val His Ala Gly
    50                  55                  60

Met Ile Gly Trp Asp Glu His Lys Met Ser Lys Ser
65                  70                  75

<210> SEQ ID NO 40
<211> LENGTH: 76
<212> TYPE: PRT
<213> ORGANISM: Streptomyces coelicolor

<400> SEQUENCE: 40

Gly Thr Leu Gly Arg Gly Arg Pro Gly Trp His Ile Glu Cys Val Ala
1               5                   10                  15

Ile Ala Leu Asp His Leu Gly Met Gly Phe Asp Val Gln Gly Gly Gly
            20                  25                  30

Ser Asp Leu Ala Phe Pro His His Glu Met Gly Ala Ser His Ala Gln
        35                  40                  45

Ala Leu Thr Gly Glu Phe Pro Met Ala Lys Ala Tyr Val His Ala Gly
    50                  55                  60
```

```
Met Val Gly Leu Asp Gly Glu Lys Met Ser Lys Ser
65                  70                  75

<210> SEQ ID NO 41
<211> LENGTH: 76
<212> TYPE: PRT
<213> ORGANISM: Corynebacterium striatum

<400> SEQUENCE: 41

Ser Pro Phe Gly Pro Gly Arg Pro Gly Trp His Val Glu Cys Ser Ala
1               5                   10                  15

Ile Ala Thr Asn Arg Leu Gly Ser His Phe Ala Ile Gln Gly Gly Gly
                20                  25                  30

Ser Asp Leu Ala Phe Pro His His Glu Phe Ser Ala Ala His Ala Glu
            35                  40                  45

Ala Ala Leu Lys Val Glu Arg Met Ala Gly His Tyr Val His Ala Gly
        50                  55                  60

Met Ile Ala Leu Asp Gly Val Lys Met Ser Lys Ser
65                  70                  75

<210> SEQ ID NO 42
<211> LENGTH: 76
<212> TYPE: PRT
<213> ORGANISM: Thermomonospora fusca

<400> SEQUENCE: 42

Thr Pro Leu Gly Arg Gly Arg Pro Gly Trp His Val Glu Cys Ser Ala
1               5                   10                  15

Ile Ser Val His Glu Leu Gly Met Gly Phe Asp Leu Asn Gly Gly Gly
                20                  25                  30

Asp Asp Leu Ile Phe Pro His His Glu Met Gly Ala Ala Glu Ala Cys
            35                  40                  45

Cys Ala Thr Gly Ser Arg Pro Gln Ala Arg His Tyr Leu His Val Ala
        50                  55                  60

Met Val Gly Leu Asp Gly Glu Lys Met Ser Lys Ser
65                  70                  75

<210> SEQ ID NO 43
<211> LENGTH: 74
<212> TYPE: PRT
<213> ORGANISM: Mycobacterium tuberculosis

<400> SEQUENCE: 43

Thr Pro Trp Gly Arg Gly Arg Pro Gly Trp His Leu Glu Cys Ser Ala
1               5                   10                  15

Met Ala Arg Ser Tyr Leu Gly Pro Glu Phe Asp Ile His Cys Gly Gly
                20                  25                  30

Met Asp Leu Val Phe Pro His His Glu Asn Glu Ile Ala Gln Ser Arg
            35                  40                  45

Ala Ala Gly Asp Gly Phe Ala Arg Tyr Trp Leu His Asn Gly Trp Val
        50                  55                  60

Thr Met Gly Gly Glu Lys Met Ser Lys Ser
65                  70

<210> SEQ ID NO 44
<211> LENGTH: 74
<212> TYPE: PRT
<213> ORGANISM: Escherichia coli
```

<400> SEQUENCE: 44

Pro Trp Gly Ala Gly Arg Pro Gly Trp His Ile Glu Cys Ser Ala Met
1               5                   10                  15

Asn Cys Lys Gln Leu Gly Asn His Phe Asp Ile His Gly Gly Ser
            20                  25                  30

Asp Leu Met Phe Pro His His Glu Asn Glu Ile Ala Gln Ser Thr Cys
        35                  40                  45

Ala His Asp Gly Gln Tyr Val Asn Tyr Trp Met His Ser Gly Met Val
    50                  55                  60

Met Val Asp Arg Glu Lys Met Ser Lys Ser
65                  70

<210> SEQ ID NO 45
<211> LENGTH: 24
<212> TYPE: DNA
<213> ORGANISM: Artificial sequence
<220> FEATURE:
<223> OTHER INFORMATION: Forward primer

<400> SEQUENCE: 45
tcccccggga cgcgtggcgc tgat                                      24

<210> SEQ ID NO 46
<211> LENGTH: 29
<212> TYPE: DNA
<213> ORGANISM: Artificial sequence
<220> FEATURE:
<223> OTHER INFORMATION: Reverse primer

<400> SEQUENCE: 46
ggactagtct acaggtccac cccgagcag                                 29

<210> SEQ ID NO 47
<211> LENGTH: 4
<212> TYPE: PRT
<213> ORGANISM: Thermomonospora fusca

<400> SEQUENCE: 47

His Gly Leu His
1

<210> SEQ ID NO 48
<211> LENGTH: 538
<212> TYPE: DNA
<213> ORGANISM: Mycobacterium smegmatis

<400> SEQUENCE: 48
gtgacctcca ccgagtggcg caccgggctc acgggtgccc agcaggcaga gattcgcgcg    60
ctgatcgacg cggccaccac gcacgacggt gtcgcgccgg tcggtgacca agtgctgcgg   120
gaactgggac gcgaccgcac ccggcacctg ctgaccaccg acgaccgcg cgtggtcgga   180 tacctcaacc tcgcgcctgc cgaggggac gatccggcga tggccgaact cgtcgtgcat   240
ccgcaggccc gccggcgcgg tatcggtgcg gccatggcgc gcaccgcgct ggcagagggc   300
gggccgggcg cccgtatctg ggcgcacggc aacatcgccg ccgcccaggc gatggcgtca   360
tcgcttcgcc tggtggtggt gcgtgagctg ctgcagatgc cgcccct gaccgatctg   420 ccgccggtgc cggacacccc cggcgtgcgc atcgcgacct acgccggccc cggcgacgac   480
gccgagatcc tgcgggtcaa caacgccgcg ttctcgtggc accccgagca gggcgtga     538

```
<210> SEQ ID NO 49
<211> LENGTH: 1305
<212> TYPE: DNA
<213> ORGANISM: Mycobacterium smegmatis

<400> SEQUENCE: 49
gtgcgtctag cgacagacct cgagaccccc cgccgcgtgg cggtgttgtc ggtacacacc      60
tctccgctgg cgcagccggg caccggcgac gcgggcggca tgaacgtcta cgtgttgcag     120
accgcgctgc aactggcccg gcgtggcgtc gaggtcgagg tcttcaccag ggccacgtcg     180
tcggccgatg cgccggtcgt gcctgtggcg cccggtgtgc tggtgcgcaa cgtcgtggcc     240
ggcccgttcg aaggcctcga caagaacgat ctgcccacgc agctgtgcgc gttcaccgcg     300
ggtgtgctgc gcgccgaggc gacccacgag cccggctact acgacgtcgt gcattcgcac     360
tactggctgt ccggccaggt cgggtggctg gcgcgcgacc gctgggccgt gccgctggtg     420
cacaccgcgc acacgctggc cgcggtcaag aacgccgcac tcgccgcggg cgacgcaccc     480
gagccgccgc tgcgcgcggt gggcgaacaa caggtggtcg acgaggccga ccgcctcatc     540
gtgaacaccg aagtcgaagc gcagcaactg gtctcgttgc acaatgccga ccgctcacgc     600
atcgacgtcg tgcaccccgg cgtcgatctc gacgtgttca cccccggttc gcgcgacgcg     660
gcgcgcgcgc tgttcgggct tcccaccgac cagaagatcg tggcgttcgt gggccgcatc     720
cagccgctca aggcccccga catcctgctg cgtgccgcgg cgaaactgcc cggcgtgcgc     780
gtgctgatcg ccggtggacc ctccggatcg ggacttgccc aaccggacac gctggttcgg     840
ctcgccgacg aactgggtat cagtgaccgg gtgacgttcc tcccgccgca gagccgcgaa     900
caactggtca acgtgtaccg ggcggccgat ctggtcgcgg tgccgagcta ctccgagtcg     960
ttcggcctgg tcgccgtcga ggcgcaggcg tgcggcacgc ccgtcgtcgc cgcggccgtc    1020
ggcggactgc cggtcgcggt ggccgacggc gtcagcgggg cactcgtcga cggccacgac    1080
atcggcgact gggccgacac catcagcgag gtgctcgacc gcgagcccgc cgcgctgagc    1140
cgcgcctccg ccgaacacgc cgctcagttc tcgtgggcgc acaccgtcga cgcgctgctc    1200
gccagctaca gccgggccat gagtgactac cgggcccgtc atcccagacc cgccgcgcgg    1260
cgttccggac gccggttctc gatgcgcagg ggagtacgca cgtga                    1305
```

METHODS OF USE OF THE ENZYMES OF MYCOTHIOL SYNTHESIS

The present application claims priority to U.S. Provisional Application Ser. No. 60/373,079, filed on Apr. 15, 2002 and U.S. Provisional Application Ser. No. 60/373,890, filed on Apr. 19, 2002. This application is a national stage entry of PCT/US03/1159, international filing date Apr. 15, 2003.

FIELD OF THE INVENTION

The invention relates generally to isolation and identification of three families of enzymatic compounds produced by bacteria and involved in the steps of mycothiol biosynthesis and, more specifically, to identification of MshC, MshD and MshA and methods of use thereof, especially for use in drug discovery and disease control.

BACKGROUND INFORMATION

Glutathione (GSH) is the dominant low molecular weight thiol in most eukaryotes and Gram-negative bacteria, and it plays a key role in protection of the cell against oxygen toxicity and electrophilic toxins. However, most gram-positive bacteria, including many strict aerobes, do not produce glutathione. Yet aerobic organisms are subjected to oxidative stress from many sources, including atmospheric oxygen, basal metabolic activities, and, in the case of pathogenic microorganisms, toxic oxidants from the host phagocytic response intended to destroy the bacterial invader.

Actinomycetes, including *Streptomyces* and *Mycobacterium*, do not make GSH but produce instead millimolar levels of mycothiol (MSH, AcCys-GlcN-Ins), an unusual conjugate of N-acetylcysteine (AcCys) with 1D-myo-inosityl 2-amino-2-deoxy-$\alpha$-D-glucopyranoside (GlcN-Ins). The biochemistry of mycothiol appears to have evolved completely independently of that of glutathione. However, it has already been established that the metabolism of mycothiol parallels that of glutathione metabolism in several enzymatic processes. First, formaldehyde is detoxified in glutathione-producing organisms by NAD/glutathione-dependent formaldehyde dehydrogenase (L. Uotila, et al. (1989) in *Glutathione: Chemical, Biochemical, and Medical Aspects—Part A* (D. Dolphin, et al., Eds.) pp 517-551, John Wiley & Sons, et al.). An analogous process involving NAD/mycothiol-dependent formaldehyde dehydrogenase has been identified in the actinomycete *Amycolatopsis methanolica* (M. Misset-Smits, et al. (1997) *FEBS Lett.* 409:221-222). This enzyme has been sequenced (A. Norin, et al. (1997) *Eur. J. Biochem.* 248:282-289).

The second enzymatic process involves a mycothiol homolog of glutathione reductase recently cloned from *M. tuberculosis* and expressed in *M. smegmatis* (M. P. Patel, et al. (1999) *J. Amer. Chem. Soc.* 120:11538-11539; M. P. Patel et al. (1999) *Biochemistry* 38:11827-11833; M. P. Patel et al (2001) *Biochemistry* 40:3119-3126). The reductase is reasonably specific for the disulfide of mycothiol, but is also active with the disulfide of AcCys-GlcN, the desmyo-inositol derivative of mycothiol.

A general mycothiol-dependent detoxification process has been described in *M. smegmatis* in which MSH forms S-conjugates (MSR) with reactive electrophiles, including some antibiotics, and MSR is subsequently degraded by the enzyme mycothiol S-conjugate amidase to produce GlcN-Ins and AcCySR, a mercapturic acid, which is excreted from the cell; in MSR R is derived from the electrophile (Newton, et al. (2000) Biochemistry 39:10739-10746).

The biosynthesis of MSH has been identified as involving four steps: (1) formation of GlcNAc-Ins; (2) deacetylation of GlcNAc-Ins to produce GleN-Ins; (3) ligation of GleN-Ins to Cys to produce Cys-GlcN-Ins; (4) acetylation of Cys-GlcN-Ins by acetyl-CoA to produce MSH (Bornemann, et al. (1997) Biochem. J. 325:623-629; Anderberg, et al. (1998) J. Biol. Chem. 273:30391-7; Newton, et al. (2000) J. Bacteriol. 182: 6958-6963). The genes encoding these biosynthesis steps have been designated mshA, mshB, mshC, and mshD but the only biosynthetic gene identified thus far is the mshB gene encoding the deacetylase MshB (Newton, et al. (2000) J. Bacteriol. 182:6958-6963).

The structure of mycothiol, 1-D-myo-inosityl 2-(N-acetyl-L-cysteinyl)amido-2-deoxy-$\alpha$-D-glucopyranoside (AcCys-GlcN-Ins), makes it resistant to heavy-metal-catalyzed autoxidation (Newton et al. 1995) and it appears to have functions analogous to those of glutathione. A mycothiol-dependent formaldehyde dehydrogenase has been identified (Misset-Smits et al. 1997; Norin et al. 1997). *Mycobacterium smegmatis* mutants defective in MSH biosynthesis exhibit enhanced sensitivity to hydrogen peroxide and modified sensitivity to antibiotics (Newton et al. 1999). Alkylating agents are detoxified by mycothiol and the resulting S-conjugates cleaved by an amidase to produce the N-acetylcysteine derivative (mercapturic acid), which is excreted from the cell (Newton et al. 2000b). A mycothiol disulfide reductase maintains mycothiol in the reduced state (Patel and Blanchard 1999; Patel and Blanchard 2001).

Therefore, there is a need in the art for methods and compounds useful for investigation of the details of the metabolism of mycothiol and comparison with the established roles for the metabolism of glutathione and for identification of as yet unidentified biosynthesis genes.

Antibiotic resistance of pathogenic bacteria, including pathogenic actinomycetes, such as *M. tuberculosis*, is a well-known problem faced by medical practitioners in treatment of bacterial diseases. Therefore, there is a need in the art for new antibiotics, drugs and vaccines and for screening techniques to discover antibiotics, drugs and vaccines effective to treat or prevent bacterial infections in humans and in other mammals, such as domestic and farm animals.

SUMMARY OF THE INVENTION

The present invention relates to isolation and characterization of MshC, MshD and MshA, enzymes involved in the mycothiol biosynthesis pathway and provides methods utilizing such enzymes.

In one embodiment, the invention provides a method for identifying an inhibitor of cysteine:glucosaminyl inositol ligase (MshC). The method includes contacting a candidate compound with a cysteine:glucosaminyl inositol ligase in the presence of cysteine and a glucosaminyl inositol or a derivative thereof, under suitable conditions, and determining the presence or absence of ligation of the cysteine to the glucosaminyl inositol or derivative thereof. In the embodiment of the invention, a substantial absence of the ligation is indicative of a candidate compound that inhibits activity of the ligase. In another embodiment, the invention provides an inhibitor identified by the method.

In yet another embodiment, the invention provides a method for decreasing the virulence of a pathogenic cysteine: glucosaminyl inositol ligase-producing bacterium in mammalian cells. The method includes introducing an inhibitor of cysteine:glucosaminyl inositol ligase activity into the bacterium and observing the effect on the activity of the ligase. Where the intracellular presence of the inhibitor decreases activity of the ligase, mycothiol biosynthesis by the bacterium is also decreased, as compared with untreated control bacterium.

In still another embodiment, the invention provides a method for increasing sensitivity of a pathogenic cysteine:glucosaminyl inositol ligase-producing bacterium in mammalian cells to an antibiotic. The method includes introducing an inhibitor of cysteine:glucosaminyl inositol ligase activity into the bacterium. The intracellular presence of the inhibitor decreases activity of the ligase, thereby decreasing mycothiol biosynthesis by the bacterium in said mammalian cells as compared with untreated control bacterium so as to increase sensitivity of the bacterium to an antibiotic.

The invention also provides a method for inhibiting growth of a glucosaminyl inositol-producing bacterium in a mammal. The method includes administering an effective amount of an inhibitor of intracellular cysteine:glucosaminyl inositol ligase to the mammal, thereby inhibiting growth of the bacterium in the mammal.

The invention also provides an inhibitor of cysteine:glucosaminyl inositol ligase, where the inhibitor is derived from L-cysteine by replacing the carboxyl group with a moiety that binds the enzyme active site.

In another embodiment, the invention provides a method for identifying an inhibitor of acetyl-CoA:cysteinyl glucosaminyl inositol (acetyl-CoA:Cys-GlcN-Ins) acetyltransferase (MshD). The method includes contacting a candidate compound with an acetyl-CoA:Cys-GlcN-Ins acetyltransferase in the presence of an acetyl-CoA and cysteinyl glucosaminyl inositol (Cys-GlcN-Ins) or a derivative thereof, under suitable conditions and determining the presence or absence of a transfer of acetyl to the Cys-GlcN-Ins or a derivative thereof. In the embodiment of the invention, the substantial absence of a transfer of acetyl is indicative of a candidate compound that inhibits activity of the acetyltransferase. In another embodiment, the invention provides an inhibitor identified by the method.

The invention also provides a method for decreasing the virulence of a pathogenic acetyl-CoA:Cys-GlcN-Ins acetyltransferase-producing bacterium in mammalian cells. The method includes introducing an inhibitor of acetyl-CoA:Cys-GlcN-Ins acetyltransferase activity into the bacterium, where the intracellular presence of the inhibitor decreases activity of the acetyltransferase. Such a decrease also decreases mycothiol biosynthesis by the bacterium as compared with untreated control bacterium.

In another embodiment, the invention provides a method for increasing sensitivity of a pathogenic acetyl-CoA:Cys-GlcN-Ins acetyltransferase-producing bacterium in mammalian cells to an antibiotic. The method includes introducing an inhibitor of endogenous bacterial acetyltransferase activity into the bacterium, where the intracellular presence of the inhibitor decreases activity of the acetyltransferase. Such a decrease in activity also decreases mycothiol biosynthesis by the bacterium in said mammalian cells as compared with untreated control bacterium so as to increase sensitivity of the bacterium to an antibiotic.

In still another embodiment, the invention provides a method for inhibiting growth of an acetyl-CoA:Cys-GlcN-Ins-producing bacterium in a mammal. The method includes administering to the mammal an effective amount of an inhibitor of intracellular acetyl-CoA:Cys-GlcN-Ins acetyltransferase, thereby inhibiting growth of the bacterium in the mammal.

In yet another embodiment, the invention provides a method for identifying an inhibitor of MshA glycosyltransferase (MshA). The method includes contacting a candidate compound with a mycothiol-producing bacterium under suitable conditions, and determining the presence or absence of 1D-myo-inosityl 2-acetamido-2-deoxy-α-D-glucopyranoside (GlcNAc-Ins) within the mycothiol-producing bacterium. A substantial absence of GlcNAc-Ins within the bacterium is indicative of a compound that inhibits activity of the glycosyltransferase. In another embodiment, the invention provides an inhibitor identified by the method.

In another embodiment, the invention provides a method for decreasing the virulence of a pathogenic MshA glycosyltransferase-producing bacterium in mammalian cells. The method includes introducing an inhibitor of MshA glycosyltransferase activity into the bacterium. The intracellular presence of the inhibitor decreases activity of the glycosyltransferase, thereby decreasing mycothiol biosynthesis by the bacterium as compared with untreated control bacterium.

In still another embodiment, the invention provides a method for increasing sensitivity of a pathogenic MshA glycosyltransferase-producing bacterium in mammalian cells to an antibiotic. The method includes introducing an inhibitor of endogenous bacterial glycosyltransferase activity into the bacterium. The intracellular presence of the inhibitor in the method if the invention decreases activity of the MshA glycosyltransferase and thereby decreasing mycothiol biosynthesis by the bacterium in said mammalian cells as compared with untreated control bacterium. The decrease in mycothiol biosynthesis increases sensitivity of the bacterium to an antibiotic.

The invention also provides a method for inhibiting growth of a GlcNAc-Ins-producing bacterium in a mammal. The method includes administering an effective amount of an inhibitor of intracellular MshA glycosyltransferase to the mammal. Such administration inhibits growth of the bacterium in the mammal.

In yet another embodiment, the invention provides a method for identifying an inhibitor of mycothiol biosynthesis. The method includes contacting a candidate compound for inhibition of MshC, MshD or MshA or a combination thereof with a mycothiol-producing bacterium under suitable conditions, and determining the presence or absence of mycothiol within the bacterium. A substantial absence of mycothiol within the bacterium is indicative of a compound that inhibits activity of the MshC, MshD or MshA and therefore inhibits mycothiol biosynthesis. In another embodiment, the invention provides an inhibitor identified by the method.

In yet another embodiment, the invention provides a method for increasing sensitivity of a pathogenic mycothiol-producing bacterium in mammalian cells to an antibiotic. The method includes introducing an inhibitor of endogenous bacterial mycothiol biosynthesis into the bacterium. The intracellular presence of the inhibitor decreases mycothiol biosynthesis by the bacterium in the mammalian cells as compared with untreated control bacterium so as to increase sensitivity of the bacterium to an antibiotic.

In another embodiment, the invention provides a live mutant actinomycete, whose genome comprises a disruption in an endogenous gene or genes encoding a mycothiol biosynthesis enzyme. The mycothiol biosynthesis enzyme gene is selected from mshC, mshD or mshA. The disruption prevents function of an mycothiol biosynthesis enzyme while cell surface proteins and lipids are substantially unaffected, and wherein said disruption results in said mutant actinomycetes exhibiting transient survival in mammalian white blood cells for an immune response-raising period of time.

In still another embodiment, the invention provides a purified cysteine:glucosaminyl inositol ligase with an amino acid sequence with 35% or more sequence identity to SEQ ID NO:

2 or conservative variations thereof, and which has cysteine: glucosaminyl inositol ligase activity.

The invention also provides a purified acetyl-CoA:Cys-GlcN-Ins acetyltransferase with an amino acid sequence with 35% or more sequence identity to SEQ ID NO: 15 or conservative variations thereof, and which has acetyl-CoA:Cys-GlcN-Ins acetyltransferase activity.

In yet another embodiment, the invention provides a purified MshA glycosyltransferase with an amino acid sequence with 35% or more sequence identity to SEQ ID NO: 19, and conservative variations thereof, and which has MshA glycosyltransferase activity.

In still another embodiment, the invention provides an expression vector comprising polynucleotides of mshA, mshB, mshC and mshD. In the expression vector, the polynucleotide of mshA is SEQ ID NO: 49, the polynucleotide of mshC is SEQ ID NO: 1 and the polynucleotide of mshC is SEQ ID NO: 48.

In another embodiment, the invention provides a method for identifying an inhibitor of cysteine:glucosaminyl inositol ligase (MshC). The method includes contacting a candidate compound with a cysteine:glucosaminyl inositol ligase in the presence of a cysteine; a glucosaminyl inositol or a derivative thereof and ATP, under suitable conditions, and assaying for the generation of pyrophosphate. The substantial absence of pyrophosphate, as determined by the assay, is indicative of a candidate compound that inhibits activity of the ligase.

BRIEF DESCRIPTION OF THE DRAWINGS

FIG. 2A shows the nucleotide sequence of mshC of *M. smegmatis* (SEQ ID NO: 1). FIG. 2B shows the corresponding deduced amino acid sequence (SEQ ID NO: 2) of SEQ ID NO: 1. FIG. 2C shows the nucleotide sequence of mshC of *M. tuberculosis* (Rv 2130c) (Tuberculist database) (SEQ ID NO: 3) and FIG. 2D shows the corresponding deduced amino acid sequence (SEQ ID NO: 4) of SEQ ID NO: 3. FIG. 2E shows the amino acid sequence of MshC of *Corynebacterium striatum* (SEQ ID NO:5), and FIG. 2F shows the amino acid sequence of MshC of *Streptomyces coelicolor* (SEQ ID NO:6).

FIG. 3A shows the chromatographic profile of DEAE ion exchange; FIG. 3B shows the chromatographic profile of the hydroxyl apatite column; FIG. 3C shows the chromatographic profile of Reactive Brown 10 affinity chromatography; and FIG. 3D shows the chromatographic profile of Sephadex G-100 gel filtration.

FIG. 4 shows an alignment of the amino acid sequences of orthologs of MshC. Row 1 shows MshC of *M. smegmatis* (SEQ ID NO: 2) (nucleic acids 1222384-1223620 of unfinished *M. smegmatis* genomic sequence (TIGR)); Row 2 shows the ortholog of *M. tuberculosis* (Rv2130c) (Tuberculist database) (SEQ ID NO: 4; Row 3 shows the ortholog of *C. striatum* (SEQ ID NO: 5) (GenBank Accession # AAG03366); and Row 4 shows the ortholog of *S. coelicolor* (GenBank Accession No. CAC 36366) (SEQ ID NO: 6).

FIG. 5 shows an alignment of the amino acid sequences of MshC (Row 1) (SEQ ID NO:2) with CysS of *M. tuberculosis* (Row 2)(Rv3580c, GenBank Accession #NP_218097) (SEQ ID NO: 12) and CysS of *E. coli* (Row 3)(GenBank Accession #NP_308615) (SEQ ID NO: 13).

FIG. 8 shows an alignment of mycothiol synthase (MshD) from *M. tuberculosis* (SEQ ID NO: 14), *M. smegmatis* (SEQ ID NO: 15), *M. leprae* (SEQ ID NO: 16), *S. coelicolor* A(3)2 (SEQ ID NO: 17), and *C. diphtheriae* (SEQ ID NO: 18); "- - - pfam00583 - - -" denotes two regions with similarity to the acetyltransferase consensus domain.

FIG. 10A shows the amino acid sequence of MshD of *M. tuberculosis* (Rv0819) (SEQ ID NO: 14); FIG. 10B shows the amino acid sequence of MshD of *M. smegmatis* (SEQ ID NO: 15); FIG. 10C shows the amino acid sequence of MshD of *M. leprae* (SEQ ID NO: 16); FIG. 10D shows the amino acid sequence of MshD of *S. coelicolor* (SEQ ID NO: 17); FIG. 10E shows the amino acid sequence of MshD of *C. diphtheriae* (SEQ ID NO: 18); and FIG. 10F shows the nucleic acid sequence of MshD of *M. smegmatis* (SEQ ID NO: 48).

FIG. 11 shows a sequence alignment for MshA from *M. smegmatis* (SEQ ID NO: 19) and *M. tuberculosis* (SEQ ID NO: 20), with SpsA from *Anaebaena* sp. PCC7120 (SEQ ID NO: 21), and PimB (Rv0557) from *M. tuberculosis* (SEQ ID NO: 22). Site of the G32D mutation in *M. smegmatis* mutant 49 is denoted by *. Numbering refers to the *M. tuberculosis* MshA sequence.

FIG. 12A shows the amino acid sequence of MshA of *M. smegmatis* (SEQ ID NO: 19); FIG. 12B shows the amino acid sequence of MshA of *M. tuberculosis* (SEQ ID NO: 20); and FIG. 12C shows the nucleic acid sequence of MshA of *M. smegmatis* (SEQ ID NO: 49).

FIG. 18 shows the sequence alignments of the a) First half of the Rossman fold of *M. smegmatis* MshC (SEQ ID NO: 31), *M. leprae* MshC (SEQ ID NO: 32), *S. coelicolor* MshC (SEQ ID NO: 33), *C. striatum* MshC (SEQ ID NO: 34), *T. fusca* MshC (SEQ ID NO: 35), *M. tuberculosis* CysS (SEQ ID NO: 36) and *E. coli* CysS (SEQ ID NO: 37) and b) Second half of the Rossman fold of *M. smegmatis* MshC (SEQ ID NO: 38), *M. leprae* MshC (SEQ ID NO: 39), *S. coelicolor* MshC (SEQ ID NO: 40), *C. striatum* MshC (SEQ ID NO: 41), *T. fusca* MshC (SEQ ID NO: 42), *M. tuberculosis* CysS (SEQ ID NO: 43) and *E. coli* CysS (SEQ ID NO: 44), orthologs of MshC with conserved Zn binding residues.

DETAILED DESCRIPTION OF THE INVENTION

Figure 1:
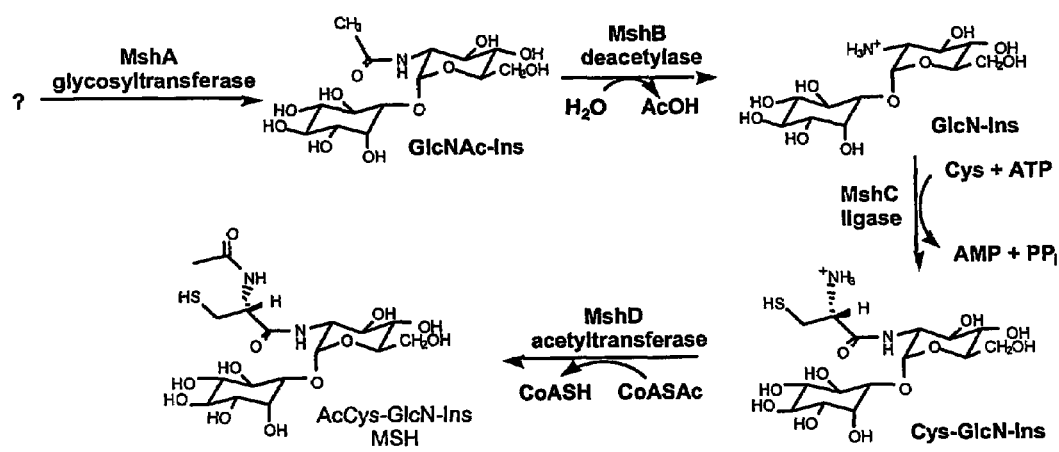
FIG. 1 is a schematic representation of the biosynthesis pathway for mycothiol.

Mycothiol (1D-myo-inosityl 2-(N-acetylcysteinyl)amido-2-deoxy-α-D-glucopyranoside) (MSH) is present in a variety of actinomycetes and plays an essential role in a pathway of detoxification in such bacteria Mycothiol is comprised of N-acetylcysteine (AcCys) amide linked to 1D-myo-inosityl 2-amino-2-deoxy-α-D-glucopyranoside (GlcN-Ins) and is the major thiol produced by most actinomycetes. In the mycothiol-dependent detoxification process in actinomycetes, an alkylating agent is converted to a S-conjugate of mycothiol, the latter is cleaved to release a mercapturic acid, and the mercapturic acid is excreted from the cell (Newton et al. (2000a) *Biochemistry* 39:10739-10746).

Stopping the production of MSH should eliminate the MSH-dependent protective mechanisms and this makes the enzymes of mycothiol biosynthesis of special interest. The pathway of mycothiol biosynthesis involves at least four enzymes, as set forth in FIG. 1. These enzymes are designated MshA, MshB, MshC and MshD. By the present invention, three of the four enzymes were isolated and identified and utilization of the identified sequences in methods of drug discovery and disease control are provided. MshB was previously identified and disclosed in U.S. application Ser. No. 10/297,512, filed Dec. 6, 2002, hereby incorporated by reference in its entirety, which is a national stage application of PCT/JS01/19091, filed Jun. 14, 2001, which claims priority to U.S. Provisional Application 60/211,612, filed Jun. 14, 2000.

A family of purified cysteine:glucosaminyl inositol ligase (MshC) polypeptides with catalytic ligase activity for glucosaminyl inositol (1D-myo-inosityl 2-amino-2-deoxy-α-Dglucopyranoside; GlcN-Ins) and cysteine or a cysteine derivative is provided. The cysteine:glucosaminyl inositol ligases are characterized by having an amino acid sequence with 35% or more homology to SEQ ID NO: 2, for example 35% 40%, 45%, 50%, 55%, 60%, 65%, 70%, 75%, 80%, 85%, 90%, 95% or 100% identity thereto, and by having cysteine:glucosaminyl inositol ligase activity. The members of the family of ligases catalyze ligation of cysteine to a glucosaminyl inositol or a derivative thereof. For example, the ligase catalyzes ATP-dependent ligation of L-cysteine to 1D-myo-inosityl 2-amino-2-deoxy-α-D-glucopyranoside. In one embodiment, the glucosaminyl inositol is a precursor of mycothiol (e.g., in a mycothiol producing bacterium).

In one embodiment the ligase has an amino acid sequence as set forth in SEQ ID NO: 2, SEQ ID NO: 4, SEQ ID NO: 5 or SEQ ID NO: 6 and catalyzes ligation of cysteine to a glucosaminyl inositol or a derivative thereof, especially ATP-dependent ligation of the cysteine to a glucosaminyl inositol or a derivative thereof. In one embodiment the glucosaminyl inositol or derivative to be ligated to the cysteine by the ligases is 1D-myo-inosityl 2-amino-2-deoxy-α-D-glucopyranoside (GlcN-Ins). The ligase may be encoded by a polynucleotide comprising a nucleic acid sequence as set forth in SEQ ID NO: 1.

As used herein, the term "glucosaminyl inositol derivative" means 1L- or 1D-myo-inosityl 2-amino-2-deoxy-α-D-glucopyranoside, as well as 2-amino-2-deoxy-α-D-glucopyranosides derived from alcohols other than 1D-myo-inosityl.

As used herein, the term "cysteine" means the L-isomer of cysteine.

Additionally, there is provided a family of purified acetyl-CoA:cysteinyl glucosaminyl inositol (acetyl-CoA:Cys-GlcN-Ins) acetyltransferase (MshD) polypeptides with acetyltransferase activity for cysteinyl glucosaminyl inositol and acetyl-CoA. The acetyl-CoA:Cys-GlcN-Ins acetyltransferases are characterized by having an amino acid sequence with 35% or more homology to SEQ ID NO: 15, for example 35%, 40%, 45%, 50%, 55%, 60%, 65%, 70%, 75%, 80%, 85%, 90%, 95% or 100% identity thereto, and by having acetyltransferase activity. The members of the family of acetyltransferases catalyze transfer of an acetyl group to a Cys-GlcN-Ins or derivative thereof, resulting in the production of mycothiol (AcCys-GlcN-Ins). The acetyltransferase may be encoded by a polynucleotide comprising a nucleic acid sequence as set forth in SEQ ID NO: 48.

Additionally, a family of purified MshA glycosyltransferase (MshA) polypeptides with glycosyltransferase activity is provided. The MshA glycosyltransferases are characterized by having an amino acid sequence with 35% or more homology to SEQ ID NO: 19, for example, 35%, 40%, 45%, 50%, 55%, 60%, 65%, 70%, 75%, 80%, 85%, 90%, 95% or 100% identity thereto, and by having glycosyltransferase activity. The members of the family of acetyltransferases catalyze production of 1D-myo-inosityl 2-acetamido-2-deoxy-α-D-glucopyranoside (GlcNAc-Ins). In one embodiment, the GlcNAc-Ins is a precursor of mycothiol (e.g., in a mycothiol producing bacterium). The glycosyltransferase may be encoded by a polynucleotide comprising a nucleic acid sequence as set forth in SEQ ID NO: 49.

The methods described herein further elaborate the pathway involved in MSH biosynthesis. The invention demonstrates that GlcNAc-Ins is an intracellular MSH component and is formed by activity of MshA. This conversion defines an initial step in mycothiol biosynthesis. Further, the invention demonstrates that GlcN-Ins is an intracellular MSH component in *M. smegmatis* and is converted to Cys-GlcN-Ins by Cys:GlcN-Ins ligase (MshC). This conversion defines the penultimate step in MSH biosynthesis. Additionally, the invention demonstrates that Cys-GlcN-Ins is a precursor to mycothiol and is converted to mycothiol by acetyl-CoA:Cys-GlcN-Ins acetyltransferase (MshD) activity. This conversion defines the final step in MSH biosynthesis.

Figure 4:
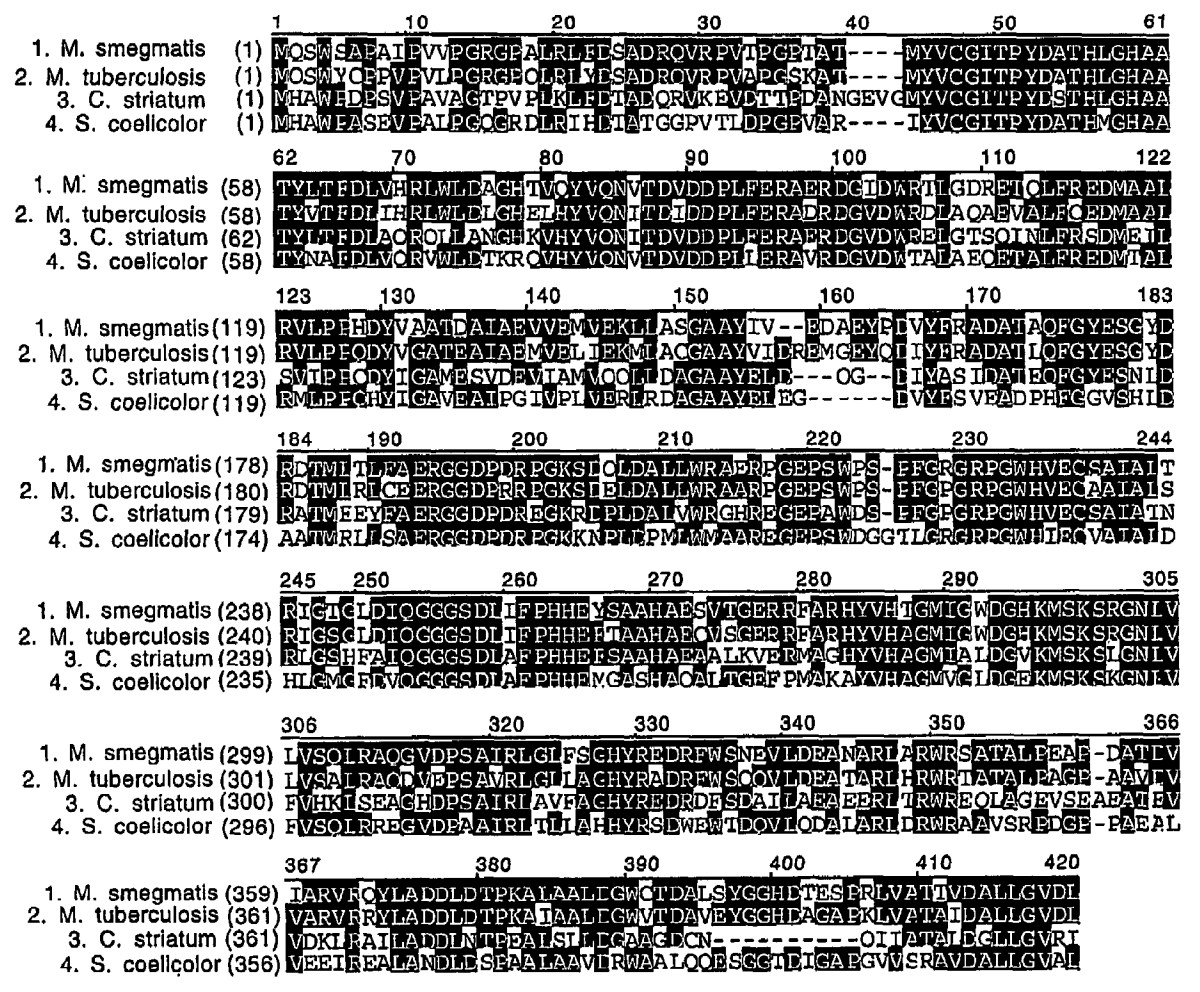

A member of the family of polypeptide ligases shown to be responsible for ATP-dependent ligation of L-cysteine to GlcN-Ins to form Cys-GlcN-Ins has been cloned from *M. tuberculosis* genomic sequence and corresponds to an open reading frame designated Rv2130c and misidentified as a probable cysS2, cysteinyl-tRNA synthetase (GenBank Accession # NP_216646) (Cole, et al. (1998) *Nature* 393: 537-544). The nucleic acid sequence encoding this protein corresponds to nucleic acids 2391213-2392457 of the *M. tuberculosis* genome encoding a protein of 414 amino acid residues. The derived amino acid sequence is as set forth in SEQ ID NO: 4. A BLAST search with the *M. tuberculosis* MshC sequence on GenBank revealed additional homologs in *Corynebacterium striatum* (Accession # AAG03366) (SEQ ID NO: 5) and *Streptomyces coelicolor* (Accession # CAC36366) (SEQ ID NO: 6). The sequences for these MshC proteins are included in FIG. 4 and have 54-58% identity to the *M. tuberculosis* and *M. smegmatis* sequences. Orthologs of *M. tuberculosis* MshC were also found at the Sanger Centre in *M. leprae* (82% identity, S. T. Cole et al. (2001) *Nature* 409, 1007), *M. bovis* (96% identity; website Sanger.org/Projects/M_bovis), and *Corynebacterium diphtheriae* (54% identity; website Sanger.org/Projects/C_diphtheriae), and at TIGR in *M. avium* (81% identity). All of these organisms belong to genera of bacteria that have been shown to produce MSH (Newton et al., (1996) *J. Bacteriol.* 178, 1990-1995). This sequence homology indicates that MSH biosynthesis in these organisms utilizes a GlcN-Ins ligase (MshC) in the same manner as that described here for *M. smegmatis*. Other actinomycetes that produce MSH are also expected to have a Cys:glcN-Ins ligase (MshC) gene homologous to SEQ ID NO: 1 or 3.

A member of the family of polypeptide acetyltransferases shown to be responsible for acetylation of Cys-GlcN-Ins to form mycothiol has been cloned from *M. tuberculosis* genomic sequence and corresponds to an open reading frame designated Rv0819. The nucleic acid sequence encoding this protein corresponds to nucleic acids 911736-912680 of the *M. tuberculosis* genome encoding a protein of 315 amino acid residues. The derived amino acid sequence is as set forth in SEQ ID NO: 14. Sequence searches with the *M. smegmatis* mshD gene revealed orthologs in other actinomycetes including *M. tuberculosis* H37Rv. The *M. tuberculosis* gene (Rv0819) was cloned, expressed in *E. coli*, and shown to code for mycothiol synthase activity. Other actinomycetes that produce MSH are also expected to have an acetyl-CoA:Cys-GlcN-Ins acetyltransferase (MshD) gene homologous to SEQ ID NO: 14 or 15.

A member of the family of polypeptide glycosyltransferases shown to be responsible for formation of GlcNAc-Ins has been cloned from *M. tuberculosis* genomic sequence and corresponds to an open reading frame designated Rv0486. The nucleic acid sequence encoding this protein corresponds to nucleic acids 575348-576787 of the *M. tuberculosis* genome encoding a protein of 480 amino acid residues. The derived amino acid sequence is as set forth in SEQ ID NO: 20. Other actinomycetes that produce MSH are also expected to have an MshA glycosyltransferase (MshA) gene homologous to SEQ ID NO: 19 or 20.

The enzyme families as set forth above are utilized in the methods of the invention.

Members of the mycothiol biosynthesis families of enzymes are formed in vivo by bacteria as part of a mycothiol biosynthesis pathway, most usually in bacteria characterized by intracellular production of mycothiol. Additional bacteria from which the mycothiol biosynthesis polypeptides can be obtained include *actinomycetes*, such as *M. smegmatis, M tuberculosis, M. leprae, M. bovis, M. intracellulare, M. africanum, M. marinarum, M. chelonai, Corynebacterium diphtheria, Actinomycetes israelii, M. avium* complex (MAC) (Holzman, in *Tuberculosis* ed. by Rom and Gary (Little, Brown, and Company, 1996) Chapter 56), *M. ulcerans, M. abscessus,* or *M. scrofulaceum,* and the like. *Actinomycetes* that can be used for this purpose include antibiotic-producing bacteria Homologous non-mycobacterial ligase proteins can also be obtained from the antibiotic producers *Streptomyces lincolnensis, Amycolatopsis mediterranei, Amycolatopsis orientalis, Streptomyces lavendulae, Streptomyces coelicolor, Streptomyces rochei,* the polyketide erythromycin antibiotic producer *Saccharopolyspora erythraea, Streptomyces violaceoruber* Tu7, *Streptomyces diastochromogens* subsp. *variabilicolor,* and *Streptomyces* sp. OM-6519.

Inhibitors of the mycothiol biosynthesis ligases, acetyltransferases and glycosyltransferases are particularly well suited as antibiotics against mycothiol-producing bacteria since mycothiol production will cease in the absence of the intermediate products, GlcNAc-Ins or Cys-GlcN-Ins, produced by activity of the mycothiol biosynthesis enzymes. Accordingly, in one embodiment of the present invention, there are provided methods for identifying an inhibitors of MshC, MshD, MshA and mycothiol biosynthesis.

In one embodiment, the invention provides a method for identifying an inhibitor of cysteine:glucosaminyl inositol ligase. The method includes contacting a candidate compound with a cysteine:glucosaminyl inositol ligase in the presence of cysteine and a glucosaminyl inositol or derivative thereof, under suitable conditions, and determining the presence or absence of ligation of cysteine to the glucosaminyl inositol or derivative thereof. For example, if the test compound is a putative inhibitor of ligase activity of the polypeptide ligase, the absence of ligated Cys-GlcN-Ins indicates the candidate compound is an inhibitor of the activity of the polypeptide as a ligase. Similarly, if the test compound is assayed as a putative inhibitor of MshC in mycothiol-producing bacteria, the presence of excess GlcN-Ins indicates that the candidate compound is an inhibitor of the activity of the ligase for linkage of cysteine or a cysteine derivative to a glucosaminyl inositol. On the other hand, in such assays, the presence of Cys-GlcN-Ins indicates that the test compound is not an inhibitor of MshC activity. In another embodiment, the candidate compound is contacted with a cysteine:glucosaminyl inositol ligase in the presence of cysteine, a glucosaminyl inositol or derivative thereof, ATP and pyrophosphatase, under suitable conditions, and detecting the resulting inorganic phosphate with a colorimetric or fluorometric assay known in the art.

In one embodiment, the cysteine:glucosaminyl inositol ligase of the method is characterized as having an amino acid sequence with 35% or more sequence identity to SEQ ID NO: 2 or 4, or conservative variations thereof, for example, 35%, 40%, 45%, 50%, 55%, 60%, 65%, 70%, 75%, 80%, 85%, 90%, 95% or 100% identity thereto, and cysteine:glucosaminyl inositol ligase activity. In another embodiment, a derivative of glucosaminyl inositol is used in the method of the invention. Such derivatives may include, but are not limited to D-glucosamine. A glucosaminyl inositol substrate for use in screening for inhibitors of ligase activity is 1D-myo-inosityl 2-amino-2-deoxy-α-D-glucopyranoside (GlcN-Ins). In another aspect of the invention, the suitable conditions include the presence of ATP during ligation of cysteine to the glucosaminyl inositol or derivative thereof.

As set forth above, the polypeptides can be derived from bacteria, including actinomycetes. In one embodiment of identifying an inhibitor of cysteine:glucosaminyl inositol ligase, the ligase is produced in an actinomycete. Additionally, the invention provides an inhibitor of cysteine:glucosaminyl inositol ligase identified by the method of the invention.

Similarly, the invention provides a method for identifying an inhibitor of acetyl-CoA:cysteinyl glucosaminyl inositol (acetyl-CoA:Cys-GlcN-Ins) acetyltransferase (MshD). The method includes contacting a candidate compound with an acetyl-CoA:Cys-GlcN-Ins acetyltransferase in the presence of a cysteinyl glucosaminyl inositol (Cys-GlcN-Ins) and acetyl-CoA, under suitable conditions and determining the presence or absence of a transfer of acetyl to the Cys-GlcN-Ins. In the embodiment of the invention, the substantial absence of a transfer of acetyl is indicative of a candidate compound that inhibits activity of the acetyltransferase. For example, if the test compound is a putative inhibitor of acetyltransferase activity of a polypeptide acetyltransferase, the absence of an acetylated Cys-GlcN-Ins (mycothiol) indicates the candidate compound is an inhibitor of the activity of the polypeptide as an acetyltransferase. Similarly, if the test compound is assayed as a putative inhibitor of MshD in mycothiol-producing bacteria, the presence of excess Cys-GlcN-Ins indicates that the candidate compound is an inhibitor of the activity of the acetyltransferase for linkage of an acetyl group to a Cys-GlcN-Ins. On the other hand, in such assays, the presence of mycothiol indicates that the test compound is not an inhibitor of MshD activity.

In one embodiment, the acetyl-CoA:Cys-GlcN-Ins acetyltransferase of the method is characterized as having an amino acid sequence with 35% or more sequence identity to SEQ ID NO: 14 or 15, or conservative variations thereof, for example, 35%, 40%, 45%, 50%, 55%, 60%, 65%, 70%, 75%, 80%, 85%, 90%, 95% or 100% identity thereto, and acetyl-CoA:Cys-GlcN-Ins acetyltransferase activity. In one embodiment of the invention, the Cys-GlcN-Ins is 1D-myo-inosityl 2-L-cysteinylamido-2-deoxy-α-D-glucopyranoside.

As set forth above, the polypeptides can be obtained from bacteria, including actinomycetes. In one embodiment of identifying an inhibitor of acetyl-CoA:Cys-GlcN-Ins acetyltransferase, the acetyltransferase is produced in an actinomycete. Additionally, the invention provides an inhibitor of acetyl-CoA:Cys-GlcN-Ins acetyltransferase identified by the method of the invention.

In still another related embodiment of the invention, a method for identifying an inhibitor of MshA glycosyltransferase (MshA) is provided. The method includes contacting a candidate compound with a mycothiol-producing bacterium under suitable conditions and determining the presence or absence of 1D-myo-inosityl 2-acetamido-2-deoxy-α-D-glucopyranoside (GlcNAc-Ins) within the mycothiol-producing bacterium. In the embodiment of the invention, the substantial absence of GlcNAc-Ins within the bacterium is indicative of a compound that inhibits activity of the glycosyltransferase. For example, if the test compound is a putative inhibitor of glycosyltransferase activity of the polypeptide glycosyltransferase, the absence of GlcNAc-Ins indicates the candidate compound is an inhibitor of the activity of the polypeptide as a glycosyltransferase. On the other hand, in such assays, the presence of GlcNAc-Ins indicates that the test compound is not an inhibitor of MshA activity.

In one embodiment, the MshA glycosyltransferase of the method is characterized as having an amino acid sequence with 35% or more sequence identity to SEQ ID NO: 19 or 20, or conservative variations thereof, for example, 35%, 40%, 45%, 50%, 55%, 60%, 65%, 70%, 75%, 80%, 85%, 90%, 95% or 100% identity thereto, and having MshA glycosyltransferase activity.

As set forth above, the polypeptides can be obtained from bacteria, including actinomycetes. In one embodiment of identifying an inhibitor of MshA glycosyltransferase, the glycosyltransferase is produced in an actinomycete. Additionally, the invention provides an inhibitor of MshA glycosyltransferase identified by the method of the invention.

In still another embodiment, the invention provides a method for identifying an inhibitor of mycothiol biosynthesis. The method includes contacting a candidate compound with a mycothiol-producing bacterium, under suitable conditions, and determining the presence or absence of mycothiol within the mycothiol-producing bacterium. The substantial absence of mycothiol is indicative of a candidate compound that inhibits mycothiol biosynthesis. The inhibition of mycothiol biosynthesis can be by, but is not limited to, inhibition of cysteine:glucosaminyl inositol ligase, acetyl-CoA:Cys-GlcN-Ins acetyltransferase or MshA glycosyltransferase. Additionally, the excess or absence of intermediates of the mycothiol biosynthesis is indicative of an inhibitor of mycothiol biosynthesis. In another embodiment, the invention provides an inhibitor of mycothiol biosynthesis identified by the method.

In one embodiment, the mycothiol-producing bacterium of the method is an actinomycete. Additionally, the invention provides an inhibitor of mycothiol biosynthesis identified by the method of the invention.

In an alternative embodiment of the invention, methods are provided for decreasing the virulence in mammalian cells of a pathogenic MshC-producing, MshD-producing or MshA-producing bacterium, such as an actinomycete. By virulence is meant the relative power and degree of pathogenicity possessed by organisms to produce disease as measured by clinical symptoms particular to the disease under consideration. For example, the virulence of M. tuberculosis is measured with reference to the manifestation in an infected individual of the clinical symptoms recognized by a medical practitioner as indicative of tuberculosis. In the invention method for decreasing the virulence of pathogenic MshC-producing, MshD-producing or MshA-producing bacteria, an inhibitor of MshC, MshD or MshA (for example, one identified by the above-described screening method), respectively, is introduced into the bacterium.

Intracellular uptake of the inhibitor by the treated bacterium results in decreased activity of the enzyme, thereby decreasing mycothiol biosynthesis by the bacterium as compared with untreated control bacterium. Hence, the virulence of the treated bacterium is reduced. For example, for treatment of isolated mammalian cells, the introducing can comprise culturing the bacterium in the presence of the inhibitor. Alternatively, for treatment of mammalian cells contained in a living organism, the inhibitor may be administered systemically to the living organism. Pathogenic MshC-producing, MshD-producing or MshA-producing bacteria whose virulence can be reduced according to the invention methods include such actinomycetes as M. smegmatis, M. tuberculosis, M. leprae, M. bovis (particularly in bovine subjects), M. intracellulare, M. africanum, and M. marinarum. M. chelonai, Corynebacterium diphtheriae, Actinomyces israelii, M. avium complex (MAC), M. ulcerans, M. abscessus, M. scrofulaceum, and the like.

In one embodiment of the invention, a method for decreasing the virulence of a pathogenic cysteine:glucosaminyl inositol ligase-producing bacterium in mammalian cells is provided. Specifically, the method includes introducing an inhibitor of cysteine:glucosaminyl inositol ligase activity into the bacterium and observing the effect on the activity of the ligase. In the method of the invention, where the intracellular presence of the inhibitor causes a decrease in activity of the ligase, mycothiol biosynthesis by the bacterium is also decreased, as compared with untreated control bacterium.

The invention also provides a method for decreasing the virulence of a pathogenic acetyl-CoA:Cys-GlcN-Ins acetyltransferase-producing bacterium in mammalian cells. The method includes introducing an inhibitor of acetyl-CoA:Cys-GlcN-Ins acetyltransferase activity into the bacterium, where the intracellular presence of the inhibitor decreases activity of the acetyltransferase. Such a decrease also decreases mycothiol biosynthesis by the bacterium as compared with untreated control bacterium.

Similarly, the invention provides a method for decreasing the virulence of a pathogenic MshA glycosyltransferase-producing bacterium in mammalian cells. The method includes introducing an inhibitor of MshA glycosyltransferase activity into the bacterium. The intracellular presence of the inhibitor decreases activity of the glycosyltransferase, thereby decreasing mycothiol biosynthesis by the bacterium as compared with untreated control bacterium.

The inhibitors used in the invention methods for decreasing the virulence of a pathogenic MshC-producing, MshD-producing or MshA-producing bacterium may either inhibit intracellular production of the enzyme or inhibit intracellular catalytic activity of the enzyme. In one embodiment, the inhibitor inhibits intracellular production of mycothiol.

In various embodiments of the present invention there are provided inhibitors of the enzymes of mycothiol biosynthesis. These inhibitors may be identified, for example, by the screening method set forth above. For example, the inhibitor can be, but is not limited to a polypeptide, a polynucleotide or a small molecule.

In one embodiment, where inhibition of MshC is desired, the invention ligase inhibitors are derived from L-cysteine by replacing the carboxyl group with a moiety that binds the enzyme active site. Examples of the type of moiety that can be used to replace the carboxyl group in L-cysteine to form an inhibitor of the ligases are selected from moieties having the chemical structure $CH_2OPO(OH)OR$, wherein R is derived either from AMP or from a cyclitol bearing one or more branched or unbranched alkyl residues. In another embodiment where inhibition of MshC is desired, the invention inhibitors are derived from L-cysteine by replacing the carboxyl group therein with a moiety having the chemical structure $CONHSO_2OR$, wherein R is derived from AMP or R is a cyclitol bearing one or more branched or unbranched alkyl residues. Suitable alkyl residues for this purpose include, but are not limited to, those containing from 1 to 10 carbons, for example 2 to 8 carbons, 3 to 6 carbons, or 4 to 5 carbons.

In another embodiment according to the present invention, the invention inhibitor is an anti-sense oligonucleotide complementary to a target region in a messenger RNA that encodes a polypeptide having an amino acid sequence segment with 35% or more sequence identity to the amino acid sequence of SEQ ID NO: 2 or 4, 35% or more sequence identity to the amino acid sequence of SEQ ID NO: 14 or 15 or 35% or more sequence identity to the amino acid sequence of SEQ ID NO: 19 or 20. For example, the candidate compound can inhibit intracellular production or activity of the cysteine:glucosaminyl inositol ligase, acetyl-CoA:Cys-GlcN-Ins acetyltransferase or MshA glycosyltransferase. Suitable conditions for conducting invention drug screening methods are well known in the art and are described, for example, in the Examples below.

Alternatively, an anti-sense oligonucleotide can be designed to hybridize under in vivo conditions with a messenger RNA that encodes a polypeptide having an N-terminal amino acid sequence as set forth in SEQ ID NO: 2 or 4, or contains an amino acid segment as set forth in SEQ ID NOS: 7, 8 or 9, or a conservative variation thereof.

The anti-sense oligonucleotide can comprise from about 10 to about 60 nucleic acid residues, for example from 10 to about 50, or from 10 to about 40, 30 or 20 nucleic acid residues. "Hybridization" refers to the process by which a nucleic acid strand joins with a complementary strand through base pairing. Hybridization reactions can be sensitive and selective so that a particular sequence of interest will join with a complementary strand even in samples in which it is present at low concentrations. Suitable intracellular conditions for hybridization of an anti-sense oligonucleotide to messenger RNA will be determined by the particular bacterium used in the invention method. In general, the pH, temperature and salt concentration must be comparable to intracellular conditions in the test bacterium.

In yet another embodiment according to the present invention, there are provided methods for increasing sensitivity to an antibiotic of a pathogenic MshC-producing, MshD-producing or MshA-producing bacterium.

In such a method for increasing sensitivity of a pathogenic cysteine:glucosaminyl inositol ligase-producing bacterium in mammalian cells, an invention inhibitor of cysteine:glucosaminyl inositol ligase activity is introduced into the bacterium. The intracellular presence of the invention inhibitor in the bacterium decreases activity of the ligase, thereby decreasing mycothiol biosynthesis by the bacterium as compared with untreated control bacterium so as to increase sensitivity of the bacterium to an antibiotic. The inhibitor can inhibit intracellular production of the ligase or inhibit intracellular ligase activity of the ligase. In one embodiment, sensitivity of the bacterium to the antibiotic is increased while the bacterium is within a mammalian cell by a decreased activity of the ligase in the bacterium while contained within the host mammalian cell. The inhibitor can be introduced into the bacterium, for example, by culturing the bacterium in the presence of the inhibitor. Bacteria whose sensitivity to antibiotics can be increased by practice of the invention methods include such pathogenic bacteria as various actinomycetes. Specific examples of bacteria whose sensitivity to antibiotics can be increased by the invention methods include *M. smegmatis, M. tuberculosis, M. leprae, M. bovis, M. intracellulare, M. africanum, M. marinarum. M. chelonai, Corynebacterium diphtheria, Actinomyces israelii, M. avium* complex (MAC), *M. ulcerans, M. abscessus, M. scrofulaceum*, and the like. In another embodiment, the bacterium is an actinomycete and the inhibitor inhibits intracellular production of mycothiol.

Similarly, in a method for increasing sensitivity of a pathogenic acetyl-CoA:Cys-GlcN-Ins acetyltransferase-producing bacterium in mammalian cells to an antibiotic, an inhibitor of acetyl-CoA:Cys-GlcN-Ins acetyltransferase activity is introduced into the bacterium. The intracellular presence of the inhibitor in the bacterium decreases activity of the acetyltransferase, thereby decreasing mycothiol biosynthesis by the bacterium as compared with untreated control bacterium so as to increase sensitivity of the bacterium to an antibiotic. The inhibitor can inhibit intracellular production of the acetyltransferase or inhibit intracellular activity of the acetyltransferase. In one embodiment, sensitivity of the bacterium to the antibiotic is increased while the bacterium is within a mammalian cell by a decreased activity of the acetyltransferase in the bacterium while contained within the host mammalian cell. The inhibitor can be introduced into the bacterium, for example, by culturing the bacterium in the presence of the inhibitor.

Similarly, in a method for increasing sensitivity of a pathogenic acetyl-CoA:Cys-GlcN-Ins acetyltransferase-producing bacterium in mammalian cells to an antibiotic, an inhibitor of acetyl-CoA:Cys-GlcN-Ins acetyltransferase activity is introduced into the bacterium. The intracellular presence of the inhibitor in the bacterium decreases activity of the acetyltransferase, thereby decreasing mycothiol biosynthesis by the bacterium as compared with untreated control bacterium so as to increase sensitivity of the bacterium to an antibiotic. The inhibitor can inhibit intracellular production of the acetyltransferase or inhibit intracellular activity of the acetyltransferase. In one embodiment, sensitivity of the bacterium to the antibiotic is increased while the bacterium is within a mammalian cell by a decreased activity of the acetyltransferase in the bacterium while contained within the host mammalian cell. The inhibitor can be introduced into the bacterium, for example, by culturing the bacterium in the presence of the inhibitor.

Additionally, in a method for increasing sensitivity of a pathogenic MshA glycosyltransferase-producing bacterium in mammalian cells to an antibiotic, an inhibitor of MshA glycosyltransferase activity is introduced into the bacterium. The intracellular presence of the inhibitor in the bacterium decreases activity of the glycosyltransferase, thereby decreasing mycothiol biosynthesis by the bacterium as compared with untreated control bacterium so as to increase sensitivity of the bacterium to an antibiotic. The inhibitor can inhibit intracellular production of the glycosyltransferase or inhibit intracellular activity of the glycosyltransferase. In one embodiment, sensitivity of the bacterium to the antibiotic is increased while the bacterium is within a mammalian cell by a decreased activity of the glycosyltransferase in the bacterium while contained within the host mammalian cell. The inhibitor can be introduced into the bacterium, for example, by culturing the bacterium in the presence of the inhibitor.

In still another embodiment, the invention provides a method for increasing sensitivity of a pathogenic mycothiol-producing bacterium in mammalian cells to an antibiotic, by introducing an inhibitor of endogenous bacterial mycothiol biosynthesis into the bacterium. The intracellular presence of the inhibitor in the bacterium decreases mycothiol biosynthesis by the bacterium as compared with untreated control bacterium so as to increase sensitivity of the bacterium to an antibiotic. The inhibitor can inhibit intracellular production of cysteine: glucosaminyl inositol ligase, acetyl-CoA:Cys-GlcN-Ins acetyltransferase or MshA glycosyltransferase or can inhibit activity of the same. The inhibitor can be introduced into the bacterium, for example, by culturing the bacterium in the presence of the inhibitor.

Bacteria whose sensitivity to antibiotics can be increased by practice of the invention methods include such pathogenic bacteria as various actinomycetes. Specific examples of bacteria whose sensitivity to antibiotics can be increased by the invention methods include *M. smegmatis, M. tuberculosis, M. leprae, M. bovis, M. intracellulare, M. africanum, M. marinarum. M. chelonai, Corynebacterium diphtheria, Actinomyces israelii, M. avium* complex (MAC), *M. ulcerans, M. abscessus, M. scrofulaceum*, and the like. In another embodiment, the bacterium is an actinomycete and the inhibitor inhibits intracellular production of mycothiol.

In accordance with the above, the invention also provides a method of synthesizing mycothiol in vivo. By inserting mshA (for example, SEQ ID NO: 49 or a nucleic acid sequence encoding a protein having an amino acid sequence as set forth in SEQ ID NO: 19), mshB, mshC (for example, SEQ ID NO: 1 or 3) and mshD (for example, SEQ ID NO: 48 or a nucleic acid sequence encoding a protein having an amino acid sequence as set forth in SEQ ID NO: 15), the genes for the four enzymes of mycothiol production, into a plasmid and inserting the plasmid into an organism, all four enzymes are expressed. With this expression, mycothiol is produced by the host cell. This method may be used to stimulate mycothiol production in the organism or increase existing mycothiol production. Such an increase of mycothiol within an organism serves to increase tolerance of the organism to antibiotics. Such an increase in antibiotic tolerance is useful to protect antibiotic-producing organisms from the toxic effects of the antibiotics they produce.

Therefore in an embodiment according to the present invention, there are provided methods for increasing production of antibiotic by antibiotic-producing bacteria by transforming the antibiotic-producing bacteria with a polynucleotide that increases intracellular mycothiol production by the bacteria in culture. The increase in intracellular production of mycothiol increases the production of antibiotic by the bacteria by increasing resistance of the bacteria to the antibiotic. Generally, in industrial applications where antibiotic is produced from bacteria for commercial purposes, the antibiotic-producing bacteria are cultured under conditions suitable for production of the antibiotic, and the antibiotic is recovered from the culture media.

In one embodiment, the compound that increases intracellular mycothiol production by the bacteria is expressed intracellularly by the bacteria. In one embodiment, the bacteria is actinomycetes. For example, the actinomycetes can be transformed with a polynucleotide, such as an expression vector, that encodes one or more enzymes involved in the mycothiol biosynthesis pathway and which produces mycothiol in culture. Recombinant expression of the polypeptides in cultured antibiotic-producing cells can be useful for increasing the resistance of the production cells to the toxic effect upon themselves of the antibiotics they produce. Thus, the level of antibiotics in the culture media can be increased without causing death of the production cells, thereby increasing the efficiency of industrial antibiotic production methods. Suitable polynucleotides that can be used to transform antibiotic-producing bacteria can contain, for example, SEQ ID NOS: 1, 48 or 49.

In yet another embodiment according to the present invention, there are provided live mutant actinomycetes, whose genomes comprise a modification in an endogenous enzyme of the mycothiol biosynthesis pathway and thereby reduce mycothiol synthesis. Appropriate modification of genes for mycothiol biosynthesis in mycobacteria can reduce their survival in mammalian macrophages. Modification of any one of the endogenous cysteine:glucosaminyl inositol ligase gene, acetyl-CoA:Cys-GlcN-Ins acetyltransferase gene or MshA glycosyltransferase gene can reduce function of an endogenous cysteine:glucosaminyl inositol ligase, acetyl-CoA:Cys-GlcN-Ins acetyltransferase or MshA glycosyltransferase, respectively, while cell surface proteins and lipids should be substantially unaffected. As a result, invention live mutant actinomycetes exhibit the phenotype of transient survival in mammalian white blood cells, such as murine or human white blood cells, for an immune response raising period of time. Such genetically engineered live mutant actinomycetes will survive in mammalian white blood cells for a period of time from 1 to 30 days, for example from 4 to 25 days or from 5 to 20 days, but in no event for more than 30 days. Due to lack of intracellular cysteine:glucosaminyl inositol ligase, acetyl-CoA:Cys-GlcN-Ins acetyltransferase or MshA glycosyltransferase, the invention live mutant bacterium will fail to produce sufficient mycothiol. Hence, the mutant live bacterium is unable to survive the oxidative stress inherent in the intracellular environment of mammalian white blood cells long enough to establish infection in the cells or to establish infection in an immunocompetent mammal containing such white blood cells. In one embodiment, the live mutant contains a modification of the acetyl-CoA:Cys-GlcN-Ins acetyltransferase gene or the MshA glycosyltransferase gene and the resulting mutant is resistant to isoniazid.

Thus, invention live mutant actinomycetes possess a combination of features desired for a vaccine effective in mammals against infection by such pathogenic *actinomycetes* as *M. smegmatis, M. tuberculosis, M. leprae, M. bovis, M. intracellulare, M. africanum, M. marinarum. M chelonai, Corynebacterium diphtheria, Actinomycetes israelii, M. avium* complex (MAC), *M. ulcerans, M. abscessus, M. scrofulaceum*, and the like. An individual (e.g., an animal, such as a mouse, a farm animal or a human) to which the live mutant is administered according to a protocol appropriate for inducing a protective immune response and who has not previously been infected by the counterpart wild type will mount an immune response to the vaccine, for example an immune response sufficient to protect the individual against future infection by the corresponding wild type live pathogen. Alternatively, the invention live mutant actinomycetes are useful as a research tool to investigate the properties desirable in a live mutant vaccine.

The invention also provides a method for inhibiting growth of Cys-GlcN-Ins-producing bacterium, acetyl-CoA:Cys- GlcN-Ins acetyltransferase-producing bacterium or GlcNAc-Ins-producing bacterium. In the method reducing the growth of Cys-GlcN-Ins-producing bacterium, an inhibitor of intracellular cysteine:glucosaminyl inositol ligase is administered to the mammal. In the method reducing the growth of acetyl-CoA:Cys-GlcN-Ins acetyltransferase-producing bacterium, an inhibitor of intracellular acetyl-CoA:Cys-GlcN-Ins acetyltransferase is administered to the mammal. Similarly, in the method reducing the growth of GlcNAc-Ins-producing bacterium, an inhibitor of intracellular MshA glycosyltransferase is administered to the mammal. Such administration of an inhibitor of cysteine:glucosaminyl inositol ligase, acetyl-CoA:Cys-GlcN-Ins acetyltransferase or MshA glycosyltransferase will inhibit growth of the bacterium in the mammal. In one embodiment, the bacterium is a mycothiol-producing bacterium. Bacteria whose growth can be inhibited by the practice of the invention methods utilizing such inhibitors can include such pathogenic bacteria as various actinomycetes. Specific examples of bacteria whose growth can be inhibited by the invention methods include *M. smegmatis*, *M. tuberculosis*, *M. leprae*, *M. bovis*, *M. intracellulare*, *M. africanum*, *M. marinarum*. *M. chelonai*, *Corynebacterium diphtheria*, *Actinomyces israelii*, *M. avium* complex (MAC), *M. ulcerans*, *M. abscessus*, *M. scrofulaceum*, and the like.

It appears that the difficulty in purifying the Cys:GlcN-Ins ligase derives in part from the presence of two different forms of the MshC protein and their tendency to oligomerize. Some of the different forms apparently elute separately on some chromatography columns but, once separated, can rearrange to regenerate multiple forms. The ligase activity eluted from Sephadex G100 as an apparent tetramer but the purified ligase was collected as what appeared to be partially resolvable $\alpha_2$ and $\beta_2$ dimers. Since the *M. tuberculosis* gene did not exhibit upstream homology to the *M. smegmatis* gene in the region coding for the N-terminal extension of the larger protein, this problem may be unique to *M. smegmatis*. The significance of multiple forms of the enzyme under physiologic conditions is not clear.

Figure 5:
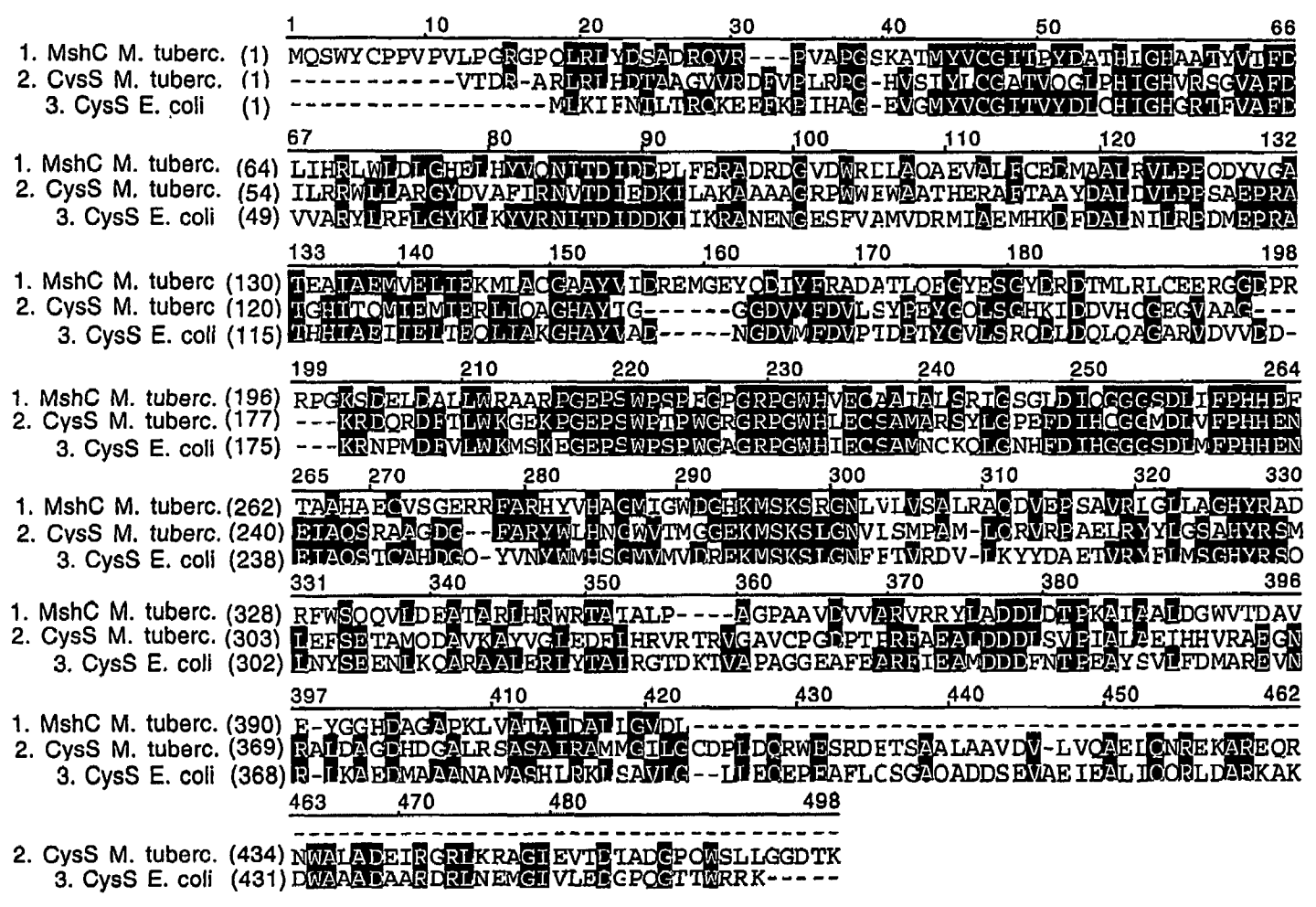

Bacteria generally produce one aminoacyl-tRNA synthetase for each of the 20 natural amino acids, but some exceptions are known (T. Meinnel et al. (1995) in *tRNA: Structure, Biosynthesis, and Function* (Soll, D. and RajBhandary, U., Eds.) pp 251-292, ASM Press, Washington, D.C.). However, in those cases where two aminoacyl-tRNA synthetases for the same amino acid have been identified, they have nearly identical size. This is not the case with CysS and CysS2 (MshC), which in *M. tuberculosis* are comprised of 475 and 414 residues, respectively. There are structural similarities and differences between CysS and MshC from *M. tuberculosis* (FIG. 5). CysS lacks the N-terminal sequence (residues 1-19, FIG. 4) partially conserved in the mshC genes. The cysS and the mshC genes possess the "HIGH" (T. Webster et al. (1984) *Science* 226, 1315-131719 and J. J. Burbaum et al. (1990) *Proteins* 7, 99-111), and "KMSKS" (C. Hountondji et al. (1986) *Biochemistry* 25:16-21 and C. Hountondji et al. (1990) *Biochemistry* 29, 8190-8198) signatures characteristic of Class I aminoacyl-tRNA synthetases (T. Meinnel et al., supra). However, whereas the CysS proteins contain the actual HIGH sequence near residue 40 (FIG. 5), the sequence is H(L/M)GH in the MshC proteins shown in FIG. 4. The substitution of Leu or Met for Ile is found in several Class I aminoacyl-tRNA synthetases (T. Meinnel, supra). The CysS protein of *M. tuberculosis* has a 76 residue extension beyond the C-terminus of MshC which has substantial identity (29%) with corresponding 69 residue extension in the CysS from *E. coli* (FIG. 5). Overall, the CysS of *M. tuberculosis* is 42% identical to the CysS of *E. coli* and 32% identical to MshC of *M. tuberculosis*. Finally, CysS has been normally found to be active as a monomer whereas MshC is active in both dimer and tetramer forms. Thus, it has been discovered that CysS of *M. tuberculosis* is the true cysteinyl-tRNA synthetase and the protein originally classified as CysS2 is actually the Cys:GlcN-Ins ligase (MshC) It seems logical that mshC originated from the cysS gene following a gene duplication.

Figure 7:
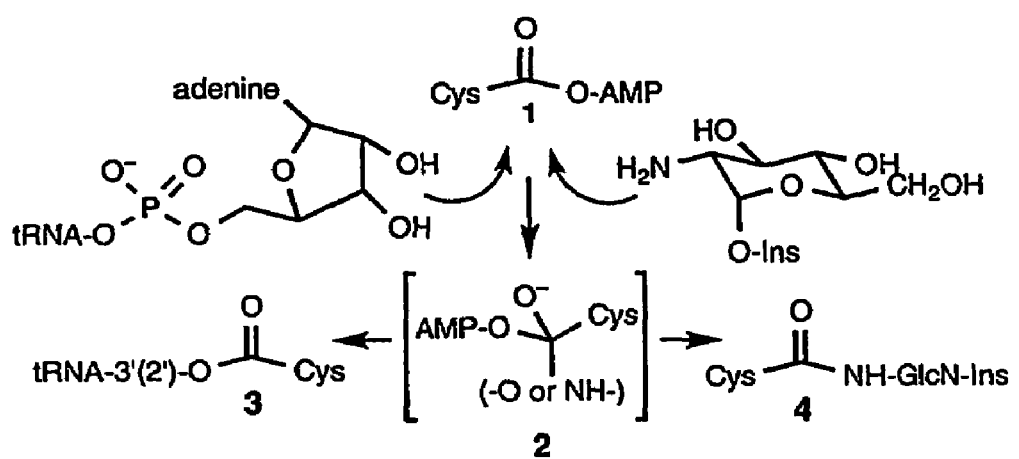
FIG. 7 is a schematic representation of the chemistry of cysteinyl-tRNA synthetase and Cys:GlcN-Ins ligase reactions.

FIG. 7 is a schematic representation of the chemistry of cysteinyl-tRNA synthetase and Cys:GlcN-Ins ligase reactions. The enzyme mechanism of the aminoacyl-tRNA synthetases involves activation of cysteine to produce a cysteinyl-AMP intermediate (T. Meinnel, supra). The activated cysteinyl group is subsequently transferred to the 2' or 3' ribosyl hydroxyl at the 3' terminus of t-RNA$^{cys}$ to produce the charged cysteinyl ester on t-RNA$^{cys}$ (FIG. 7). The initial step, formation of AMP-Cys (1), is the same for the ligase reaction. The ligase mechanism differs chemically by recognition of GlcN-Ins in place of the ribose of t-RNA$^{cys}$ and in the attack of the amino group, in place of a hydroxyl group, upon AMP-Cys (FIG. 5). A general base on the enzyme presumably functions to remove a proton from the hydroxyl or amino group leading to formation of a tetrahedral intermediate (2) which decomposes to form an ester (3), in the case of cysteinyl-tRNA synthetase, or an amide (4) in the case of the ligase. The later process is chemically more favorable owing to the greater nucleophilicity of amines over alcohols and the greater thermodynamic stability of amides relative to esters. These features, inherent in the chemistry of the reactions, make evolution of the ligase from a cysteinyl-tRNA synthetase a highly plausible route.

A "conservative variation" in an amino acid sequence is a sequence that differs from a reference sequence by one or more conservative or non-conservative amino acid substitutions, deletions, or insertions, particularly when such a substitution occurs at a site that is not the active site of the molecule, and provided that the polypeptide essentially retains its functional properties. A conservative amino acid substitution, for example, substitutes one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid or glutamine for asparagine). One or more amino acids can be deleted, for example, from a ligase polypeptide, resulting in modification of the structure of the polypeptide, without significantly altering its biological activity. For example, carboxyl-terminal amino acids that are not required for ligase or ligase activity of the mycothiol biosynthesis polypeptides can be removed.

Biologically functional viral and plasmid DNA vectors capable of expression and replication in a host are known in the art. Such vectors are used to incorporate DNA sequences of the invention. In general, expression vectors containing promoter sequences which facilitate the efficient transcription of the inserted eukaryotic genetic sequence are used in connection with the host. The expression vector typically contains an origin of replication, a promoter, and a terminator, as well as specific genes that are capable of providing phenotypic selection of the transformed cells.

In addition to expression vectors known in the art such as bacterial, yeast and mammalian expression systems, baculovirus vectors may also be used. One advantage to expression of foreign genes in this invertebrate virus expression vector is that it is capable of expression of high levels of recombinant proteins, which are antigenically and functionally similar to their natural counterparts. Baculovirus vectors and the appropriate insect host cells used in conjunction with the vectors will be known to those skilled in the art.

The term "recombinant expression vector" refers to a plasmid, virus or other vehicle known in the art that has been manipulated by insertion or incorporation of the cysteine: glucosaminyl inositol ligase genetic sequences. Such expression vectors contain a promoter sequence that facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to, the T7-based expression vector for expression in bacteria (Rosenberg, et al., (1987) Gene, 56:125), the pMSXND expression vector for expression in mammalian cells (Lee and Nathans, (1988) J. Biol. Chem., 263:3521) and baculovirus-derived vectors for expression in insect cells. The DNA segment can be present in the vector operably linked to regulatory elements, for example, a promoter (e.g., T7, metallothionein I, or polyhedrin promoters).

The vector may include a phenotypically selectable marker to identify host cells which contain the expression vector. Examples of markers typically used in prokaryotic expression vectors include antibiotic resistance genes for ampicillin (β-lactamases), tetracycline and chloramphenicol (chloramphenicol acetyltransferase). Examples of markers typically used in prokaryotic expression vectors used in mycobacteria can include, but are not limited to kanomycin and streptomycin resistance genes. Examples of such markers typically used in mammalian expression vectors include the gene for adenosine deaminase (ADA), aminoglycoside phosphotransferase (neo, G418), dihydrofolate reductase (DHFR), hygromycin-B-phosphotransferase (HPH), thymidine kinase (TK), xanthine guanine phosphoribosyltransferse (XGPRT, gpt), inomycin, streptomycin and kanamycin.

The isolation and purification of host cell expressed polypeptides may be by any conventional means such as, for example, preparative chromatographic separations and immunological separations such as those involving the use of monoclonal or polyclonal antibody.

Transformation of the host cell with the recombinant DNA may be carried out by conventional techniques well known to those skilled in the art. Where the host is prokaryotic, such as E. coli, competent cells which are capable of DNA uptake can be prepared from cells harvested after exponential growth and subsequently treated by electroporation or the $CaCl_2$ method using procedures well known in the art. Alternatively, $MgCl_2$ or RbCl could be used.

Where the host used is a eukaryote, various methods of DNA transfer can be used. These include transfection of DNA by calcium phosphate-precipitates, conventional mechanical procedures such as microinjection, insertion of a plasmid encased in liposomes, or the use of virus vectors. Eukaryotic cells can also be cotransformed with DNA sequences encoding the mycothiol biosynthesis polypeptides, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982). Examples of mammalian host cells include COS, BHK, 293, and CHO cells.

Eukaryotic host cells may also include yeast. For example, DNA can be expressed in yeast by inserting the DNA into appropriate expression vectors and introducing the product into the host cells. Various shuttle vectors for the expression of foreign genes in yeast have been reported (Heinemann, J. et al., (1989) Nature, 340:205; Rose, M. et al., (1987) Gene, 60:237).

The invention also provides antibodies that are specifically reactive with mycothiol biosynthesis enzyme polypeptides or fragments thereof. Such antibodies can be used as research tools to aid in isolation of mycothiol biosynthesis enzymes such as MshC, MshD or MshA.

The invention also provides antibodies that consist essentially of pooled monoclonal antibodies with different epitopic specificities, as well as distinct monoclonal antibody preparations are provided. Monoclonal antibodies are made from antigen-containing fragments of the protein by methods well known in the art (Kohler, et al., Nature, 256:495, 1975; Current Protocols in Molecular Biology, Ausubel, et al., ed., 1989). Monoclonal antibodies specific for MshC polypeptide, MshD polypeptide or MshA polypeptide can be selected, for example, by screening for hybridoma culture supernatants that react with the MshC polypeptide, MshD polypeptide or MshA polypeptide, but do not react with other bacterial ligases, acetyltransferases or glycosyltransferases, respectively.

Additionally, the invention provides antibodies that consist essentially of pooled monoclonal antibodies with different epitopic specificities, as well as distinct monoclonal antibody preparations are provided. Monoclonal antibodies are made from antigen containing fragments of a protein by methods well known in the art (Kohler, et al., Nature, 256:495, 1975; Current Protocols in Molecular Biology, Ausubel, et al., ed., 1989).

The term "antibody" as used in this invention includes intact molecules as well as fragments thereof, such as Fab, $F(ab')_2$ and Fv, which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')2, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, New York (1988), incorporated herein by reference).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three-dimensional structural characteristics, as well as specific charge characteristics.

Antibodies that bind to a MshC polypeptide, MshD polypeptide or MshA polypeptide of the invention can be prepared using an intact polypeptide or fragments containing small peptides of interest as the immunizing antigen. The polypeptide or a peptide used to immunize an animal can be derived from translated cDNA or chemical synthesis and can be conjugated to a carrier protein, if desired. Such commonly used carriers, which are chemically coupled to the peptide, include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, Current Protocols in Immunology, Wiley Interscience, 1994, incorporated herein by reference).

It is also possible to use anti-idiotype technology to produce monoclonal antibodies that mimic an epitope. For example, an anti-idiotypic monoclonal antibody made to a first monoclonal antibody will have a binding domain in the hypervariable region that is the "image" of the epitope bound by the first monoclonal antibody.

In yet another embodiment, the recombinant cysteine:glucosaminyl inositol ligase polypeptide is a fusion protein further comprising a second polypeptide portion having an amino acid sequence from a protein unrelated to the cysteine:glucosaminyl inositol ligase. Similarly, in such an embodiment the recombinant acetyl-CoA:Cys-GlcN-Ins acetyltransferase polypeptide is a fusion protein further comprising a second polypeptide portion having an amino acid sequence from a protein unrelated to the acetyl-CoA:Cys-GlcN-Ins acetyltransferase. In still another embodiment, the invention provides a recombinant MshA glycosyltransferase polypeptide, which is a fusion protein further comprising a second polypeptide portion having an amino acid sequence from a protein unrelated to the MshA glycosyltransferase. Such fusion proteins can be functional in a two-hybrid assay.

Another aspect of the present invention provides a substantially pure nucleic acid having a nucleotide sequence that encodes a cysteine:glucosaminyl inositol ligase polypeptide, or a fragment thereof, having an amino acid sequence with 35% or greater homology to one of SEQ ID NO: 2. In another embodiment, the nucleic acid encodes a protein having an amino acid sequence having 40% or more homologous to SEQ ID NO: 2, in one embodiment, the protein has an amino acid sequence at least 45% homologous to SEQ ID NO: 2, and in another embodiment at least 50% homologous to SEQ ID NO: 2, in another embodiment, the nucleic acid encodes a protein having an amino acid sequence having 35% or more sequence identity to the amino acid sequence of SEQ ID NO: 15, and in still another embodiment, the nucleic acid encodes a protein having an amino acid sequence having 35% or more sequence identity to the amino acid sequence of SEQ ID NO: 19.

Furthermore, in certain embodiments, the cysteine:glucosaminyl inositol ligase, acetyl-CoA:Cys-GlcN-Ins acetyltransferase or MshA glycosyltransferase nucleic acid will comprise a transcriptional regulatory sequence, e.g. at least one of a transcriptional promoter or transcriptional enhancer sequence, operably linked to the mshC, mshD or mshA gene sequence so as to render the recombinant cysteine:glucosaminyl inositol ligase, acetyl-CoA:Cys-GlcN-Ins acetyltransferase or MshA glycosyltransferase gene sequence suitable for use as an expression vector.

The present invention also features transgenic non-human organisms, e.g. live mutant actinomycetes, which either express a heterologous mshC, mshD or mshA gene, or in which expression of their own mshC, mshD or mshA gene is disrupted. In addition to the other utilities of such organisms disclosed herein, such a transgenic organism with a disrupted mshC gene has utility for overproduction of glucosaminyl inositol needed for screening (particularly high throughput screening) for compounds that inhibit cysteine:glucosaminyl inositol ligase activity in mycothiol-producing bacteria. Similarly, a transgenic organism with a disrupted mshD gene has utility for overproduction of Cys-GlcN-Ins.

The present invention also provides a probe/primer comprising a substantially purified oligonucleotide, wherein the oligonucleotide comprises a region of nucleotide sequence which hybridizes under stringent conditions to at least 10 consecutive nucleotides of sense or anti-sense sequence encoding one of the amino acid sequences encompassed by SEQ ID NOS: 2, 4, 14, 15, 19, 20, or naturally occurring mutants thereof.

Yet another aspect of the invention pertains to a peptidomimetic that binds to or interferes with a MshC polypeptide, MshD polypeptide or MshA polypeptide and inhibits its respective activity. For example, a peptidomimetic that binds to or interferes with a MshC polypeptide can inhibit binding to or linkage of substrate cysteine to glucosaminyl inositol or a derivative thereof. An exemplary peptidomimetic is an analog of a peptide having the sequence of one of the SEQ ID NOS: 2 or 4. Non-hydrolyzable peptide analogs of such residues can be generated using, for example, benzodiazepine, azepine, substituted gama-lactam rings, keto-methylene pseudopeptides, beta-turn dipeptide cores, or beta-aminoalcohols. Similarly, a peptidomimetic that binds to or interferes with a MshD polypeptide can inhibit binding to or linkage of acetyl to substrate Cys-GlcN-Ins or a derivative thereof. An exemplary peptidomimetic is an analog of a peptide having the sequence of one of the SEQ ID NOS: 14 or 15. Also, a peptidomimetic that binds to or interferes with a MshA polypeptide can inhibit production of GlcNAc-Ins. An exemplary peptidomimetic is an analog of a peptide having the sequence of one of the SEQ ID NOS: 19 or 20.

Other features and advantages of the invention will be apparent from the detailed description herein, and from the claims. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H.

Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

As used herein, the term "actinomycetes" and "an actinomycete" encompasses any bacterium of the order Actinomycetales.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or anti-sense) and double-stranded polynucleotides.

As used herein, the terms "gene," "recombinant gene" and "gene construct" refer to a nucleic acid comprising an open reading frame encoding a cysteine:glucosaminyl inositol ligase, acetyl-CoA:Cys-GlcN-Ins acetyltransferase or MshA glycosyltransferase, including both exon and (optionally) intron sequences. The term "intron" refers to a DNA sequence present in a given cysteine:glucosaminyl inositol ligase, acetyl-CoA:Cys-GlcN-Ins acetyltransferase or MshA glycosyltransferase gene that is not translated into protein and is generally found between exons.

"Homology" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. Percent homology between sequences is a function of the number of matching or homologous positions shared by the sequences.

The sequence data of a test clone is aligned to the sequences in the database or databases using algorithms designed to measure homology between two or more sequences. Sequence alignment methods include, for example, BLAST (Altschul et al., 1990), BLITZ (MPsrch) (Sturrock & Collins, 1993), and FASTA (Person & Lipman, 1988). For example, optimal alignment of sequences for aligning a comparison window may be conducted by the local homology algorithm of Smith (Smith and Waterman, Adv Appl Math, 1981; Smith and Waterman, J Teor Biol, 1981; Smith and Waterman, J Mol Biol, 1981; Smith et al, J Mol Evol, 1981), by the homology alignment algorithm of Needleman (Needleman and Wuncsch, 1970), by the search of similarity method of Pearson (Pearson and Lipman, 1988), by computerized implementations of these algorithms (GAP, BESTFIT, FASTA, and TFASTA in the Wisconsin Genetics Software Package Release 7.0, Genetics Computer Group, 575 Science Dr., Madison, Wis., or the Sequence Analysis Software Package of the Genetics Computer Group, University of Wisconsin, Madison, Wis.), or by inspection, and the best alignment (i.e., resulting in the highest percentage of homology over the comparison window) generated by the various methods is selected.

The term "transfection" or "transforming" and grammatical equivalents thereof, refers to the introduction of a nucleic acid, e.g., an expression vector, into a recipient cell by nucleic acid-mediated gene transfer. "Transformation," as used herein, refers to a process in which a cell's genotype is changed as a result of the cellular uptake of exogenous DNA or RNA, and, for example, the transformed cell expresses a recombinant form of one of cysteine:glucosaminyl inositol ligase, acetyl-CoA:Cys-GlcN-Ins acetyltransferase or MshA glycosyltransferase.

"Cells" or "cell cultures" or "recombinant host cells" or "host cells" are often used interchangeably as will be clear from the context. These terms include the immediate subject cells that express cysteine:glucosaminyl inositol ligases, acetyl-CoA:Cys-GlcN-Ins acetyltransferases or MshA glycosyltransferases of the present invention, and, of course, the progeny thereof. It is understood that not all progeny are exactly identical to the parental cell, due to chance mutations or difference in environment. However, such altered progeny are included in these terms, so long as the progeny retain the characteristics relevant to those conferred on the originally transformed cell. In the present case, such a characteristic might be the ability to produce a recombinant MshC polypeptide, MshD polypeptide or MshA polypeptide.

As used herein, the term "vector" refers to a nucleic acid molecule capable of transporting another nucleic acid to which it has been linked. The term "expression vector" includes plasmids, cosmids or phages, and the like, capable of synthesizing a subject MshC polypeptide, MshD polypeptide or MshA polypeptide encoded by the respective recombinant gene carried by the vector. Preferred vectors are those capable of autonomous replication and/expression of nucleic acids to which they are linked. In the present specification, "plasmid" and "vector" are used interchangeably as the plasmid is the most commonly used form of vector. Moreover, the invention is intended to include such other forms of expression vectors which serve equivalent functions and which become known in the art subsequently hereto.

"Transcriptional regulatory sequence" is a generic term used throughout the specification to refer to DNA sequences, such as initiation signals, enhancers, and promoters, as well as polyadenylation sites, which induce or control transcription of protein coding sequences with which they are operably linked. In one embodiment, transcription of a recombinant mshC, mshD or mshA gene is under the control of a promoter sequence (or other transcriptional regulatory sequence) that controls the expression of the recombinant gene in a cell-type in which expression is intended. It will also be understood that the recombinant gene can be under the control of transcriptional regulatory sequences which are the same or which are different from those sequences that control transcription of the naturally occurring form of the regulatory protein.

As used herein, a "transgenic organism" is any organism, preferably a bacteria in which one or more of the cells of the organism contain heterologous nucleic acid introduced by way of human intervention, such as by transgenic techniques well known in the art. The nucleic acid is introduced into the cell by way of deliberate genetic manipulation, such as by microinjection or by infection with a recombinant virus or a vector. The term genetic manipulation does not include classical crossbreeding, or in vitro fertilization, but rather is directed to the introduction of a recombinant DNA molecule. This molecule may be integrated within a chromosome, or it may be extrachromosomally replicating DNA. In the typical transgenic organisms described herein, the transgene causes cells to express a recombinant form of the subject MshC polypeptides, MshD polypeptides or MshA polypeptides.

As used herein, the term "transgene" means a nucleic acid sequence (encoding, e.g., a MshC polypeptide, MshD polypeptide or MshA polypeptide), which is partly or entirely heterologous, i.e., foreign, to the transgenic organism or cell into which it is introduced, or, is homologous to an endogenous gene of the transgenic organism or cell into which it is introduced, but which is designed to be inserted, or is inserted, into the organism's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

The term "evolutionarily related to," with respect to nucleic acid sequences encoding MshC polypeptides, MshD polypeptides or MshA polypeptides, refers to nucleic acid sequences that have arisen naturally in an organism, including naturally occurring mutants. The term also refers to nucleic acid sequences which, while derived from a naturally occurring MshC polypeptide, MshD polypeptide or MshA polypeptide, have been altered by mutagenesis, as for example, combinatorial mutagenesis, yet still encode polypeptides which have the ligase activity of a cysteine:glucosaminyl inositol ligase polypeptide, acetyltransferase activity of an acetyl-CoA:Cys-GlcN-Ins acetyltransferase polypeptide or glycosyltransferase activity of a MshA glycosyltransferase polypeptide and may have such respective activity in modified form, such as modified level of activity or conditions of optimal activity, e.g., temperature of optimal activity, and the like.

Also provided is an isolated nucleic acid comprising the nucleotide sequence encoding a MshC polypeptide, MshD polypeptide or MshA polypeptide, fragments thereof encoding polypeptides having MshC, MshD or MshA activity, and/or equivalents of such nucleic acids. The term nucleic acid as used herein is intended to include such fragments and equivalents. The term equivalent is understood to include nucleotide sequences encoding functionally equivalent polypeptides or functionally equivalent peptides having an activity of a polypeptide such as described herein. Equivalent nucleotide sequences will include sequences that differ by one or more nucleotide substitutions, additions or deletions, such as allelic variants; and will also include sequences that differ from the nucleotide sequence encoding the desired enzyme due to the degeneracy of the genetic code. Equivalents will also include nucleotide sequences that hybridize under stringent conditions (i.e., equivalent to about 20-27° C. below the melting temperature of the DNA duplex formed in about 1 M salt) to the nucleotide sequence of a cysteine:glucosaminyl inositol ligase gene, such as that as set forth in SEQ ID NO: 1 or 3, particularly those segments encoding the polypeptides shown in one of SEQ ID NOS: 7, 8, or 9, or conservative variations thereof, nucleotide sequences that hybridize under stringent conditions to the nucleotide sequence of a acetyl-CoA:Cys-GlcN-Ins acetyltransferase gene, such as that set forth in SEQ ID NO: 48 or a MshA glycosyltransferase gene, such as that set forth in SEQ ID NO: 49. In one embodiment, equivalents will further include nucleic acid sequences derived from and evolutionarily related to such nucleotide sequences.

The term "isolated" or "purified" as also used herein with respect to nucleic acids, such as DNA or RNA, refers to molecules separated from other DNAs, or RNAs, respectively, that are present in the natural source of the macromolecule. For example, an isolated nucleic acid encoding one of the subject MshC, MshD or MshA polypeptides includes, in one embodiment, no more than 10 kilobases (kb) of nucleic acid sequence which naturally immediately flanks the mshC, mshD or mshA gene in genomic DNA, in another embodiment no more than 5 kb of such naturally occurring flanking sequences, and in still another embodiment less than 1.5 kb of such naturally occurring flanking sequence. The term isolated or purified as used herein also refers to a nucleic acid or peptide that is substantially free of cellular material or culture medium when produced by recombinant DNA techniques, or chemical precursors or other chemicals when chemically synthesized. Moreover, an "isolated nucleic acid" is meant to include nucleic acid fragments that are not naturally occurring as fragments and would not be found in the natural state.

In yet another embodiment, the nucleic acid set forth above encodes a peptide having an amino acid sequence as shown SEQ ID NO: 2. The nucleic acids encode a peptide having cysteine:glucosaminyl inositol ligase polypeptide activity and being 35% or more homologous, in another embodiment, 40% homologous and in still another embodiment, 45% homologous with an amino acid sequence as set forth in SEQ ID NO: 2 (encoded by a nucleic acid sequence as set forth in SEQ ID NO: 1). Nucleic acids that encode peptides having an activity of cysteine:glucosaminyl inositol ligase polypeptide are also within the scope of the invention. Further, the nucleic acid of the invention encodes a peptide having an amino acid sequence as shown SEQ ID NO: 14 or 15. In still another embodiment, the invention provides a nucleic acid that encodes a peptide having an amino acid sequence as shown SEQ ID NO: 19 or 20.

Another aspect of the invention provides a nucleic acid which hybridizes under high or low stringency conditions to a nucleic acid which encodes a cysteine:glucosaminyl inositol ligase polypeptide having all or a portion of an amino acid sequence shown in one of SEQ ID NOS: 2, 4, 7, 8 or 9. Similarly, the invention provides a nucleic acid which hybridizes under high or low stringency conditions to a nucleic acid which encodes an acetyl-CoA:Cys-GlcN-Ins acetyltransferase polypeptide having all or a portion of an amino acid sequence shown in one of SEQ ID NOS: 14 or 15. Additionally, the invention provides a nucleic acid which hybridizes under high or low stringency conditions to a nucleic acid which encodes a MshA glycosyltransferase polypeptide having all or a portion of an amino acid sequence shown in one of SEQ ID NOS: 19 or 20. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

Isolated nucleic acids that differ from the nucleotide sequences disclosed herein due to degeneracy in the genetic code are also within the scope of the invention. For example, more than one triplet designates a number of amino acids. Codons that specify the same amino acid, or synonyms (for example, CAU and CAC are synonyms for histidine) may result in "silent" mutations that do not affect the amino acid sequence of the protein. However, it is expected that DNA sequence polymorphisms that do lead to changes in the amino acid sequences of the subject MshC, MshD or MshA polypeptides will exist among prokaryotic cells. One skilled in the art will appreciate that these variations in one or more nucleotides (up to about 3-4% of the nucleotides) of the nucleic acids encoding a particular member of the MshC, MshD or MshA polypeptide family may exist among individuals of a given species due to natural allelic variation. Any and all such nucleotide variations and resulting amino acid polymorphisms are within the scope of this invention.

Fragments of the nucleic acid encoding a biologically active portion of the subject MshC, MshD or MshA polypeptides are also within the scope of the invention. As used herein, a fragment of the nucleic acid encoding an active portion of a MshC, MshD or MshA polypeptide refers to a nucleotide sequence having fewer nucleotides than the nucleotide sequence encoding the full length amino acid sequence of, for example, the ligase polypeptides represented in nucleic acid SEQ ID NO: 1, and which encodes a peptide which retains at least a portion of the biological activity of the full-length protein (i.e., a peptide capable of cysteine:glucosaminyl inositol ligase activity) as defined herein, or alternatively, which is functional as an antagonist of the activity of the full-length protein. Nucleic acid fragments within the scope of the invention include those capable of hybridizing under high or low stringency conditions with nucleic acids from other species, e.g. for use in screening protocols to detect homologs of the subject MshC, MshD or MshA polypeptides. Nucleic acids within the scope of the invention may also contain linker sequences, modified restriction endonuclease sites and other sequences useful for molecular cloning, expression or purification of such recombinant peptides.

As indicated by the examples set out below, a nucleic acid encoding a peptide having an activity of a mycothiol biosynthesis ligase, acetyltransferase or glycosyltransferase polypeptide may be obtained from mRNA or genomic DNA present in any of a number of antibiotic-producing or pathogenic bacteria, particularly actinomycetes, in accordance with protocols described herein, as well as those generally known to those skilled in the art. A cDNA encoding a MshC, MshD or MshA polypeptide, for example, can be obtained by isolating total mRNA from a bacterial cell. Double stranded cDNAs can then be prepared from the total mRNA, and subsequently inserted into a suitable plasmid or bacteriophage vector using any one of a number of known techniques. A gene encoding a MshC, MshD or MshA polypeptide can also be cloned using established polymerase chain reaction techniques in accordance with the nucleotide sequence information provided by the invention.

Another aspect of the invention relates to the use of an "anti-sense" isolated nucleic acid. As used herein, an "anti-sense" inhibition of endogenous production of a MshC, MshD or MshA molecule is carried out by administration or in situ generation of oligonucleotide probes or their derivatives which specifically hybridize (e.g. bind) under intracellular conditions, with the cellular mRNA and/or genomic DNA encoding a MshC, MshD or MshA polypeptide so as to inhibit expression of that protein or a constituent thereof, e.g. by inhibiting transcription and/or translation. The binding may be by conventional base pair complementarity, or, for example, in the case of binding to DNA duplexes, through specific interactions in the major groove of the double helix. In general, "anti-sense" therapy refers to the range of techniques generally employed in the art, and includes any therapy that relies on specific binding to oligonucleotide sequences.

An anti-sense construct of the present invention can be delivered, for example, as an expression plasmid which, when transcribed in the transformed cell, produces RNA which is complementary to at least a unique portion of the cellular mRNA that encodes a MshC, MshD or MshA polypeptide. Alternatively, the anti-sense construct is an oligonucleotide probe that is generated ex vivo and which, when introduced into the cell, causes inhibition of expression by hybridizing with the mRNA and/or genomic sequences encoding one of the subject MshC, MshD or MshA proteins. Such oligonucleotide probes are preferably modified oligonucleotides that are resistant to endogenous nucleases, e.g. exonucleases and/or endonucleases, and is therefore stable in vivo. Exemplary nucleic acid molecules for use as anti-sense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in anti-sense techniques have been reviewed, for example, by van der Krol et al. (1988) *Biotechniques* 6:958-976; and Stein et al. (1988) *Cancer Res* 48:2659-2668.

In addition, the oligomers of the invention may be used as reagents to detect the presence or absence of the target DNA or RNA sequences to which they specifically bind. Such diagnostic tests are described in further detail below.

This invention also provides expression vectors comprising a nucleotide sequence encoding a member of the families of MshC, MshD or MshA polypeptides and operably linked to at least one regulatory sequence. Operably linked is intended to mean that the nucleotide sequence is linked to a regulatory sequence in a manner that allows expression of the nucleotide sequence. Regulatory sequences are recognized in the art and are selected to direct expression of the peptide having an activity of a MshC, MshD or MshA polypeptide. Accordingly, the term regulatory sequence includes promoters, enhancers and other expression control elements. Exemplary regulatory sequences are described in Goeddel; Gene Expression Technology: Methods in Enzymology 185, Academic Press, San Diego, Calif. (1990). For instance, any of a wide variety of expression control sequences, sequences that control the expression of a DNA sequence when operatively linked to it, may be used in these vectors to express DNA sequences encoding mycothiol biosynthesis cysteine:glucosaminyl inositol ligase polypeptides. Such useful expression control sequences, include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered.

As will be apparent, the subject gene constructs can be used to cause expression of the subject MshC, MshD or MshA polypeptides in cells propagated in culture, e.g. to produce proteins or peptides, including fusion proteins or peptides, for purification.

This invention also pertains to a host cell transfected with a recombinant mshC, mshD or mshA gene in order to express a polypeptide having an activity of a MshC, MshD or MshA polypeptide. The host cell may be any prokaryotic or eukaryotic cell. For example, a MshC, MshD or MshA polypeptide may be expressed in bacterial cells such as *E. coli*, insect cells (baculovirus), yeast, or mammalian cells. Other suitable host cells are known to those skilled in the art.

Another aspect of the present invention concerns recombinant MshC, MshD or MshA polypeptides that have the ligase activity of a cysteine:glucosaminyl inositol ligase polypeptide, acetyltransferase activity of an acetyl-CoA:Cys-GlcN- Ins acetyltransferase polypeptide or glycosyltransferase activity of a MshA glycosyltransferase polypeptide, or which are naturally occurring mutants thereof. The term "recombinant protein" refers to a protein of the present invention that is produced by recombinant DNA techniques, wherein generally DNA encoding the MshC polypeptide, MshD polypeptide or MshA polypeptide is inserted into a suitable expression vector which is in turn used to transform a host cell to produce the heterologous protein. Moreover, the phrase "derived from," with respect to a recombinant gene encoding the recombinant MshC polypeptide, MshD polypeptide or MshA polypeptide, is meant to include within the meaning of "recombinant protein" those proteins having an amino acid sequence of a native MshC polypeptide, MshD polypeptide or MshA polypeptide, or an amino acid sequence similar thereto which is generated by mutations including substitutions and deletions of a naturally occurring MshC polypeptide, MshD polypeptide or MshA polypeptide of a organism.

The present invention further pertains to methods of producing the subject MshC, MshD or MshA polypeptides. For example, a host cell transfected with expression vector encoding one of the subject MshC, MshD or MshA polypeptides can be cultured under appropriate conditions to allow expression of the peptide to occur. The peptide may be secreted and isolated from a mixture of cells and medium containing the peptide. Alternatively, the peptide may be retained cytoplasmically and the cells harvested, lysed and the protein isolated. A cell culture includes host cells, media and other byproducts. Suitable media for cell culture are well known in the art. The peptide can be isolated from cell culture medium, host cells, or both using techniques known in the art for purifying proteins including ion-exchange chromatography, gel filtration chromatography, ultrafiltration, electrophoresis, and immunoaffinity purification with antibodies, such as invention antibodies, specific for particular epitopes of the subject MshC, MshD or MshA polypeptides.

Thus, a nucleotide sequence derived from the cloning of a MshC, MshD or MshA polypeptide of the present invention, encoding all or a selected portion of the protein, can be used to produce a recombinant form of the protein via microbial cellular processes.

The recombinant MshC, MshD or MshA polypeptide can be produced by ligating the cloned gene, or a portion thereof, into a vector suitable for expression in bacterial cells. Expression vehicles for production of a recombinant cysteine:glucosaminyl inositol ligase polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as E. coli.

A number of vectors exist for the expression of recombinant proteins in yeast. For instance, YEP24, YIP5, YEP51, YEP52, pYES2, and YRP17 are cloning and expression vehicles useful in the introduction of genetic constructs into S. cerevisiae (see, for example, Broach et al. (1983) in Experimental Manipulation of Gene Expression, ed. M. Inouye Academic Press, p. 83, incorporated by reference herein). These vectors can replicate in E. coli due the presence of the pBR322 ori, and in S. cerevisiae due to the replication determinant of the yeast 2 micron plasmid. In addition, drug resistance markers such as ampicillin can be used.

The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17. In some instances, it may be desirable to express the recombinant MshC, MshD or MshA polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

This invention further contemplates a method of generating sets of combinatorial mutants of the present MshC, MshD or MshA polypeptides, as well as truncation mutants, and is especially useful for identifying potential variant sequences (e.g. homologs) that are functional in ligation of cysteine to glucosaminyl inositol or a derivative thereof, functional in acetylation of Cys-GlcN-Ins by acetyl-CoA or functional in formation of GlcNAc-Ins. In a representative embodiment of this method, the amino acid sequences for a population of MshC, MshD or MshA polypeptide homologs are aligned. One effect of such alignment is to promote the highest homology possible. Such a population of variants can include, for example, homologs from one or more species, or homologs from the same species but which differ due to mutation. Amino acids that appear at each position of the aligned sequences are selected to create a degenerate set of combinatorial sequences. The presence or absence of amino acids from an aligned sequence of a particular variant is relative to a chosen consensus length of a reference sequence, which can be real or artificial. In order to maintain the highest homology in alignment of sequences, deletions in the sequence of a variant relative to the reference sequence can be represented by an amino acid space (*), while insertional mutations in the variant relative to the reference sequence can be disregarded and left out of the sequence of the variant when aligned.

Further expansion of the combinatorial library can be made by, for example, by including amino acids that would represent conservative mutations at one or more of the degenerate positions. Inclusion of such conservative mutations can give rise to a library of potential MshC, MshD or MshA sequences. Alternatively, amino acid replacement at degenerate positions can be based on steric criteria, e.g. isosteric replacement, without regard for polarity or charge of amino acid side chains. Similarly, completely random mutagenesis of one or more of the variant positions can be carried out.

In one embodiment, the combinatorial MshC, MshD or MshA library is produced by way of a degenerate library of genes encoding a library of polypeptides that each include at least a portion of potential MshC, MshD or MshA polypeptide sequences. For instance, a mixture of synthetic oligonucleotides can be enzymatically ligated into gene sequences such that the degenerate set of potential MshC, MshD or MshA nucleotide sequences are expressible as individual polypeptides, or alternatively, as a set of larger fusion proteins (e.g. for phage display) containing the set of MshC, MshD or MshA polypeptide sequences therein.

There are many ways by which the library of potential MshC, MshD or MshA homologs can be generated from a degenerate oligonucleotide sequence. Chemical synthesis of a degenerate gene sequence can be carried out in an automatic DNA synthesizer, and the synthetic genes then be ligated into an appropriate gene for expression. The purpose of a degenerate set of genes is to provide, in one mixture, all of the sequences encoding the desired set of potential MshC, MshD or MshA sequences. The synthesis of degenerate oligonucleotides is well known in the art (see for example, Narang, S A (1983) Tetrahedron 39:3; Itakura et al. (1981) Recombinant DNA, Proc 3rd Cleveland Sympos. Macromolecules, ed. A G Walton, Amsterdam: Elsevier pp. 273-289; Itakura et al. (1984) Annu. Rev. Biochem. 53:323; Itakura et al. (1984) Science 198:1056; Ike et al. (1983) Nucleic Acid Res. 11:477.

A wide range of techniques are known in the art for screening gene products of combinatorial libraries made by point mutations, and, for that matter, for screening cDNA libraries for gene products having a certain property. Such techniques will be generally adaptable for rapid screening of the gene libraries generated by the combinatorial mutagenesis of MshC, MshD or MshA homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene product was detected. Each of the illustrative assays described below are amenable to high throughput analysis as necessary to screen large numbers of degenerate sequences created by combinatorial mutagenesis techniques.

The invention also provides for reduction of the subject MshC, MshD or MshA polypeptides to generate mimetics, e.g. peptide or non-peptide agents, which are able to mimic binding of the authentic cysteine:glucosaminyl inositol ligase polypeptide, acetyl-CoA:Cys-GlcN-Ins acetyltransferase polypeptide or MshA glycosyltransferase polypeptide to a substrate molecule. Such mutagenic techniques as described above, as well as the thioredoxin system, are also particularly useful for mapping the determinants of a MshC, MshD or MshA polypeptide which participate in protein-protein interactions involved in, for example, binding of the subject cysteine:glucosaminyl inositol ligase polypeptide, acetyl-CoA: Cys-GlcN-Ins acetyltransferase polypeptide or MshA glycosyltransferase polypeptide to a substrate. To illustrate, the critical residues of a subject, for example, cysteine:glucosaminyl inositol ligase polypeptides which are involved in molecular recognition of substrate can be determined and used to generate cysteine:glucosaminyl inositol ligase-derived peptidomimetics that catalytically link cysteine or a cysteine derivative to glucosaminyl inositol or other derivative of glucosaminyl inositol. By employing, for example, scanning mutagenesis to map the amino acid residues of a particular cysteine:glucosaminyl inositol ligase polypeptide involved in binding to a substrate, peptidomimetic compounds (e.g. diazepine or isoquinoline derivatives) can be generated which mimic those residues that link cysteine. For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gama lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), beta-turn dipeptide cores (Nagai et al. (1985) Tetrahedron Lett 26:647; and Sato et al. (1986) J Chem Soc Perkin Trans 1:1231), and β-aminoalcohols (Gordon et al. (1985) Biochem Biophys Res Commun 126:419; and Dann et al. (1986) Biochem Biophys Res Commun 134:71). Similar methods are applicable to acetyl-CoA: Cys-GlcN-Ins acetyltransferase polypeptides and MshA glycosyltransferase polypeptides.

Purification of the Cys:GlcN-Ins ligase (SEQ ID NO: 2) from *M. smegmatis* proved difficult and many preliminary studies were needed to finally obtain sufficiently pure protein for N-terminal sequencing. The major problems encountered were multiple interconverting forms of the enzyme activity which eluted separately on chromatography and instability of the enzyme activity in purification buffers. The method which was eventually successful depended upon selection of the correct peak of activity at each stage of purification and intensive effort to complete the protocol before activity was lost.

Figure 3:
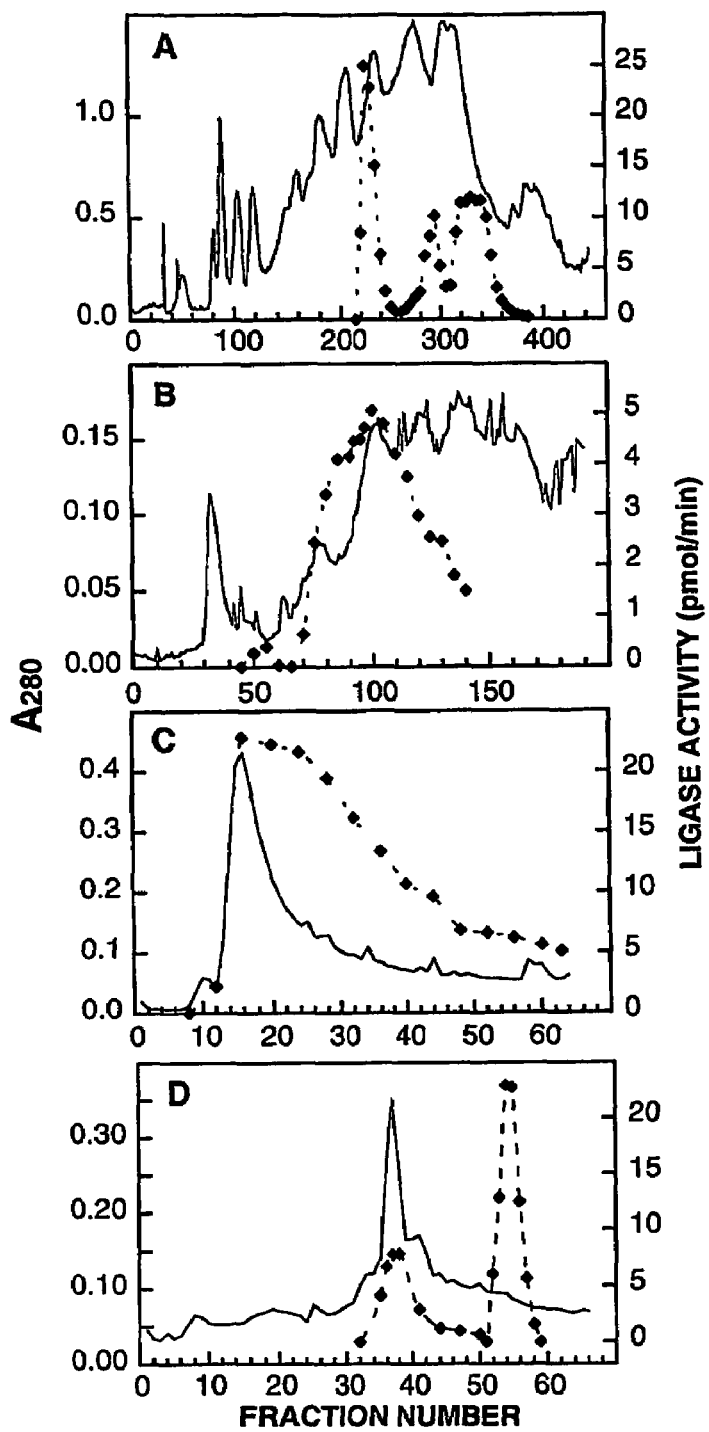
FIGS. 3A-D are graphs of the chromatographic profiles for purification of MshC.

The first purification step (Table 1) involved a 15-50% ammonium sulfate fractionation and this resulted in a 6.5-fold increase in specific activity with very little loss of protein. After desalting on G-25 this material was chromatographed on DEAE 650-M. The elution profile (FIG. 3A) revealed three major peaks of activity, the major portion of the activity residing in the first and third peaks. Experience revealed that the third peak was more readily susceptible to further purification and the central fractions from this peak were combined for chromatography on hydroxyl-apatite (FIG. 3B). Activity eluted primarily in one broad peak. The most active fractions were combined and bound to a Reactive Brown-10 dye affinity column at pH 6.5. After washing off unbound protein the column was eluted by increasing the pH to 8.0 over 5 column volumes (FIG. 3C). The activity eluted at pH 8 in a sharp but tailing peak.

The purification was monitored by SDS-PAGE and two closely migrating proteins of $M_r$~47000 were detected. The smaller protein was submitted for N-terminal amino acid sequencing as described in Example 4 and the sequence MQSWSAPAIPVVPGRGPALR (SEQ ID NO: 7) was obtained for the N-terminal 20 amino acids. When the smaller protein of SEQ ID NO: 7 was BLAST searched against the TIGR website of unfinished *M. smegmatis* genomic sequence, a 100% identity match was obtained with the N-terminal sequence for an open reading frame found on contig 3267 (corresponding to nucleic acids 1222384-1223620) and encoding a protein of 412 amino acid residues. A BLAST search of the N-terminal sequence (SEQ ID NO: 7) against the *M. tuberculosis* genome database (S. T. Cole et al. (1998) *Nature* 393, 537-544) on Tuberculist data base retrieved the sequence assigned as CysS2 (Rv2130c) (SEQ ID NO: 4) as the only one with significant N-terminal sequence correspondence and revealed a 70% identity and 80% positive homology between the N-terminal 20 amino acid residues of MshC of *M. smegmatis* (SEQ ID NO: 7) and those of *M. tuberculosis*. The full sequences for the two proteins are compared in FIG. 4.

Sequencing of the larger protein produced the sequence (G/S/M)(E/Q)HLKVDAMQSW(S/DP)APAIP (SEQ ID NO: 8), which overlaps that of the smaller protein. Comparison of the *M. smegmatis* upstream from the terminal Met (SEQ ID NO: 1) of the smaller protein detected a matching sequence SEHLKVDAMQSWSAPAIP (SEQ ID NO: 9) However, a search of Tuberculist database for a sequence matching SEQ ID NO: 9 found no match other than *M. tuberculosis* cysS2 and the upstream residues of this gene are not homologous to those of the *M. smegmatis* mshC gene. Thus, the ligase of *M. smegmatis* may be translated in two forms, one having an N-terminal extension of 8 residues starting with Ser and the other having Met as the N-terminal residue. Alternatively the larger protein may have been translated and partially processed by proteases.

Active enzyme fractions were utilized to estimate $K_m$ and $V_{max}$ values for Cys and GlcN-Ins from Eadie-Hofstee plots.

The invention ligase was found to have $K_m$ values of 40±3 and 72±9 μM for Cys and GlcN-Ins, respectively.

Confirmation that cysS2 of *M. tuberculosis* codes for MshC was obtained by using PCR to clone the gene into pRSETA. Sequencing of the cloned DNA verified that the cloning was accurate. The $His_6$-tagged protein was expressed in *E. coli* after induction with isopropyl-β-D-thiogalactopyranoside. Assay of the crude extract with 1 mM ATP, 0.1 mM Cys, and 50 μM GlcN-Ins gave 0.12 nmol $min^{-1}$ $mg^{-1}$ of ligase activity whereas analogous measurements on *E. coli* transformed with the blank vector yielded no measurable ligase activity (<0.01 nmol $min^{-1}$ $mg^{-1}$).

In another embodiment, the present invention provides mutants of mycothiol-producing bacteria that are constructed to be deficient in MSH production. One chemical mutant (I64) and two transposon mutants (Tn1 and Tn2) of *M. smegmatis* stably deficient in MSH production were isolated by screening for reduced levels of MSH content. The MSH content of transposon mutants Tn1 and Tn2 was found to be less than 0.1% that of the wild type strain $mc^2155$ and the MSH content of chemical mutant I64 was found to be 1% of the wild type strain. All three strains accumulated GlcN-Ins at a level 20-25-fold higher than the level found in the wild type parent strain. The L-cysteine: 1D-myo-inosityl 2-amino-2-deoxy-α-D-glucopyranoside ligase (MshC) activity was ≦2% that of the parent strain for the three mutant strains.

Members of the actinomycetes family, including the genus mycobacterium, exhibit innate resistance to many currently available antimicrobial drugs. This phenomenon is generally ascribed to their cell wall impermeability. In Examples 6-9 below, it is shown that MSH deficient mutants in which the mshC gene has been disrupted have increased sensitivity to a wide variety of agents including antibiotics, oxidizing agents and alkylating agents. Phenotypic analysis of the invention mutants revealed that these MSH deficient mutants possess increased sensitivity to free radicals and alkylating agents and to a wide range of antibiotics including erythromycin, azithromycin, vancomycin, penicillin G, rifamycin and rifampin. Conversely, the mutants possess at least 200-fold more resistance to isoniazid compared to wild type.

The demonstration that mycothiol depleted bacteria are sensitive to antibiotics is supported by earlier identification of the mycothiol-dependent detoxification system (G. L. Newton et al. (2000a), supra). The production of mycothiol in wild type species may account for the natural ability of actinomycetes and especially mycobacteria to resist a wide range of antibiotics.

Figure 6:
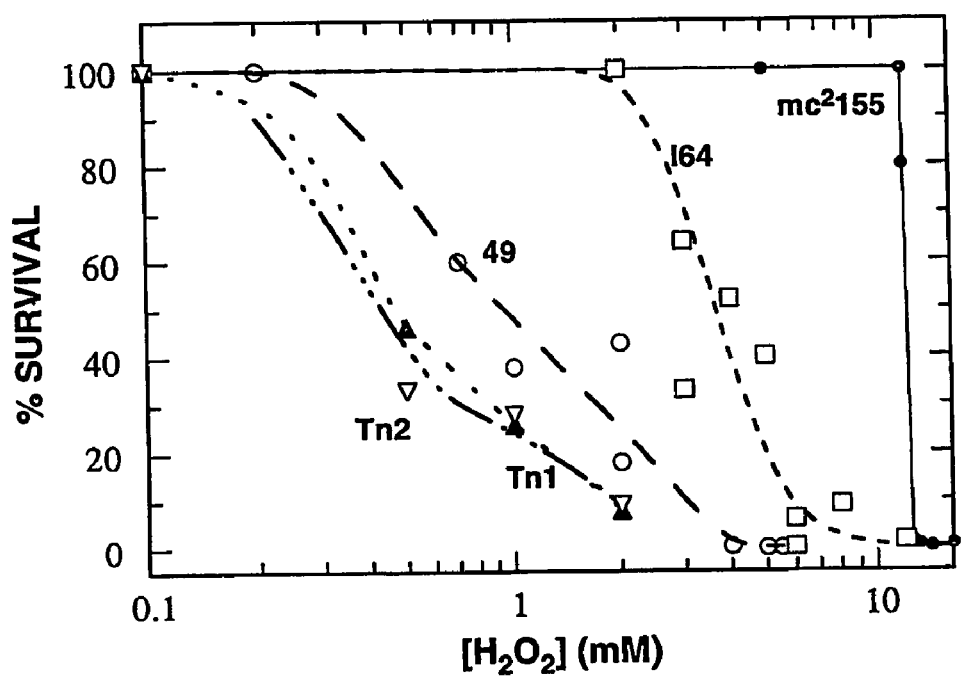
FIG. 6 is a graph showing the percent survival of the invention mutants as a function of peroxide concentration. Closed circles represent mc$^2$155, open squares—I64, open circles—49, upward closed triangles—Tn1, and downward open triangles represent Tn2.

It might be argued that one of the precursors to MSH is needed in an as yet unidentified process to confer resistance to peroxide (FIG. 6). However, the present studies show that mutants blocked at production of MshC still produce both GlcNAc-Ins and GlcN-Ins but are nevertheless highly sensitive to hydrogen peroxide. Thus, the possibility that these intermediates are associated with peroxide resistance is eliminated. This leaves the possibility that Cys-GlcN-Ins, rather than MSH, might be the key to peroxide resistance. However, Cys-GlcN-Ins is present in wild type *M. smegmatis* at almost undetectable levels (Anderberg, et al. (1998) J. Biol. Chem. 273:30391-30397), which makes it unlikely that Cys-GlcN-Ins could play a significant role in peroxide resistance. Thus, MSH, rather than one of its intermediates, remains as the key to antibiotic and peroxide sensitivity. Accordingly, the invention MSH minus mutants are generally more sensitive to peroxide and many antibiotics.

Although having increased sensitivity to various antibiotics, the MSH-deficient mutants of *M. smegmatis* described herein are extremely resistant to isoniazid, an antimycobacterial prodrug that needs to be activated inside mycobacteria to form a reactive intermediate of yet undetermined structure (K. Johnsson et al. (1991) J. Biol. Chem. 272:2834-2840). Since the MSH mutants have other low molecular weight thiols such as cysteine and coenzyme A in their reduced form (data not shown), these mutants cannot be described as free of low molecular weight thiols. Thus, the INH resistance is probably directly derived from lack of mycothiol, and not just a lack of low molecular weight thiol reductants in general. Thus, the results of the studies presented herein confirm and expand the correlation between mycothiol depletion and sensitivity of members of the actinomycetes family, including the genus mycobacterium to toxins and antibiotics, thus supporting the notion that inhibition of MSH metabolism, in particular inhibition of MshC, can be an attractive drug target for novel inhibitory compounds. In addition, an inhibitor of MshC activity in such bacteria can be used in combination with antibiotics, including those not currently in use against mycobacteria, in treatment of diseases that are associated with mycobacteria, such as Rifampin, rifamycin, erythromycin, azithromycin, vancomycin, and the like.

The isolation of MshD included an initial screening for isoniazid resistance in the production of a mutant library enriched in MSH-deficient mutants, as set forth below in Example 10. The library contained 3 mutants with <1% MSH per 200 tested. In an earlier study using chemical mutagenesis with N-methyl-N'-nitro-N-nitrosoguanidine and screening for slow growth on plates containing diamide one mutant was found to be devoid of MSH (mutant 49) in 415 tested (Newton, G. L., Unson, M., Anderberg, S., Aguilera, J. A., Oh, N. N., delCardayre, S., Davies, J., Av-Gay, Y., Fahey, R. C. (1999) *Biochem. Biophys. Res. Comm.* 255:239-244.). Thus, the present method appears to produce a 6-fold higher MSH-deficient mutant density which makes identification of actual MSH-deficient mutants by HPLC analysis more feasible.

The mshD::Tn5 mutant is useful for exploring various phenomena associated with the function of MSH. These include the exploration of the role of MSH in maintaining the cellular reducing environment in conjunction with mycothiol disulfide reductase (Patel, M. P., Blanchard, J. S. (1999) *Biochem.* 38:11827-11833.) and in the detoxification of alkylating agents and other cellular poisons (Misset-Smits, M., van Ophem, P. W., Sakuda, S., Duine, J. A. (1997) FEBS Lett 409:221-222; Newton, G. L., Av-Gay, Y., Fahey. R. C. (2000) *Biochem.* 35:10739-10746; Norin, A., Van Ophem, P. W., Piersma, S. R., Persson, B., Duine, J. A., Jornvall, H. (1997) Eur, J. Biochem. 248:282-289.). Since mshD::Tn5 accumulates all of the intermediates in the MSH biosynthetic pathway but does not produce MSH, comparison of the phenotype of this mutant with those of mutants blocked in other steps of MSH biosynthesis allows an assessment of whether or not the intermediates in MSH biosynthesis have other functions. But very key uses of mshD::Tn5 have already been demonstrated below in Example 10, as providing a source of Cys-GlcN-Ins and as used in identification of the mshD gene.

The role of mycothiol in the activation of the prodrug isoniazid in *M. smegmatis* was also examined. Mycothiol mutants in the mshA gene (Newton, G. L., Av-Gay, Y., Fahey. R. C. (2000) *J. Bacteriol.* 182:6958-6963; Newton, et al., 1999, supra.), the mshC gene (Rawat, M., Newton, G. L., Ko, M., Martinez, G. J., Fahey, R. C., Av-Gay, Y. (2002) *Antimicrob. Agents Chemother.*, in press.) and the mshD gene are all highly resistant to isoniazid. The transposon mutant mshD::Tn5 presumably must, like the wild-type strain, have intact isoniazid target genes and it produces substantial levels of a thiol, Cys-GlcN-Ins, having very similar structure to mycothiol. MSH is therefore specifically required, either directly or indirectly, for activation of isoniazid. This result is consistent with the earlier finding that restoring MSH content from 0% to 31% by complementation of chemical mutant 49 markedly reduced its isoniazid resistance (Newton, et al., 1999, supra).

The MshD acetyltransferase belongs to the large GCN5-related N-acetyltransferase family (Dyda, F., Klein, D. C., Hickman, A. B. (2000) *Annu. Rev. Biophys. Biomol. Struct* 29:81-103) but has some unusual characteristics. The sequence includes two separate regions with similarity to the pfam00583 domain characterizing acetyltransferases, with the C-terminal region having the highest degree of similarity (FIG. 8). Aside from the orthologs found in other actinomycetes the next most closely related proteins found in a GenBank search using Rv0819 are acetyltransferases which acetylate an N-terminal Ala residue of ribosomal proteins, such as the *E. coli* protein derived from the riml gene (Accession Number AAA97269). These proteins are half or less the length of MshD and a sequence match with higher sequence similarity occurs with the second acetyltransferase domain. These features suggest that the mshD gene is the product of a gene duplication and that it is the C-terminal domain that is involved in acetyl-CoA binding.

The mshB, mshC and mshD genes are widely separated in the *M. tuberculosis* genome and do not form a recognizable biosynthetic operon. It should be noted that Rv0818, a gene upstream to mshD (Rv0819), is a putative regulatory gene. In another complete actinomycete genome, *S. coelicolor* A3(2) (Sanger Institute, available on the worldwide web at sanger-.ac.uk/Projects/S_coelicolor), the mshB, mshC, and mshD genes are identified by homology to those of *M. tuberculosis* as SC9E12.11 (Accession no. CAC05756), SCI52.05c (Accession no. CAC36366), and SCD84.18c (Accession no. CAB88484), respectively. These genes are also widely dispersed throughout the genome.

The identification of the mycothiol biosynthesis genes establishes the basis for production of MSH biosynthesis gene knockouts in *M. tuberculosis*. Such knockouts can be used in determining the role of MSH in the virulence of *M. tuberculosis*.

As established in Example 11, the mshA gene in *M. smegmatis* is essential for the production of GlcNAc-Ins and thereby for the synthesis of MSH. The *M. tuberculosis* mshA gene, Rv0486, has been previously assigned by Campbell, et al., Biochem. J. 326:929-39, 1997 (who listed it as unknown protein MTCY20G9.12) as a member of glycosyltransferase family 4 in the CAZy database (displayed on the world wide web at http://afmb.cnrs-mrs.fr/CAZY/). This family includes a number of sucrose synthases, sucrose phosphate synthases (Sps), mannosyl transferases, and GlcNAc transferases. Homologs for MshA were found in sucrose and sucrose phosphate synthases and with the mannosyl transferase PimB (FIG. 11). FIG. 11 includes sequences for SpsA from *Anabaena* sp. PCC7120 (SEQ ID NO: 21) and PimB (Rv0557) from *M. tuberculosis* (SEQ ID NO: 22), with GenBank accession numbers AJ302071 and NP_215071, respectively. SpsA has 29% overall sequence identity with *M. tuberculosis* MshA whereas PimB has 24% identity. Cumino, et al., FEBS Lett. 517:19-23, 2002, have identified two highly conserved motifs present in the glucosyltransferase domains of sucrose-phosphate synthases and sucrose synthases, designated Box I and Box II as shown in FIG. 11. The *M. tuberculosis* MshA is identical to SpsA in 6 out of 12 Box I residues and in 17 out of 25 Box II residues. The first Gly of Box I is changed to Asp in *M. smegmatis* mutant 49. This results in complete loss of the ability to synthesize GlcNAc-Ins, GlcN-Ins and MSH in vivo, showing that this region is critical to the activity of MshA. The Box II domain contains the E-$X_7$-E signature (Geremia, et al., Biochem. J. 318:133-8 (1996).) universally found in the retaining glycosyl transferases of CAZy family 4 and for which the first residue, $E^{353}$ (*M. tuberculosis* numbering), has been shown to be essential for activity of the mannosyl transferase AceA from *Acetobacter xylinum*. (Abdian, P. L., et al., J. Biol. Chem. 275:40568-75 (2000).) PimB is less similar to SpsA than MshA but there are some additional residues identified by Kremer, et al. (Biochem. J. 363:437-47, 2002) as highly conserved in mannosyl transferases that are conserved in MshA and SpsA. These include $Lys^{278}$, which has also been shown to be essential for activity in AceA (Abdian, supra), as well as $Gly^{241}$, $Asp^{243}$ and $Arg^{273}$ for which no function has as yet been established (Kremer, supra.). The homology of MshA with known CAZy family 4 glycosyltransferases clearly indicates that MshA belongs to this group and is the glycosyltransferase required for biosynthesis of the pseudodisaccharide GlcNAc-Ins (FIG. 1).

*M. smegmatis* mutants deficient in MshC exhibit enhanced sensitivity to hydrogen peroxide, redox cycling agents, and certain antibiotics. As such, MshC is a useful target for new drugs directed against mycobacteria. As set forth below in Example 12, a further examination of the *M. tuberculosis* MshC ligase was performed by cloning, expressing, purifying, and characterizing the native form of the enzyme. Although active in the Cys:GlcN-Ins ligase assay, it was found to be inactive in a cysteinyl-tRNA ligase assay. The stoichiometry of the reaction catalyzed by the ligase was established experimentally (FIG. 17) and a preliminary examination was made of the enzyme kinetics, including a demonstration that the enzyme is not feedback inhibited by the product of the ligase reaction, Cys-GlcN-Ins or by MSH at their physiologic concentrations.

Mycobacterial proteins, when expressed in *E. coli*, often have solubility problems. MshC ligase is the largest protein among all the MSH biosynthetic enzymes identified to date. It consists of 414 residues and tends to aggregate as inclusion bodies when expressed as a N-terminal hexahistidyl tagged protein. The formation of AMP from ATP, along with Cys-GlcN-Ins (FIG. 18), is consistent with the view that the MshC enzyme action is a two step process in which the first step involves rapid activation of Cys to the Cys-adenylate (Cys-AMP) by the same mechanism as that catalyzed by cysteinyl-tRNA synthetase (Sareen, et al., 2002, infra).

As set forth in Example 12, in the MshC catalyzed reaction of GlcN-Ins to Cys-GlcN-Ins, the formation of AMP also includes the formation of pyrophosphate ($PP_i$) (see FIG. 1). Therefore, it is another embodiment of the invention to assay for the presence of $PP_i$ as a method of determining an effect of a compound on MshC. For example, in one embodiment, as set forth above, an inhibitor of MshC can be identified by contacting a candidate compound with a cysteine:glucosaminyl inositol ligase in the presence of a cysteine, a glucosaminyl inositol or a derivative thereof and ATP, under suitable conditions, and assaying for the generation of $PP_i$. Because $PP_i$ is a byproduct of the MshC catalyzed reaction, a substantial absence of $PP_i$ is indicative of a candidate compound that inhibits activity of the ligase. Such an assay for detection of the presence, creation or generation of $PP_i$ can include such assay techniques as fluoroscopy. Other assay techniques are well known to those of skill in the art. (See, for example, Upson et al. (1996) *Anal. Biochem.* 243:41-45; Nyren et al. (1994) *Anal. Biochem.* 220:39-45.)

In Example 12, the expression of the soluble protein was successfully achieved by cloning mshC in pACE expression vector with *M. smegmatis* as the host. The pACEmshC could also complement *M. smegmatis* mycothiol mutant I64, which is deficient in MshC ligase activity. The recombinant MshC ligase was purified 17.8-fold to homogeneity and characterized in some detail. The protein is an active monomer of 34 kD, containing 0.7 mol of Zinc per mol of enzyme with $K_m$ values for L-Cys and GlcN-Ins to be 70±15 μM and 280±43 μM, respectively. The results of Example 12 show that Cys-GlcN-Ins and AMP are produced in 1:1 stoichiometric ratio as the products of the ligase reaction. Nether the direct product, Cys-GlcN-Ins, nor the ultimate product, MSH, were found to feedback inhibit the MshC ligase enzyme. Additionally, MshC was confirmed to have ATP-dependent Cys:GlcN-Ins ligase activity only. The MshC ligase recognizes *E. coli* tRNA$^{cys}$ as its substrate with less than 2% the efficiency of the *E. coli* Cys-tRNA synthetase.

The multiple sequence alignment comparison of *M. tuberculosis* MshC and CysS (CysRS) with *E. coli* CysS in the light of recently solved crystal structure of *E. coli* CysRS, reveals that the active site of MshC also seems to be built from the canonical Rossman fold domain, as seen in other Class I tRNA synthetases. This domain is divided into two halves, 37-146 and 232-279 residues in *M. tuberculosis* MshC (which corresponds to residues 22-131 and 208-254 in *E. coli* CysS). The Rossman fold domain is interrupted by the connective polypeptide (CP) domain (147-231 in MshC, corresponding to 132-207 in *E. coli* CysS). Out of the first 57 residues of the CysRS CP domain, only 12 residues are conserved in MshC, while out of the last 19 residues of the CP domain, 14 residues are conserved, with this stretch highly conserved among MshC orthologs in *M. leprae, S. coelicolor, C. striatum* and *Thermobifida fusca*. MshC ortholog in *Thermobifida fusca* is 53% identical to that of *M. tuberculosis* found in 3.6 Mb sequence in TIGR unfinished microbial database. Interestingly, the *E. coli* CysRS CP domain (158-174 residues; corresponding to 178-194 of *M. tuberculosis* MshC) the region where the most important nucleotide of tRNA$^{cys}$, the discriminator base U73 interacts during aminoacylation (21, 22) is not conserved at all in MshC. Also, the C-terminal disordered anticodon binding domain (residues 403- to 461 in *E. coli* CysRS) is absent in MshC protein, which is thought to get ordered in 4 antiparallel helices upon tRNA$^{cys}$ binding, in the ribbon model of CysRS.

The crystal structure of *E. coli* CysRS also reveals that $Zn^{2+}$ plays an important role in the amino acid discrimination in favor of cysteine and against serine or alanine, without any editing function by the enzyme (Newberry, et al. (2002) *EMBO J.* 21, 2778-2787.). $Zn^{2+}$ has been proposed to accurately position the α-carboxylate of the substrate cysteine for the nucleophilic attack on ATP to form cys-adenylate (Cys-AMP). The amino acid residues proposed to be involved in the cysteine binding step (Cys28, Cys209, His234) are conserved in the MshC ligase and also in the *M. tuberculosis* CysRS gene (CysS) as well as in all orthologs of MshC identified in other species (FIG. 18). But, $Zn^{2+}$ has not been shown to be required for the catalytic action of *E. coli* or *M. tuberculosis* CysRS.

A directed knockout in *M. tuberculosis* of mshB showed surprising weakness to oxidants and antibiotics even though it produced at least 20% of the parent level of MSH (Buchmeier, et al., (2003) *Mol. Microbiol.* 47:1723-1732.). The compensating deacetylase activity in this mshB knockout in *M. tuberculosis* was proposed to be the mycothiol S-conjugate amidase Rv1082, a homolog of mshB (Rv1170). *M. smegmatis* mutants in mshA (Newton, et al. (2003), submitted) and mshC (Rawat, et al., (2002), *Antimicrob. Agents Chemother.* 46:3348-3355) have been shown to be devoid of mycothiol and thus these genes are the best choices for testing the essentiality of mycothiol in *M. tuberculosis*. In studies with *M. smegmatis* we have found mycothiol mutants with <5% mycothiol in mshA, mshC and mshD. Example 13 below shows that mshC and mycothiol are indeed essential for *M. tuberculosis* Erdman, and mshC is provided as a potential drug target. The essentiality of mycothiol in *M. tuberculosis* Erdman contrasts with the requirement of mycothiol in *M. smegmatis*. In *M. smegmatis* complete mycothiol mutants have been isolated which indicates that this organism is much less sensitive than *M. tuberculosis* to oxidants encountered during normal metabolism in laboratory culture. Mycothiol appears important for the antioxidant defenses of *M. tuberculosis* in laboratory culture and may be even more critical to the organism during times of oxidative stress such as intracellular colonization of the pulmonary macrophage.

A knockout of mshC was attempted by allelic exchange via efficient mycobacteriophage transduction (Bardarov, et al. (2002), *Microbiol.*, 148:3007-17) which gave no surviving transformants with the mshC gene altered. All hygromycin resistant transformants examined had parental mycothiol levels and were deemed to be spontaneous hygromycin mutants. One interpretation of these results is that mshC or some gene downstream of mshC may be essential.

The following examples are intended to illustrate but not limit the invention.

EXAMPLE 1

Identification of MshC

Bacterial culture. *M. smegmatis* strain mc$^2$155 was grown in Middlebrook 7H9 broth (Difco Laboratories) supplemented with 0.05% TWEEN™ 80 (Fisher) and 0.4% glucose (Fisher) at 37° C. and 250 rpm. After 28 h of cultivation, the bacterial cells were collected by centrifugation at 8000 g for 15 min. The cell pellets were stored at −70° C. until used.

Reagents. MSH was isolated from *M. smegmatis* and derivatized with monobromobimane (mBBr, Molecular probes) to form the monobromobimane derivative of mycothiol (MSmB) and purified as described earlier (G. L. Newton et al. (1993) *J. Bacteriol.* 175, 2734-2742). GlcN-Ins was prepared by hydrolyzing MSmB quantitatively, with purified *M. smegmatis* mycothiol S-conjugate amidase, as previously described (G. L. Newton et al. (2000) *Biochemistry* 35, 10739-10746). CySmB-GlcN-Ins was purified by preparative high performance liquid chromatography (HPLC), after acid hydrolysis of MSmB, as described earlier (S. Anderberg et al. (1998) supra).

EXAMPLE 2

Assays. A minor modification of the protocol described by Anderberg et al (supra) was used for routine measurement of ATP-dependent ligase activity. The enzyme activity was assayed in a final volume of 25 μL containing 12.5 μL of the ligase in different dilutions, 50 μM GlcN-Ins, 100 μM Cys (Calbiochem), 1 mM ATP (Sigma), 1 mM $MgCl_2$ (Fisher), 1 mM DTT (Calbiochem), 25 mM N-2-hydroxyethylpiperazine-N'-2-ethanesulfonic acid (HEPES) (Sigma), pH 7.5, and 35 μM each of the protease inhibitors (Sigma) N-α-p-tosyl-L-phenylalanylchloromethyl ketone and N-α-p-tosyl-L-lysinechloromethyl ketone. The mixture was incubated at 37° C. for 30 min. The assay was terminated by addition of 25 μL of 8 mM mBBr in acetonitrile and heating the mixture at 60° C. for 5 min to derivatize the thiols. The derivatization was quenched with the addition of 150 μl of 10 mM methanesulfonic acid and vortexing. HPLC analysis of CySmB-GlcN-Ins and CySmB was carried out by HPLC using a Beckman Ultrasphere IP (250×4.6 mm) analytical column fitted with a Brownley OD-GU 5 μ C-18 cartridge using the following linear gradients: 0 min., 100% A (0.1% TFA in water); 10 min, 100% A; 30 min, 80% A; 33 min, 100% B (7.5% methanol in acetonitrile); 36 min, 100% B; 38 min, 100% A; 60 min, 100% A (reinjection). The flow rate was 1 mL/min. and the fluorescence detection was accomplished with a 370 nm excitation filter and a 418-700 nm emission filter. The $V_{max}$ and $K_m$ values were calculated by least-squares analysis of Eadie-Hofstee plots with initial rate data using KaleidaGraph 3.5 (Synergy Software). With [ATP]=1 mM and [GlcN-Ins]=300 μM, the apparent $K_m$ for Cys (5-400 μM, n=8) was determined to be 40±3 μM and $V_{max}$ was 83±3 nmol min$^{-1}$ mg$^{-1}$. For [ATP]=1 mM and [Cys]=100 μM the apparent $K_m$ for GlcN-Ins (5-600 μM, n=7) was 72±9 μM and $V_{max}$ was 90±7 nmol min$^{-1}$ mg$^{-1}$ Protein concentration was measured by the method of Bradford (M. M. Bradford. (1976) *Anal. Biochem.* 72, 248-254) using BSA as standard.

EXAMPLE 3

Purification of Ligase. All operations were carried out at 4° C. in the presence of 3 mM 2-mercaptoethanol unless stated otherwise. mc$^2$ 155 cells (182 g wet wt.) were suspended in 780 mL of 50 mM HEPES pH 7.5 in the presence of 35 μM of the protease inhibitors N-α-p-tosyl-L-phenylalanylchloromethyl ketone and N-α-p-tosyl-L-lysinechloromethyl ketone. The cells were disrupted by ultrasonication (Branson Sonifier 200) in an ice bath. The cell debris was removed by centrifugation at 100000 g for 1 h at 4° C. A solution of saturated ammonium sulfate (Fisher) was added to the supernatant to 15% and the mixture allowed to stand on ice for 2 h. After centrifugation at 28000 g for 30 min, additional SAS was added to the supernatant to 50% saturation and the mixture stored overnight at 4° C. After centrifugation at 28000 g for 30 min the protein pellet (32 g) was resuspended in 500 mL of 50 mM HEPES pH 7.5 and was desalted by passing it through Sephadex G-25 column (7.5×36 cm). The collected eluent (550 mL) was applied on a Toso Haas DEAB 650-M column (5.2×26 cm, 500 mL) equilibrated with 50 mM HEPES, pH 7.5. The enzyme was eluted with a linear gradient of 0-0.4 M NaCl in 16 column volumes of the buffer at 600 mL/h. (FIG. 3A) The fractions (#315-350) containing the third peak of enzyme activity were combined (670 mL) and were diluted three-fold with Milli-Q water to lower the salt concentration. The diluted solution was applied to a hydroxyl apatite column (Bio-gel HTP from BioRad; 2.6×26 cm) at 120 mL/h, which was pre-equilibrated with 10 mM potassium phosphate (Fisher) buffer pH 6.8 containing 100 mM NaCl. The bound proteins were eluted at 240 mL/h with a linear gradient of 10-100 mM phosphate (100-0 mM NaCl) in 20 column volumes. The activity in fractions (#75-125) was collected (800 mL) (FIG. 3B) and diluted to 1800 mL with Milli-Q water to lower the salt concentration. The pH was adjusted to 6.4 with 1 M potassium dihydrogen phosphate. The diluted material was applied to a Reactive Brown 10 dye affinity column (Sigma, 1.5×11 cm, 20 mL) at 60 mL/h pre-equilibrated with 50 mM potassium phosphate buffer pH 6.5 and washed with buffer until no absorption was evident in the effluents (200 mL, 120 mL/h). The ligase was eluted with 50 mM phosphate buffer pH 8.0 at a flow rate of 120 mL/h. The fractions containing optimal ligase activity (#12-64) were collected (104 mL) (FIG. 3C). The protein was concentrated by adding solid ammonium sulfate to 80% saturation and allowing precipitation to continue on ice for 2 h. It was collected by centrifugation at 28000 g for 30 min at 4° C. and resuspended in 50 mM HEPES pH 7.5 containing 150 mM NaCl and 3 mM 2-mercaptoethanol. This was loaded on a Sephadex G-100 column (Pharmacia, 1.5×95 cm, 170 mL) and eluted with the same buffer. The active fractions were collected (2 mL each) (FIG. 3D) and analyzed for purity on 12.5% sodium dodecyl sulfate polyacrylamide gel electrophoresis (SDS-PAGE). Purified protein thus obtained was stored at 4° C. for further characterization.

The results of this multi-step purification are shown in Table 1 below:

TABLE 1

Purification of *M. smegmatis* Cys:GlcN-Ins ligase (MshC)

| Step | protein (mg) | total activity (nmol min$^{-1}$) | specific activity (nmol min$^{-1}$ mg$^{-1}$) | Yield (%) | Purify factor |
|---|---|---|---|---|---|
| crude extract | 9660 | 227 | 0.023 | (100) | (1) |
| 15-50% SAS | 6900 | 1030 | 0.15 | 454 | 6.5 |
| DEAE ion exchange | 847 | 465 | 0.55 | 205 | 24 |
| hydroxyl apatite | 90 | 300 | 3.3 | 132 | 139 |
| Reactive Brown 10 Affinity chromatography | 15 | 150 | 10 | 66 | 435 |
| gel filtration G-100 | 0.2 | 10.8 | 54 | 4.8 | 2350 |

The first purification step involving a 15-50% ammonium sulfate fractionation resulted in a 6.5-fold increase in specific activity with very little loss of protein. After desalting and chromatography on DEAE 650-M, the elution profile (FIG. 3A) revealed three major peaks of activity, the major portion of the activity residing in the first and third peaks. Experience revealed that the third peak was more readily susceptible to further purification and the central fractions from this peak were combined for chromatography on hydroxyl-apatite (FIG. 3B) with activity eluting primarily in one broad peak. The most active fractions when combined and bound to a Reactive Brown-10 dye affinity column at pH 6.5 and at pH 8 in a sharp but tailing peak.

The purification was monitored by SDS-PAGE, which suggested that only a few proteins of varying size were present after chromatography on the Brown-10 column. The peak activity from this column was pooled, precipitated with ammonium sulfate, and taken up in HEPES buffer pH 7.5 for chromatography on Sephadex G-100. The activity eluted in two peaks corresponding to $M_r$~150000 and ~89000 (FIG. 3D), the second peak exhibiting highest specific activity.

Each fraction of the second peak was concentrated and examined by SDS-PAGE. SDS PAGE gels showed purification of MshC. The gel was prepared as follows: (lane 1, 7 and 8) Bio-Rad Broad Range molecular mass standards; (lane 2) crude cell free extract; (lane 3) 15-50% saturated ammonium sulfate extract; (lane 4) pooled fractions #315-350 from DEAE-M chromatography; (lane 5) pooled fractions #75-125 from hydroxyl apatite chromatography; (lane 6) pooled fractions #12-64 from Reactive Brown 10 chromatography; (lane 9) Sephadex G-100 fraction 50 (lacking ligase activity) and (lanes 10-15) fractions #52-57, respectively, with purified ligase. Two closely migrating proteins of $M_r$~47000 were detected (in lanes 10-14), with the larger protein rich in the earlier fractions (lanes 10 and 11) and the smaller protein dominant in the later fractions (lanes 13 and 14).

EXAMPLE 4

Protein sequencing. Amino acid sequencing of the two active ligase proteins (obtained in Example 3 above) was performed after electroblotting the two bands of active ligase from 12.5% SDS-PAGE to a polyvinylidene difluoride membrane. The N-terminal amino acid sequence was determined on an Applied Biosystems Model 494 Procise gas phase protein sequencer at the UCSD Department of Biology Protein Sequencing Facility.

EXAMPLE 5

Cloning of the *M. tuberculosis* MshC Ligase.

Confirmation that cysS2 of *M. tuberculosis* codes for MshC was obtained by using PCR to clone the gene into pRSETA. *M. tuberculosis* H37Rv genomic DNA (kindly provided by Y. Av-Gay, University of British Columbia) was employed to amplify the mshC gene by PCR using the primers:

```
DF-1
(5'-
GCGGGATCCATGCAGTCGTGGTATTGCCC-3')  (SEQ ID NO: 10)
and

DR-1
(5'-
CCAAGCTTCTACAGGTCCACCCCGAGCA-3')  (SEQ ID NO: 11)
and
```

Platinum Pfx DNA polymerase (Gibco BRL). The PCR product was cloned into the BamH I/Hind III (New England Biolabs) sites of pRSETA (Invitrogen) using T4 DNA ligase (Gibco BRL). The expression plasmid was transformed into *E. coli* TOP10F' (Invitrogen) and the presence of the insert verified by cleavage with BamH I and Hind III. The MshC ligase, which contains an N-terminal $His_6$ extension, was expressed in *E. coli* BL21 (DE3) plys S (Invitrogen) with induction overnight by 0.5 mM isopropyl-α-D-thiogalactopyranoside (Fisher) at 20° C. Sequencing of the cloned DNA verified that the cloning was accurate. The $His_6$-tagged protein was expressed in *E. coli* after induction with isopropyl-α-D-thiogalactopyranoside. Assay of the crude extract with 1 mM ATP, 0.1 mM Cys, and 50 μM GlcN-ins gave 0.12 nmol $min^{-1}$ $mg^{-1}$ of ligase activity whereas analogous measurements on *E. coli* transformed with the blank vector yielded no measurable ligase activity (<0.01 nmol $min^{-1}$ $mg^{-1}$).

EXAMPLE 6

Mutagenesis of *M. smegmatis* $mc^2155$

Strains and chemicals. *Escherichia coli* DH5α (F⁻ recA1 hsdR17 thi-1 gyrA96 supE44 endA1 relA1 recA1 deoR Δ(lacZYA-argF)U169 (φ80 lacZ ΔM15) was grown in Luria-Bertani (LB) medium at 37° C. Streptomycin (50 μg/ml), kanamycin (100 μg/ml) ampicillin (100 μg/ml) and hygromycin (150 μg/ml) were used when required. *M. smegmatis* $mc^2155$ was kindly provided by Dr. W. R. Jacobs and was grown in 7H10 medium with 10% OADC and 0.05% TWEEN™-20 (PBT). Kanamycin (25 μg/ml) and hygromycin (50 μg/ml) were used when required. Chemicals were purchased from Sigma Chemicals (St. Louis, Mo.).

I. Preparation of Chemical Mutants Lacking MshC Gene Activity

Chemical mutagenesis of *M. smegmatis* $mc^2155$ with N-Methyl-N'-nitro-N-nitrosoguanidine (MNNG; Aldrich) to produce mutant I64 was performed as described by Newton et al. (1999) (*Biochem. Biophys. Res. Commun.* 255:239-244) except that diamide was not added to the plating medium. *M. smegmatis* strains, $mc^2155$ and I64 were grown at 37° C. while the transposon mutants were grown at 42° C.

A grided library of 1600 *M. smegmatis* $mc^2155$ clones which were subjected to an initial screen for MSH content using a blotting immunoassay protocol (M. D. Unson et al. (1998) *J. Immunol. Methods*, 214:29-39). A total of 56 colonies were selected for further examination. These were grown in liquid culture and the cells extracted for HPLC analysis of MSH content. Although several mutants appeared to have reduced MSH content, one mutant, strain I64, was found to have significantly lower MSH content (see Table 2) and was selected for further study.

II. Preparation of Tn611 Transposon Mutants Lacking MshC Activity

The transposon mutagenesis of *M. smegmatis* $mc^2155$ cells was performed as described by Guilhot et al., 1994 (*J. Bacteriol.* 176:535-539) using the thermosensitive plasmid pCG79 containing Tn611. The plasmid was electroporated into *M. smegmatis* and transformants were selected on PBT media supplemented with kanamycin at 30° C. Randomly chosen clones were grown at 30° C. for 72 h in 5 ml of 7H9 medium supplemented with kanamycin. These cultures were used to inoculate antibiotic-free 7H9 media and the inoculated cultures were grown for 24 hours at 39° C. Various dilutions were then plated on PBT medium supplemented with kanamycin and incubated at 39° C.

III. Molecular Biology Manipulations

Genomic DNA was isolated from *M. smegmatis* culture according to Jacobs et al., (supra). Standard recombinant DNA techniques and Southern blots were carried out as described by Sambrook et al., 1989 (*Molecular cloning: a laboratory manual* $2^{nd}$ ed. Cold Spring Harbor Laboratory Press. Cold Spring Harbour, N.Y.). *M. smegmatis* electroporation was performed as described by Snapper et al., 1988 (*Proc. Natl. Acad. Sci USA*. 85:6987-6991).

Using the above mutation procedures, a transposon mutant library in *M. smegmatis* consisting of 10,000 mutants was created using the thermo sensitive plasmid pCG79 (Perez et al. (1998) *Methods Mol. Biol.* 101:187-198). One thousand representative mutants were picked, sorted, and cultured individually in ELISA plates. The mutants were screened by ELISA utilizing a polyclonal antibody against MSH (M. D. Unson et al. (1999) *J. Clin. Microbiol.* 214:29-39). Three independent MSH deficient mutants were identified as shown in Table 2 below:

TABLE 2

|  | $mc^2155$ | I64 | Tn1 | Tn2 | Tn3 |
|---|---|---|---|---|---|
| Growth on 50 μg/ml INH | − | + | + | + | + |
| A 405 nm [a] | 1.394 | 0.396 | 0.256 | 0.278 | 0.286 |
| A 600 nm | 0.208 | 0.405 | 0.279 | 0.320 | 0.288 |
| Signal/Growth [b] | 4.629 | 0.978 | 0.918 | 0.869 | 0.993 |
| Growth at 42° C. on INH | ND | ND | + | + | − |

[a] Absorbance of the alkaline phosphatase product in the MSH- capture ELIZA assay.
[b] proportional to the MSH content of the cells.

Only two of these mutants (Tn1 and Tn2) were found to stably incorporate the Tn611 transposon into the genome as judged by Southern analysis. If the insertion is in the genome, three bands are expected when using IS6100 as a probe for hybridization to PstI digested genomic DNA of the mutants; two identical to those in the parent plasmid (0.9 kb and 2 kb) and a third one of a different size that in the present case turned out to be of 4.5 kb in size for Tn1 and Tn2. A faint band of 4.5 kb was also observed in initial Southern hybridization examining Tn3 genomic DNA. However, subsequent experiments revealed that the transposon insertion in Tn3 is not stable as this mutant failed to grow at 42° C. on selective plates (Table 2). Thus, phenotypic analysis of the Tn3 mutant was aborted. Southern hybridization with IS6110-labelled probe also confirmed that only one transposon was present in the chromosome for each of the two transposon mutants Tn1 and Tn2.

EXAMPLE 7

Assay of MSH and MSH Precursors in MshC Deficient Mutants.

The invention mutants were also analyzed for MSH and amine-intermediate levels during exponential growth using sensitive HPLC assays. Labeling of cell extracts with monobromobimane (mBBr) to determine thiol content was performed with modifications to previously published protocols (Anderberg et al., supra and G. L. Newton et al., 1996, supra). Cell pellets from 3 ml culture were resuspended in 0.5 ml of warm 50% acetonitrile-water containing 2 mM mBBr (Calbiochem, San Diego, Calif.), and 20 mM HEPES, pH 8. The suspensions were incubated for 15 min at 60° C. water bath and then cooled on ice. A 2-5 µl aliquot of 5M HCl or 5M trifluoracetic acid (TFA) was added to produce a final acidic pH.

Control samples were extracted with 0.5 ml of warm 50% acetonitrile-water containing 5 mM NEM and 20 mM HEPES, pH 8. The suspensions were incubated for 15 min at 60° C. and then cooled on ice. After addition of mBBr to 2 mM the solution was incubated for a second time for 15 min at 60° C. The control samples were cooled but not acidified. Cell debris was pelleted in each sample by centrifugation (5 min, 14,000×g) in a microcentrifuge.

HPLC analysis of thiols was carried out by injecting 25 µl of a 1:4 dilution of the samples in 10 mM HCl onto a Beckman ULTRASPHERE™ ODS 5µ (250 mm×4.6 mm) column. Elution was accomplished with 0.25% glacial acetic acid pH 3.6 (Buffer A) and 95% methanol (Buffer B) using the following gradient: 0 min; 10% B, 15 min; 18% B, 30 min; 27% B, 32 min; 100% B, 34 min; 10% B, and 60 min; 10% B, (reinjection). The flow rate was 1 ml per min. and the fluorescence detection was as previously described.

TABLE 3

| M. smegmatis Strain | GlcN-Ins (µmoles/gm dry weight) | Ligase specific activity (nmole/min/mg protein) | Mycothiol (µmoles/gm dry weight) |
|---|---|---|---|
| mc$^2$155 | 0.1 | 0.320 ± 0.010 | 10.0 |
| I64 | 2.5 | 0.004 ± 0.001 | 0.1 |
| Tn1 | 2.6 | 0.004 ± 0.002 | <0.004 |
| Tn2 | 1.9 | 0.004 ± 0.002 | <0.003 |

EXAMPLE 8

Assay of Ligase Activity Assay in MshC Deficient Mutants.

The ligase specific activity was estimated by the ATP-dependent formation of Cys-GlcN-Ins catalyzed by *M. smegmatis* cell-free extracts prepared and analyzed in triplicate as described in Example 2 above (Anderberg et al., supra) except that centrifugation of the extracts was conducted in a microcentrifuge for 5 min at 14,000×g. As shown by the results of these studies summarized in Table 3 of Example 7, all three mutants and strain I64 were found to be deficient in MSH and overproduced GlcN-Ins by about 25-fold.

In all cases the content of Cys-GlcN-Ins, the ligase product, was undetectable (<0.002 mmol/gm dry weight). A block in Cys:GlcN-Ins ligase activity would be expected to result in an accumulation of GlcN-Ins. These findings suggest that the ligase gene (mshC) has been interrupted in the transposon mutants. In addition, the results clearly show that Tn1 and Tn2 are similar to the chemical mutant I64, all having a very low level of MshC activity in crude extracts (Table 3 of Example 7).

EXAMPLE 9

Toxicity Studies and Antibiotic Sensitivity Tests in Mutants.

It has previously been shown that MSH takes part in detoxification of alkylating agents. Consequently, mutants lacking MSH should then be more susceptible to these agents. The fluorescent alkylating agent, mBBr, selectively reacts with cellular thiols and mycobacteria possess a mycothiol-dependent amidase that can detoxify mycothiol-monobimane conjugates (G. L. Newton et al (2000a) supra.) Lack of mycothiol would presumably result in increased sensitivity to this toxin.

To test this hypothesis, Tn1, Tn2, and I64 were grown on PBT plates supplemented with increasing amounts of the alkylating agents mBBr, iodoacetamide, and 1-chloro-2,4-dinitrobenzene (CDNB). The alkylating agents were poured into the molten agar. Table 4 below shows the minimum inhibitory concentrations of various alkylating agents against mc$^2$155 and MSH$^-$ mutants.

TABLE 4

| | Minimum Inhibitory Concentration (µg/ml) | | | |
|---|---|---|---|---|
| Agent | Wild Type | I64 | Tn1 | Tn2 |
| CDNB | 0.05-0.075 | 0.075 | 0.025 | 0.025 |
| mBBr | 0.1 | 0.075 | 0.025 | 0.025 |
| Iodoacetamide | 0.05 | 0.025 | 0.025 | 0.010 |
| Diamide | 10< | 5 | <1 | <1 |

The transposon mutants Tn1 and Tn2 were 4-fold more sensitive to mBBr as compared to wild type mc$^2$155. The chemical mutant, I64, which has 1% of the wild type MSH content, was also more susceptible to mBBr, but not to the same extent as the transposon mutants, which have no detectable MSH. Iodoacetamide is another alkylating agent that is commonly used to derivatize proteins. Mutants I64 and Tn1 were two-fold more sensitive to iodoacetamide, and mutant Tn2 5-fold more sensitive, as compared to the wild type mc$^2$155 strain. Tn1 and T2 were also more sensitive to CDNB (2-3 fold), another alkylating agent and a glutathione S-transferase substrate, as compared to wild type mc$^2$155. In the case of the thiol-specific oxidant, diamide, which readily penetrates cells and oxidizes thiols to disulfides. (N. S. Kosower et al., Meth. Enzymol. 251:123-133), a greater than 10-fold increase in sensitivity of the transposon mutants was observed. Sensitivity of I64 to diamide was doubled compare to the wild type. In summary, the transposon mutants lacking mycothiol were more susceptible to alkylating agents than wild type *M. smegmatis* mc$^2$155 although the degree of susceptibility depended on the toxin tested.

Peroxide sensitivity was determined by incubating cells ($2.5 \times 10^7$ per ml) at 37° C. in Middlebrook 7H9 medium with 0.4% glucose and 0.05% TWEEN® 80 containing hydrogen peroxide at the desired level for 2 hours with shaking. Cells were diluted in fresh medium and plated on 7H10 agar. Colonies were counted when they achieved a diameter of 1-2 mm, which required 4-5 days for the wild type strain and up to 10 days for MSH-deficient mutant strains.

To determine sensitivity to redox cycling agents, disk assays were performed. Briefly, cells were grown to mid-log phase and a lawn of cells was plated onto PBT or LB plates supplemented with appropriate antibiotics. Various amounts of redox-cycling agents plumbagin, and antibiotics menadione and nitrofurantoin were added to the disk in 10 μl volume and allowed to dry. The disks were placed onto the lawn of cells and incubated 2-3 days.

The results of FIG. 6 show that Tn1 and Tn2 are about 10 times more sensitive to hydrogen peroxide than the wild type strain. Tn1 and Tn2 were unable to tolerate as little as 1 MM $H_2O_2$ while the wild type strain can survive at 10 mM $H_2O_2$. Tolerance of Strain I64 is intermediate between wild type $mc^2155$ and the transposon mutants in its susceptibility to peroxide stress (FIG. 6).

When the oxidative stress is in the form of redox-cycling agents that increase the superoxide concentration in the cell, a similar pattern is seen. As seen in the results summarized in Table 5 below, Tn1 and Tn2 mutants are markedly more sensitive to plumbagin and the antibiotic nitrofurantoin than the wild type strain.

TABLE 5

| Agent concentration | Zone of Inhibition (mm) | | | |
|---|---|---|---|---|
| [μmol] | Wild Type | I64 | Tn1 | Tn2 |
| 0.01 Plumbagin | 13.5 ± 0.5 | 13.3 ± 1.9 | 23.0 ± 1.2 | 23.0 ± 1.0 |
| 0.005 Plumbagin | 11.0 ± 1.0 | 9.3 ± 0.9 | 17.0 ± 0.6 | 15.0 ± 0.0 |
| 0.5 Menadione | 19.7 ± 0.9 | 26.7 ± 0.9 | 31.3 ± 1.3 | 16.4 ± 1.9 |
| 0.1 Menadione | 9.7 ± 0.3 | 8.7 ± 0.7 | 20.7 ± 3.8 | 15.3 ± 2.0 |
| 1.0 Nitrofurantoin | 6.0 ± 0.6 | 8.7 ± 0.3 | 14.0 ± 2.7 | 35.0 ± 3.6 |
| 0.5 Nitrofurantoin | 4.7 ± 0.3 | 5.0 ± 0.6 | 10.7 ± 2.6 | ND |

The results for the transposon mutants with menadione showed no consistent pattern and are therefore inconclusive. Mutant I64, which contains a low level of MSH, is less sensitive to the above agents, undergoing a significant increase in the zone of inhibition only in the case of 0.5 μmol menadione.

Results of Antibiotic Sensitivity Tests

Since the invention mutants are devoid of MSH they cannot carry out MSH-dependent detoxification via the pathway involving mycothiol S-conjugate amidase activity (G. L. Newton et al 2000a, supra). To test the hypothesis that MSH is involved in protection against antibiotics, the antibiotic sensitivity of the transposon and chemical mutants to a variety of antibiotics, including erythromycin, azithromycin, vancomycin, and penicillin G, was tested by application of 0, 2 μg, 7 μg, 8 μg, 32 μg, 125 μg or 250 μg of antibiotic to the disks. The results of these tests summarized in Table 6 below show that the transposon mutants Tn1 and Tn2 and the chemical mutant I64 are 3-16 fold more sensitive than the parent strain ($mc^2155$) to the antibiotics erythromycin, azithromycin, vancomycin, and penicillin G.

TABLE 6

| | Minimum Inhibitory Concentration (μg/ml) | | | |
|---|---|---|---|---|
| Drug | $mc^2155$ | I64 | Tn1 | Tn2 |
| Isoniazid | 2 | 32 | >250 | >250 |
| Erythromycin | 125 | 32 | 7.8 | 32 |
| Azithromycin | 7.8 | 2 | 2 | 2 |
| Vancomycin | 6 | 1 | 2 | 1.5 |
| Penicillin G | >250 | >250 | 32 | 32 |
| Rifampin | 32 | 32 | 7.8 | 7.8 |
| Rifamycin | 32 | 32 | 7.8 | 2 |

Examination of drugs used to treat *M. tuberculosis* infection, rifamycin and rifampin, revealed that all the transposon mutants are more sensitive to these drugs than the chemical mutant I64 (Table 6), but no significant difference was observed for ethambutol or pyrazinamide. The opposite effect was observed for isoniazid, to which the mutants are greater than 100-fold more resistant than the wild type while I64 exhibits only 16-fold greater resistance (Table 6).

EXAMPLE 10

Identification of MshD

Bacterial Strains and Growth Conditions

*M. smegmatis* strain $mc^2155$ was obtained from W. R. Jacobs (Department of Microbiology and Immunology, Albert Einstein College of Medicine, Bronx, N.Y. USA) and cultured at 37° C. in Middlebrook 7H9 media supplemented with 0.05% Tween 80 and 1% glucose unless otherwise noted.

Construction of Mutant Library

The gram negative bacterial Tn5 transposition system was selected to generate this *M. smegmatis* mutant library due to its random target sequence specificity. An *M. smegmatis* (Tn5) EZ::TN<KAN-2> (Epicentre) transposon library was prepared according to the manufacturer's instructions (Derbyshire et al. (2000) *Epicentre Forum* 2:1-4; Goryshin et al. (2000) *Nature Biotechnol* 18:97-100). Electrocompetent *M. smegmatis* strain $mc^2155$ cells were prepared as described in Example 6. The library contained mutants from 20 separate 1-μl transformations plated on 20 150-mm dishes each containing 125 ml Trypticase Soy Broth medium (BBL) with 10 μg kanamycin/ml and 30 μg isoniazid/ml. Reactions without DNA and with DNA were plated without isoniazid as controls. Transformants resistant to both kanamycin and isoniazid were gridded and replated on 7H9 Middlebrook agar supplemented with 0.4% glucose, 0.05% Tween 80, 20 μg kanamycin/ml and 100 μg isoniazid/ml. Transformants that survived the increased levels of antibiotics were subcultured into 5 ml 7H9 Middlebrook media containing 0.05% Tween 80, 1% glucose, 20 μg kanamycin/ml at 37° C. with shaking. Cells from a portion (2 ml) of the stationary phase culture were collected by centrifugation and analyzed for thiols as described below. Transformants containing less than 1% of the wild-type mycothiol content were retained for genetic analysis.

Determination of Thiols and GlcN-Ins

Cells were extracted and labeled with mBBr for thiol analysis as described previously with the exception that HEPES was substituted for Tris. The thiol-bimane derivatives (RSMB) were analyzed using a minor modification of HPLC method 1 (Fahey and Newton (1987) *Methods Enzymol* 143: 85-96) to provide improved separation of MSmB from the major reagent hydrolysis peak. A 4.6×25 cm Beckman ULTRASPHERE® ODS IP (ion pairing) column (No. 235335) was used with buffers A (0.25% acetic acid in $H_2O$ titrated to pH 3.6 with NaOH) and buffer B (HPLC grade methanol, Fisher). The linear gradient was as follows: 0 min, 10% B; 5 min, 10% B; 15 min, 18% B; 30 min, 27% B; 32 min, 100% B; 34 min, 10% B; 45 min, reinject. The flow rate was 1.2 ml/min at ambient temperature and retention times were as follows: CySmB-GlcN-Ins, 9.4 min; CySmB, 10.8 min; U18, 18 min; mBOH (reagent hydrolysis), 19.3 min; MSmB, 21 min; AcCySmB, 26 min.

Genetic Analysis of MSH-Deficient Mutant mshD::Tn5

Figure 9:
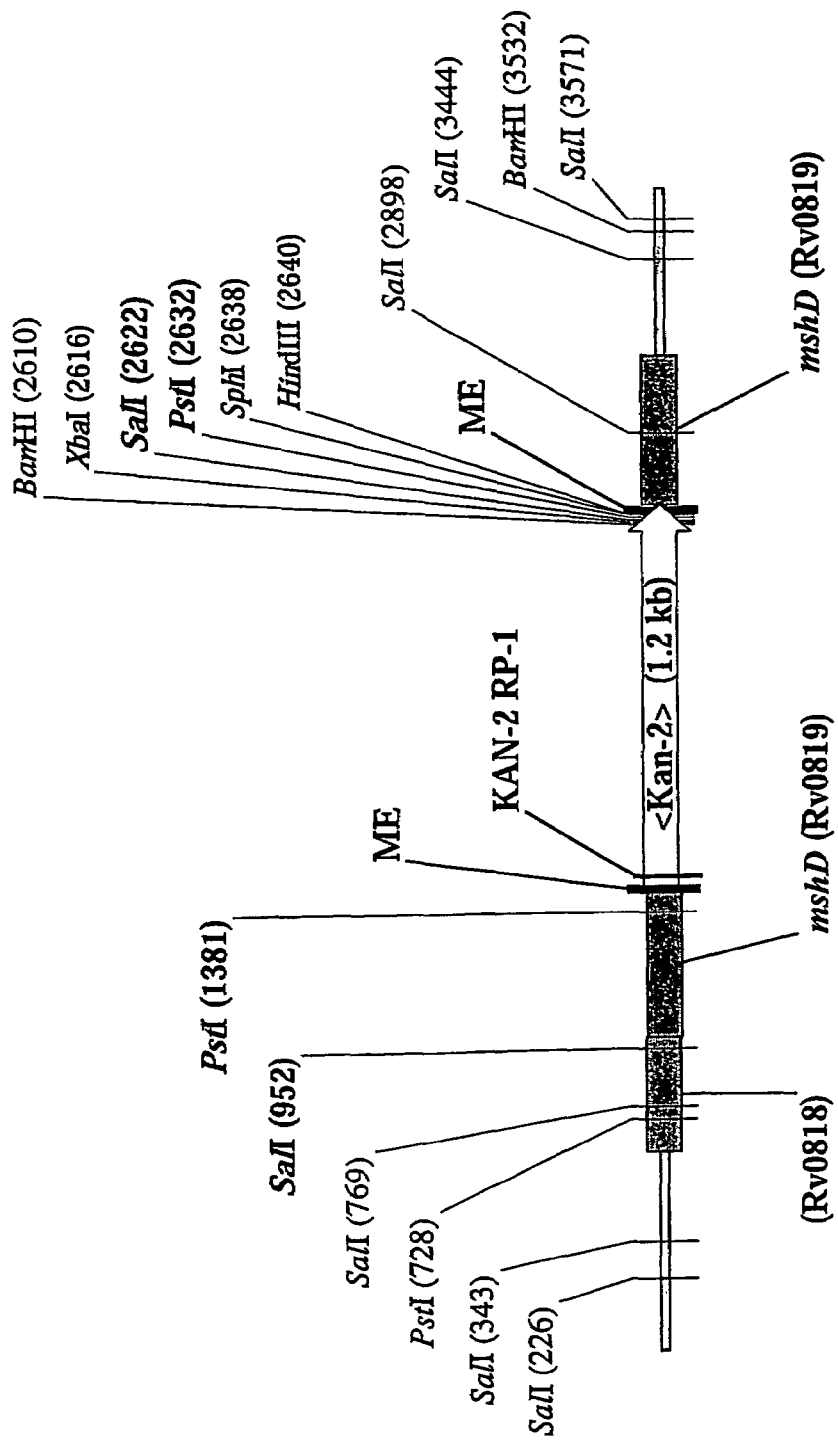
FIG. 9 shows a section of *M. smegmatis* cosmid 3269 showing the insertion site of the <KAN-2> transposon in the mshD gene (crosshatched) as defined by the mosaic end sequences (ME). Sequencing of the *M. smegmatis* genomic DNA commenced with the <KAN-2> reverse primer RP-1. The segments corresponding to *M. tuberculosis* open reading frames Rv0818 and Rv0819 are denoted as such.

Genomic DNA was purified from a 250 ml culture of mshD::Tn5 by standard methods (Larsen, "Genomic DNA preparation" In: Hatfull G F, Jacobs J, W. R. (eds) *Molecular Genetics of Mycobacteria*, ASM Press, Washington D.C., pp 313-320, 2000). Initial attempts to sequence outward from the insert with intact genomic DNA according to the manufacturer's instructions gave inadequate sequence quality. Therefore the transposon and adjacent genomic DNA (FIG. 9) was subcloned into pUC18 for sequencing. Genomic DNA was digested with SalI or PstI (Invitrogen; FIG. 9) and cloned into similarly digested pUC18 plasmid DNA (Sambrook et al. 1989, supra). *E. coli* DH5α (Invitrogen) was transformed with the resulting plasmids and the kanamycin resistant transformants were analyzed for the presence of inserts larger than the EZ::TN<KAN-2> transposon (1.2 kb), indicating the presence of *M. smegmatis* genomic DNA. The purified plasmid DNA with insert and the EZ::TN<KAN-2> reverse primer RP-1 (Epicentre) were submitted to the UCSD Cancer Center Sequencing Center for sequence determination. The sequences were analyzed using published and unpublished genome sequence data at the Sanger Centre website (on the worldwide web at sanger.ac.uk). Preliminary sequence data for *M. smegmatis* $mc^2155$ was obtained from The Institute for Genomic Research website on the worldwide web at tigr.org.

Attempts to identify the disrupted mycothiol biosynthesis gene by sequencing outward from the transposon using intact genomic DNA gave a sequence with many undetermined bases and the approach was unsuccessful at identifying the MshD gene. The EZ::TN<KAN-2> transposon with adjacent genomic DNA (FIG. 9) was subcloned into pUC18 for sequencing. The PstI clone gave 78 bp of sequence complementary to bases 1364224-1364301 of the unfinished *M. smegmatis* genome (gnl|TIGR__1772|contig:3312) at the TIGR website. The Sal I plasmid gave 504 bp of sequence complementary to bases 1363797-1364301, a longer sequence of the same gene at the same insertion point (FIG. 9).

Cloning of the *M. tuberculosis* mshD Gene and Expression in *E. coli*

The mshD gene (Rv0819) was amplified from *M. tuberculosis* H37Rv chromosomal DNA using Platinum Pfx DNA Polymerase (Invitrogen) with oligonucleotide primers

```
5'-
GGCTTGCAGGTGACGGCGCTTGACTGGCGCT-3' (SEQ ID NO: 23)
and
5'-
GGAAGCTTGTTATCCGTGCCAGCCAGCGCG-3', (SEQ ID NO: 24)
``` which generated a polymerase chain reaction (PCR) product containing a unique PstI cut site at the 5'-terminus and a Hind III site at the 3'-terminus. The PCR product was purified from a 1.2% agarose gel using a Qiagen gel extraction kit. The PCR fragment was then digested with PstI and HindIII according to the manufacturer's instructions and purified from a 1.2% agarose gel as above. The expression vector, pRSET C (Invitrogen), was similarly digested and purified. The digested mshD gene and vector were ligated with T4 DNA Ligase (Invitrogen) to generate plasmid pRS0819. The ligation mixture was used to transform competent *E. coli* DH5α cells, which were plated on LB agar (Sambrook et al. 1989, supra) containing 100 µg ampicillin/ml.

The transformants were cultured in 5 ml of LB broth containing 100 µg ampicillin/ml overnight at 37° C. The plasmids were purified with a Qiagen mini prep kit, digested with Pst I and Hind III as above, and analyzed by electrophoresis to verify the presence of the mshD gene (~950 bp) insert. The expression plasmid pRS0819 and the empty pRSET C vector were used to transform *E. coli* BL21 (DE3) pLysS (Invitrogen). Transformants were selected on LB agar containing 100 µg ampicillin/ml and 35 µg chloramphenicol/ml to maintain plasmid pLysS.

Preparation of Cys-GlcN-Ins

The bimane derivative of Cys-GlcN-Ins (CySmB-GlcN-Ins) from the acid hydrolysis of MSmB prepared as described above was used as a standard for HPLC. Cys-GlcN-Ins in the thiol form was purified from 5 liters (23 g wet weight) of late exponential phase mshD::Tn5 cells essentially as described previously for MSH (Unson et al. 1998, supra). However, DTT was added to the extract prior to thiol affinity chromatography and after the final preparative HPLC step in order to maintain the readily oxidizable Cys-GlcN-Ins in the reduced form. The final product (unretained on preparative HPLC and coeluted with Tris on HPLC) contained 1 µmol of Cys-GlcN-Ins in 1 ml of 1 mM DTT, 1 M Tris-TFA, pH 7.0, corresponding to a 23% overall recovery.

Assay of Mycothiol Synthase (MshD) in Extracts

Exponential phase cultures ($OD_{600}$~1) of *M. smegmatis* $mc^2155$ and mshD::Tn5 in 7H9 Middlebrook media containing 1% glucose and 20 µg kanamycin/ml (as necessary) were harvested by centrifugation. The *E. coli* MshD expression strain pRS0819 and the empty pRSET C vector strain were cultured in LB medium containing 100 µg ampicillin/ml and 35 µg chloramphenicol/ml to $OD_{600}$~0.6. The cells were induced with 0.75 mM isopropyl-β-D-thiogalactopyranoside for 16 h at 22° C. Cells were harvested and resuspended 1:5 (w/v) in extraction buffer (50 mM HEPES pH 7.5, 50 mM NaCl, 1 mM 2-mercaptoethanol, and 35 µM of the protease inhibitors, N-α-p-tosyl-L-phenylalanylchloromethyl ketone and N-α-p-tosyl-L-lysinechloromethyl ketone). The cells were disrupted by sonication on ice and the cell debris was removed by centrifugation at 10,000 g (4° C.) for 20 min.

Mycothiol synthase assays were carried out in a 100 µl total volume containing 10 µl *M. smegmatis* extract or 5 µl of 100-fold diluted *E. coli* extract, 50 mM HEPES pH 7.5, 2 mM DTT, 100 µM CoASAc, and 50 µM Cys-GlcN-Ins. The reaction was sampled prior to addition of extract (zero time) and after 10, 20, and 30 min incubation at 37° C. for *M. smegmatis* and after 3, 6, and 12 min for *E. coli*. Samples (20 µl) were quenched and derivatized by mixing with 20 µl of 8 mM mBBr in acetonitrile at 60° C. The derivatized sample was incubated at 60° C. for an additional 10 min, cooled on ice, acidified with 5M methanesulfonic acid to a final concentration of 10 mM, and clarified by centrifugation. The sample was diluted 4-fold in aqueous 10 mM methanesulfonic acid and analyzed by HPLC for the bimane derivatives of Cys-GlcN-Ins and MSH as described above. Controls included samples without extract and without CoASAc. Protein content of extracts was determined by the method of Bradford (Bradford 1976, supra).

Results

A M. smegmatis mutant, strain 49, is severely deficient in MSH and is resistant to 100 μg isoniazid/ml, a concentration 100-fold above the minimal inhibitory concentration for the wild-type strain mc²155 (Newton et al. 1999). Therefore tests were conducted to determine whether isoniazid could be used as a preliminary screen for isolation of MSH deficient mutants in a library generated from M. smegmatis by the Tn5 transposition process which involves a cut-and paste mechanism (Goryshin et al. 2000, supra). Transformants generated with the commercially available EZ::TN <KAN-2> transposon kit were initially screened on 10 μg kanamycin/ml and 30 μg isoniazid/ml. These transformants were then gridded and replated on 20 μg kanamycin/ml, to select for the <KAN-2> transposon, and 100 μg isoniazid/ml, to select for mycothiol deficiency, generating a library of ~2,000 highly isoniazid-resistant mutants. These individual mutants were screened for thiols by HPLC and 3 mutants in the first 200 screened had a mycothiol content of <1% of the wild-type level. One of these mutants, designated mshD::Tn5, contained substantial amounts of Cys-GlcN-Ins as would be expected from a mycothiol synthase (MshD) mutant (FIG. 1). The other two mutants were found to have levels of mycothiol precursors consistent with mutations in earlier steps of mycothiol biosynthesis.

The levels of mycothiol and its precursors were analyzed and the MSH level in mshD::Tn5 was found to be <5% of the mc²155 wild-type level as shown in Table 7 below:

TABLE 7

Cellular levels of mycothiol precursors, mycothiol, and mycothiol synthase activity in M. smegmatis wild-type (mc²155) and mycothiol mutant (mshD::Tn5)

| Strain-growth phase | GlcN-Ins | Cys-GlcN-Ins | MSH | MSH Synthase [nmole min⁻¹ (mg protein)⁻¹] |
|---|---|---|---|---|
| | (μmol/g residual dry weight) | | | |
| mc²155-exp | 0.1ᵃ | 0.008ᵃ | 10ᵃ | 5.8 ± 0.8 |
| mc²155-stat | 0.01ᵃ | ND | 10ᵃ | ND |
| mshD::Tn5-exp | 0.35 ± 0.05 | 2.3 ± 0.10 | 0.12 ± 0.008 | 0 ± 0.2 |
| mshD::Tn5-stat | 0.27 ± 0.01 | 0.84 ± 0.025 | 0.065 ± 0.010 | ND |

ᵃData from (Anderberg et al. 1998).
ND, not determined;
exp, exponential growth phase cells;
stat, stationary growth phase cells.

As shown in Table 7, whereas the level of Cys-GlcN-Ins in mc²155 is very low and difficult to measure, Cys-GlcN-Ins proved to be a major thiol produced in mshD::Tn5, found at 290-fold higher level than in the wild-type strain during exponential phase growth. The level of GlcN-Ins was increased 3- to 30-fold over that found in the wild-type strain. Thus, the two immediate precursors to mycothiol in the biosynthetic pathway accumulate in this mutant. An unidentified thiol was observed at 18 min in the HPLC analysis and was estimated to occur at 1-5 μmol per g residual dry weight in different cultures.

Assays of the mycothiol synthase activity in dialyzed cell extracts showed a complete loss of acetyl-CoA/Cys-GlcN-Ins acetyltransferase (MshD) activity in mutant mshD::Tn5 relative to the wild-type strain (Table 7), establishing that mshD::Tn5 is defective in MshD activity.

The M. smegmatis genome has been completely sequenced but the annotation is not yet available, so the annotated M. tuberculosis H37Rv genome (Cole et al. 1998, supra) on Tuberculist (with url address: genolist.pasteur.fr/TuberculList) was used to describe the transposon insertion and sequence analysis. A tblastx search of the initial portion of the experimental sequence produced an optimal match with ORF Rv0819 while the latter portion matched Rv0818. This indicated that the transposon had inserted into the M. smegmatis gene corresponding to Rv0819, annotated as a hypothetical protein of unknown function. A tblastn search of the M. smegmatis unfinished genome at the TIGR website using the M. tuberculosis protein sequence for Rv0819 produced a fit with 60% identity for residues 1-253 in the +1 reading frame and a 50% identity for a fit of residues 245-309 in the +2 reading frame. Deleting cytosine-733 in the M. smegmatis sequence produced a frame shift allowing an optimal alignment of the M. tuberculosis and M. smegmatis sequences with 62% overall identity as shown in FIG. 8. Using the Sanger Centre databases matches were also found for the completed genome sequence of M. leprae (Cole et al. 2001) with 75% identity in a 315 residue overlap, for the finished genome sequence of Streptomyces coelicolor A3(2) with 46% identity in a 256 residue overlap, and for the in-progress genome sequence Corynebacterium diphtheriae with 34% identity in a 304 residue overlap. All of these organisms belong to families shown to produce MSH (Newton et al. 1996).

To verify the assignment of M. tuberculosis gene Rv0819 as an ortholog of MshD from M. smegmatis, it was cloned into pRSET C and expressed in E. coli. When the protein was expressed at 22° C. the cloned MshD protein band was the dominant protein in the soluble crude cell extract with a subunit molecular mass of ~38 kDa (results not shown). The MshD was active in the crude cell extract as the His6 tagged protein with a specific activity of 500±50 nmole min⁻¹ (mg protein)⁻¹. Parallel measurements on crude extracts of the E. coli empty vector control gave no measurable rate, 1±1 nmole min⁻¹ (mg protein)⁻¹, under identical conditions. Thus, the gene product of Rv0819 from M. tuberculosis is confirmed as having MshD activity.

EXAMPLE 11

Identification of MshA

Strains and Plasmids.

Escherichia coli was grown in Luria-Bertani (LB) agar or broth at 37° C. Ampicillin (Sigma; 100 μg/ml), kanamycin (Sigma; 50 μg/ml) and hygroniycin (Calbiochem; 150 μg/ml) were used when required. M. smegmatis strains were grown at 37° C. in Middlebrook 7H9 broth (Difco) supplemented with 0.05% TWEEN-80® detergent, 1% glucose and 10% OADC (BBL) or in 7H10 agar (Difco) supplemented with 0.5% glycerol, 1% glucose and 10% OADC. For mycobacterial growth, hygromycin (75 μg/ml) and kanamycin (25 μg/ml) were used when required.

Isolation of MshA::Tn5

A Tn5 transposon library was constructed using the EZ::TN <KAN-2> kit from Epicentre and yielded three MSH-deficient mutants, which were strongly resistant to isoniazid. These were subcultured with shaking in 7H9 Middlebrook medium containing 0.05% TWEEN-80® detergent, 1% glucose and 20 μg/ml kanamycin at 37° C., and samples were collected in late exponential or early stationary phase growth for determination of mycothiol components as described below. One mutant was found to have no measurable levels of MSH, GlcNAc-Ins, or GlcN-Ins and was designated as strain MshA::Tn5.

Genetic Analysis of MshA::Tn5

A 250 ml culture of MshA::Tn5 was prepared for isolation of genomic DNA by standard methods (M. H. Larsen, "Some common methods in mycobacterial genetics. In G. F. Hatful and J. Jabobs, (Ed.), *Molecular Genetics of Mycobacteria*, ASM Press, Washington D.C., pp 313-320.8) but attempts to sequence outward from the insert with this DNA gave poor sequence quality. The transposon with adjacent DNA (FIG. 13) was therefore subcloned into pUC18 for sequencing. Briefly, genomic DNA was digested with either SalI or PstI (Invitrogen) and cloned into similarly digested pUC18 plasmid DNA. The resulting plasmids were used to transform competent *E. coli* DH5α (Invitrogen), and the kanamycin resistant transformants were analyzed for the presence of inserts larger than the EZ::TN plasmid DNA <KAN-2> transposon (1.2 kb), indicating the presence of *M. smegmatis* genomic DNA. The plasmids containing transposons were isolated using a QIAprep® Spin Miniprep Kit (Qiagen) and was sequenced by the UCSD Cancer Center Sequencing Center using the EZ::TN <KAN-2> reverse primer RP-1 supplied by Epicentre.

Cloning of ORF Rv0486 from *M. tuberculosis* and Complementation of mshA Mutants.

*M. tuberculosis* H37Rv genomic DNA was prepared as described previously. The open reading frame (ORF) Rv0486 was amplified by PCR using this DNA and primers

```
486 PAL 3
(5' CATATGCACGGTCGGCAAGGAGG-3')      (SEQ ID NO: 25)
and

486 PAL 5
(5' AGGATCCATGGCAGGTGTGCGGCAC 3').   (SEQ ID NO: 26)
```

These primers were designed to contain NdeI and BamHI restriction sites, respectively. PCR was performed with Taq polymerase (Gibco BRL) using 1 mM $MgCl_2$ and 5% dimethyl sulfoxide (DMSO). Thirty cycles of PCR included denaturation at 94° C. for 40 sec, annealing at 60° C. for 1 min, and amplification at 72° C. The PCR products were separated on a 0.8% Agarose gel. The appropriate PCR product was ligated into the vector pCR2.1 of the TA cloning kit (Invitrogen), and transformed into competent *E. coli* cells by standard heat shock transformation procedure. Plasmid DNA was isolated and restriction digestion with NdeI and BamHI (Fermentas) was used for verification and subcloning. A fragment corresponding in size to ORF Rv0486 was isolated from agarose gels, purified using a QIAquick® Gel Extraction Kit (Qiagen), and ligated to pALACE to obtain the plasmid pALO486. This pAL0486 plasmid was electroporated into the MSH deficient mutants A1 and 49 as previously described and selection was performed on hygromycin plates (Newton et al. (1999), supra).

Mapping the Chemical Mutation in Mutant 49

The *M. smegmatis* sequence obtained from The Institute for Genomic Research was used to design primers upstream of the start codon:

```
(49seq 5'
(5'GCAACGAGAAGGCCGTCGAACT 3')      (SEQ ID NO: 27)
``` and downstream of the 3' region

```
(49seq 3'(5'GTCCTCGATGATCTTCCTGACA 3') (SEQ ID NO: 28)
``` of the *M. smegmatis* mshA gene. The primers were used to amplify *M. smegmatis* $mc^2155$ and DNA from two different colonies of mutant 49 and the amplified band was cloned into pCR2.1 (Invitrogen). After ensuring by restriction digestion that the *M. smegmatis* mshA gene had been cloned, the DNA was sequenced using primers 49seq 5' and 49seq 3' as well as the universal primers T7 and M13R. To sequence the internal region of the homolog and confirm the missense mutation, the same procedure was followed with primers

```
49MED 5'
(5' GCGTGGCGGTGTTGTCGGTA 3')      (SEQ ID NO: 29)
and

49MED 3'
(5' GACCAGTTGTTCGCGGCTCT 3').     (SEQ ID NO: 30)
```

Comparison of the sequences obtained in this manner revealed a single base pair change in the mutant converting a GGC codon to GAC. This results in a change in the amino acid at position 32 of the *M. smegmatis* sequence from glycine in $mc^2155$ to aspartic acid in mutant 49 (FIG. 11).

Determination of MSH, GlcNAc-Ins and GlcN-Ins.

Replicate cell pellets (~100 mg wet weight) were extracted and labeled with mBBr for thiol analysis as described previously. Parallel samples were extracted at 60° C. in 50% acetonitrile containing 20 mM HEPES pH 8.0 for GlcNAc-Ins and GlcN-Ins analysis. The 50% acetonitrile extract was reduced under vacuum to remove acetonitrile from the cell free extracts. A zero time sample (20 μl) was removed, recombinant Rv1170 (MshB; 100 μg/ml) added, and the samples incubated at 37° C. Aliquots (20 μl) were removed after 30, 60, and 90 min; all samples were quenched by addition of an equal volume of acetonitrile containing 10 mM NEM and 2 mM 1,10-phenanthroline and heating at 60° C. for 10 min. The samples were derivatized with AccQ-Fluor® reagent (Waters) and analyzed by HPLC for the AccQ derivative of GlcN-Ins as previously described. The zero time samples were used to determine the level of GlcN-Ins in the cells. The addition of the MshB releases GlcN-Ins from GlcNAc-Ins and provides a determination of GlcN-Ins plus GlcNAc-Ins. Since calculation of the value for GleNAc-Ins requires subtraction of the GlcN-Ins level from this value, the GlcN-Ins level is only analyzed reliably when its value is a significant fraction (e.g. >10-20%) of the GlcN-Ins level.

Antibiotic Sensitivity Testing

Mutants and complements were grown in Middlebrook 7H9 media supplemented with OADC and the appropriate antibiotics. The cultures were diluted to O.D.600 nm=0.4 and incubated at 37° C. for 2-4 hours before being swabbed on Middlebrook solid media supplemented with OADC and the appropriate antibiotics. In the case of the complements, mshA::Tn5 pAL0486 and 49::pAL0486, 1% acetamide was also added to the solid media. After swabbing, the cultures were allowed to dry for 15 minutes and the Estrip (AB Biodisk) was gently laid onto the plates. The plates were incubated for 2-3 days before the MIC was determined.

Sequence Analysis.

Preliminary sequence data for *M. smegmatis* was obtained from The Institute for Genomic Research website (at worldwide web address tigr.org). Sequences of MshA were obtained from GenBank with accession numbers as follows: *M. tuberculosis* Rv0486, NP-215000; *M. leprae* ML2143, NP-302584; *Streptomyces coelicolor* A3 2SCD46.18, NP_628379; *Corynebacterium glutamicum* NCg10389, NP-599648. Sequence alignment using the Clustal W algorithm (J. D. Thompson et al. (1994) *Nucleic Acids Res* 22:4673-80) was performed with Vector NTI Suite for Macintosh version 5.3.0. Results of the sequence alignment are shown in FIG. 11.

Results

An *M. smegmatis* Transposon Mutant Deficient in GlcNAc-Ins and MSH Production (MshA::Tn5).

A Tn5 transposon library enriched for MSH-deficient mutants was produced using the EZ::TN<KAN-2>) system from Epicentre and selecting for resistance to both kanamycin and isoniazid, the latter resistance having been established as a phenotype which is characteristic of MSH-deficient strains. Three mutants from the Tn5 transposon library were found deficient in MSH. One was tentatively designated mshA::Tn5 because it was found to produce no measurable amount of GlcNAc-Ins or GlcN-Ins (Table 8) which suggested that it was defective in MshA.

TABLE 8

Levels of mycothiol and its precursors in mshA mutants and their complements

| *M. smegmatis* strain | Cellular level (μmol per g residual dry weight)[a] | | |
|---|---|---|---|
| | GlcNAc-Ins[b] | GlcN-Ins[b] | MSH[b] |
| mc²155 | ≦0.2 | 1.0 ± 0.2 | 10 ± 3 |
| mshA::Tn5 | ≦0.01 | ≦0.01 | ≦0.01 |
| mshA::Tn5 pAL0486 | | | |
| clone 1[c] | 0.10 ± 0.02 | 0.49 ± 0.05 | 9.4 ± 0.4 |
| clone 2[c] | 0.053 ± 0.012 | 0.64 ± 0.03 | 9.6 ± 0.2 |
| 49 | ≦0.001 | ≦0.001 | ≦0.01 |
| 49::pAL0486 | | | |
| clone 1[c] | 0.25 ± 0.09 | 1.3 ± 0.2 | 11.5 ± 0.3 |
| clone 2[c] | 0.15 ± 0.04 | 0.84 ± 0.08 | 11.1 ± 0.3 |

[a]Mean and range of duplicate samples of exponential cells cultured in Middlebrook 7H9 medium containing 1.0% glucose and 0.05% Tween 80 with 75 μg/ml hygromycin and 20 μg/ml kanamycin as appropriate.
[b]Determined by published methods for MSH (Koledin, et al., Arch. Microbiol. 178: 331-337 (2002)), GlcNAc-Ins (Buchmeier, et al., Mol. Microbiol., 47: 1723-1732 (2003).), and GlcN-Ins (Id.).
[c]Cells were cultured as above to $OD_{600}$ = 0.5, transferred to Middlebrook 7H9 medium without glucose, and induced for 20 h at 23° C. with 0.2% acetamide.

The mshA Gene Encodes a Glycosyltransferase.

Figure 13:
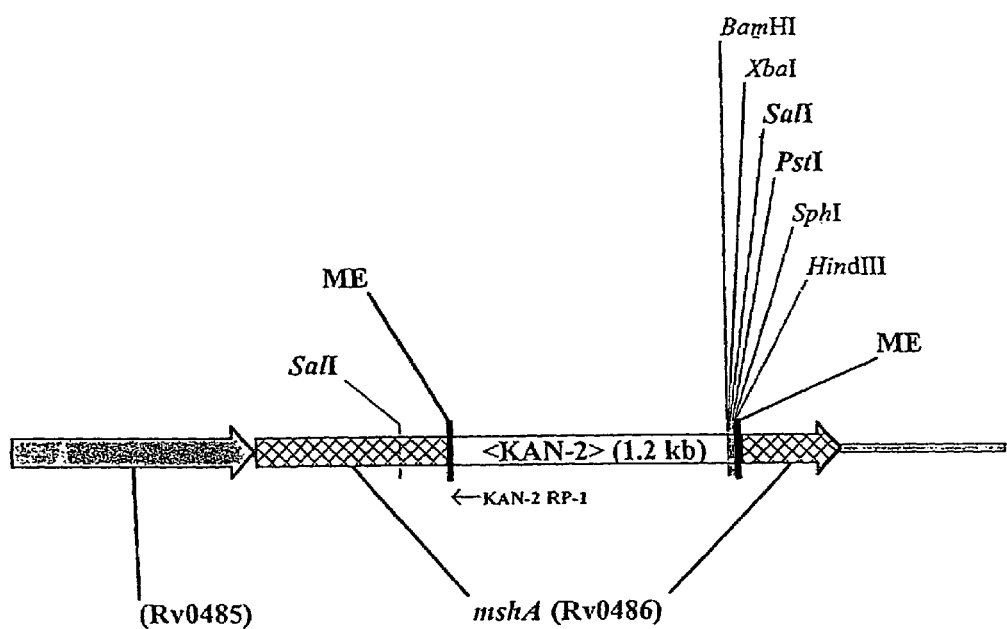
FIG. 13 shows the genomic locus of *M. smegmatis* transposon mutant mshA:Tn5, displaying the site occupied by the EZ::TN<KAN-2> transposon in the mshA gene (crosshatched) as defined by the mosaic end sequences (ME) and the reverse sequencing primer KAN-2 RP-1. The sites corresponding to the *M. tuberculosis* H37Rv orthologs Rv0485 and Rv0486 are given in parenthesis.

In order to obtain high quality sequence for the genomic DNA of MshA::Tn5 at the site of insertion, it was necessary to subclone the transposon and adjacent genomic DNA into pUC18 using either SalI or PstI (FIG. 13). The SalI clone produced 205 bp of sequence and the PstI clone produced 822 bp of sequence, both at the same insertion site, the PstI clone corresponding to the complement of bases 507551-508372 of contig 3311 of the unfinished *M. smegmatis* genome at The Institute for Genomic Research (on the world wide web at tigr.org). Since the *M. smegmatis* sequence has not yet been annotated, the experimental sequence was used to search the *M. tuberculosis* H37Rv genome database at GenBank using tblastx. This identified a 236 amino acid residue sequence from ORF Rv0486 having 84% identity with the translated experimental sequence. Having established the reading frame for the *M. smegmatis* sequence, a downstream stop codon defined the termination site for the *M. smegmatis* gene. The start position for the gene was taken to be defined by a GTG codon found upstream from the end of the region with high identity to the *M. tuberculosis* sequence and downstream from an in-frame stop codon. This identified the sequence for MshA as shown in FIG. 11. The *M. smegmatis* and *M. tuberculosis* MshA sequences are 75% identical in a 446 residue overlap.

The *M. tuberculosis* MshA Gene (Rv0486) Complements mshA::Tn5 and Chemical Mutant 49

To verify that Rv0486 encodes the enzyme activity missing in the transposon and chemical mutants, the gene was cloned into the pALACE vector to produce pAL0486, which was used to transform mshA::Tn5 and mutant 49. *M. tuberculosis* H37Rv genomic DNA was prepared as described previously. The open reading frame (ORF) Rv0486 was amplified by PCR using this DNA and primers

```
486 PAL 3
(5'CATATGCACGGTCGGCAAGGAGG3')    (SEQ ID NO: 25)
and

486 PAL 5
(5'AGGATCCATGGCAGGTGTGCGGCAC3'). (SEQ ID NO: 26)
```

These primers were designed to contain NdeI and BamHI restriction sites, respectively. PCR was performed as described earlier and the appropriate PCR product was ligated into pALACE to obtain the plasmid pAL0486. This pAL0486 plasmid was electroporated into the MSH deficient mutants as previously described and selection was performed on plates containing hygromycin for mutant 49 and hygromycin plus kanamycin for mshA::Tn5 (Newton, et al., 1999, supra)

In each case, two clones were selected from the hygromycin plates for growth in liquid culture to produce cells for analysis of MSH and its precursors. The results (Table 8) demonstrated that full restoration of MSH production to wild type levels occurs with acetamide induced cultures and levels of GlcNAc-Ins and GlcN-Ins increase to normal or near-normal levels in both mutants. This confirms that the loss of MSH biosynthesis capacity in mutant mshA::Tn5 results solely from inactivation of the mshA gene and demonstrates that mutant 49 is defective in the mshA gene.

To ascertain the nature of the defect in the mshA gene of mutant 49, the mshA genes from the parent strain, *M. smegmatis* mc²155, and mutant 49 were cloned and sequenced. The *M. smegmatis* sequence obtained from The Institute for Genomic Research was used to design primers upstream of the start codon (49seq 5'; 5'GCAACGAGAAGGCCGTC-GAACT3') (SEQ ID NO: 27) and downstream of the 3' region (49seq 3'; 5'GTCCTCGATGATCTTCCTGACA3') (SEQ ID NO: 28) of the *M. smegmatis* mshA gene. The primers were used to amplify the DNA from *M. smegmatis* mc²155 and from two different colonies of mutant 49 and each amplified band was cloned into pCR2.1 (Invitrogen). After ensuring by restriction digestion that the *M. smegmatis* mshA had been cloned, the DNA was sequenced using primers 49seq 5' and 49seq 3' as well as the universal primers T7 and M13R. To sequence the internal region of the homolog and confirm the missense mutation, the same procedure was followed with primers

```
49MED 5'
(5'GCGTGGCGGTGTTGTCGGTA3')    (SEQ ID NO: 29)
and

49MED 3'
(5'GACCAGTTGTTCGCGGCTCT3').   (SEQ ID NO: 30)
```

Comparison of the sequences revealed a single base pair change in the mutant converting a GGC codon to GAC. This results in a change in the amino acid at position 32 of the *M. smegmatis* sequence from glycine in mc²155 to aspartic acid in mutant 49 (FIG. 11).

Orthologs of mshA are Present in Diverse MSH-Producing Actinomycetes.

Complete genomes are available for several members of the actinomycetes belonging to genera previously shown to produce mycothiol (Newton, et al., (1996) *J. Bacteriol.* 178: 1990-1995.). These include *M. leprae, Streptomyces coelicolor* A3(2), and *Corynebacterium glutamicum*, each containing a gene that translates with a high degree of identity to the *M. tuberculosis* and *M. smegmatis* MshA proteins (FIG. 11). The mshA mutants have altered antibiotic sensitivity compared to the parent strain.

The ortholog from *M. leprae* is 82% identical to the *M. tuberculosis* sequence whereas the evolutionarily more distant *S. coelicolor* and *C. glutamicum* sequences are respectively 49 and 47% identical. The sensitivity of the *M. smegmatis* parent strain mc²155, transposon mutant mshA::Tn5 and chemical mutant 49 to isoniazid was tested using Estrips (Oxoid) and assessing inhibition of growth after 2-3 days at 37° C. The MIC values determined were respectively 1, >250, and >250 µg/ml for isoniazid. The MIC values for mc²155 and mutant 49 are similar to those found earlier for isoniazid, 2 and >50 µg/ml, by plating on antibiotic containing media (Newton, et al., 1999, supra.). When the isoniazid sensitivity of the complemented mshA::Tn5 and strain 49 mutants was tested on plates containing 1% acetamide but lacking glucose, the MIC values were 2.7 and 28 µg/ml, respectively, demonstrating substantial reversion to the parental phenotype. The mechanistic basis for the isoniazid resistance has not been established but there is evidence indicating that the isoniazid sensitivity is specifically linked to MSH rather than a generally high level of cellular thiol (Koledin, 2002, supra).

EXAMPLE 12

Characterization of *M. tuberculosis* MshC

Reagents

Middlebrook 7H9 was purchased from Difco Laboratories, and glucose and Tween 80 were from Fisher. MSH was isolated from *M. smegmatis* as described (Unson, et al, (1998) *J. Immunol. Meth.* 214, 29-39.) and the monobromobimane (mBBr, Molecular Probes) derivative (MSmB) was prepared and purified by the method of Newton, et al. (1995) *Methods Enzymol.* 251, 148-166. GlcN-Ins was prepared by the quantitative hydrolysis of MSmB by purified *M. smegmatis* mycothiol S-conjugate amidase as previously described (Newton, et al. (2000) *Biochemistry* 35, 10739-10746.). CySmB-GlcN-Ins was purified by preparative HPLC, after acid hydrolysis of MSmB, as described (Anderberg, et al. (1998) *J. Biol. Chem.* 273, 30391-30397.).

Analysis of MSH and the Precursors GlcN-Ins, GlcNAc-Ins

Cells were extracted and derivatized with mBBr for thiol analysis as previously described (Koledin, et al. (2002) *Arch. Microbiol.* 178, 331-337.). The mycothiol precursors, GlcN-Ins and GlcNAc-Ins, were measured by the method of Buchmeier, et al. (Buchmeier, et al. (2003) *Mol. Microbiol.* 47, 1723-1732.).

MshC Ligase Assay

The standard protocol for determination of MshC activity during enzyme purification was that described by Sareen, et al., (2002) *Biochemistry* 41, 6885-6890. For kinetic studies with the natural substrates (ATP, L-Cys and GlcN-Ins) the concentration of one substrate was varied, keeping the other two constant in the presence of ~100 ng of purified *M. tuberculosis* MshC. Protease inhibitors were omitted in the kinetic studies. Alternative substrates to Cys were analyzed at 80, 200, 800 and 1600 µM with 50 µM GlcN-Ins and 1 mM each of ATP, MgCl₂ and DTT in 50 mM HEPES pH 7.5 containing ~100 ng of purified MshC. The reaction mixtures were incubated at 37° C. and sampled at 4 and 40 min. For the substrates containing the thiol group, the assay mixture was derivatized with mBBr by the standard derivatization procedure and assayed for the corresponding thiol product (i.e. MSH from AcCys). For the non-thiol substrates (e.g. L-alanine) the MshC ligase activity was determined by assay of AMP production as described below.

Cys-tRNA Synthetase Assay

The cys-tRNA synthase activity of MshC was examined using a modification of the methods of Schrier and Schimmel (Schreier, et al. (1972) *Biochemistry* 11, 1582-9.). Purified *E. coli* cys-tRNA synthetase was used as a positive control for this reaction and was a generous gift from Kirk Beebe and Paul Schimmel of The Scripps Research Institute, La Jolla, Calif. Previous studies indicate that mycobacterial tRNA synthetases will charge *E. coli* tRNAs (Kim, et al. (1998) *FEBS Lett* 427, 259-62.). Measurement of the formation of tRNA$^{cys}$ was determined by the separation of free $^{14}$C-cysteine from $^{14}$C-tRNA$^{cys}$ by the filtration of TCA precipitates (Schrier and Schimmel, 1972, supra). Acid precipitated counts are assumed to be $^{14}$C-tRNA$^{cys}$ and control reactions without tRNAs were used to estimate background filter counts.

Whatman GF/C 25 mm glass fiber filters were prewashed in 7% TCA and dried prior to use. *E. coli* cys-tRNA synthetase (15 µg) or purified *M. tuberculosis* MshC (34 µg) were assayed in 2 mM ATP, 4 mM MgCl₂, 20 mM DTT, 20 mM KCl, 0.1 mg/ml bovine serum albumin (Sigma), 10 mg/ml *E. coli* tRNAs (Boehringer Mannheim), 60 µM $^{14}$C-cysteine (18 µCi/mole, Perkin Elmer), and 50 mM HEPES pH 7.5, final concentrations in an assay volume of 100 µl. Reactions were incubated at 23° C. and 18 µl aliquots were removed from the reaction at 1, 3, 6, 9, and 15 min and mixed with 1 ml of aqueous 7% TCA. These samples were incubated for 10 min at 23° C. and vacuum filtered. The sample filters were washed with 1 ml 7% aqueous TCA followed by 5 ml 95% ethanol and dried in a vacuum oven at 50° C. Dried filters were counted in 9 ml Econo-Safe scintillation cocktail (Research Products International) in a Beckman model LS 1701 scintillation counter.

AMP Assay

The formation of AMP was assayed by HPLC with some changes in the method described by Beuerle, et al (2002). The ligase reaction mixture (100 µL) was terminated by the addition of NEM to 2 mM followed by 2 µL of 5 N methanesulphonic acid; it was immediately frozen in dry ice. Analysis for AMP and ATP analysis conducted by HPLC on a Beckman Ultrasphere IP (250×4.6 mm) analytical column fitted with Brownley OD-GU 5 µC-18 cartridge using a flow rate of 1 mL/min and the following linear gradient: 0 min, 0.1% B (77 mM KH₂PO₄, 2.2 mM tetrabutylammonium hydroxide, 38.5% methanol, pH 5.5); 40 min, 100% B; 42 min, 100% A (10 mM KH₂PO₄, 10 mM tetrabutylammonium hydroxide, 0.25% methanol, pH 7.0); 50 min, 100% A (reinjection). The nucleotides were detected at 260 nm on a Waters 486 UV detector.

Inhibition Studies

To test for inhibition of MshC ligase activity, ~100-150 ng of the purified enzyme was incubated with different concentrations of inhibitor in 50 mM HEPES pH 7.5, for 30 min. at room temperature followed by the sequential addition of 1 mM each of DTT, ATP and MgCl₂, 70 µM L-Cys, and 50 µM GlcN-Ins in a final volume of 30 µL. Aliquots (12.5 µL) were withdrawn at 2 min. and 4 min for derivatization with mBBr and HPLC analysis as described earlier (Sareen, et al., 2002, supra.). For MSH and Cys-GlcN-Ins inhibition analysis, the second substrate GlcN-Ins was used at a concentration near the $K_m$ value (300 μM) found in this study. The protocol was modified for the product (Cys-GlcN-Ins) inhibition studies to allow measurement of initial rate in the presence of ~5 μM added Cys-GlcN-Ins. The enzyme level was reduced 10-20-fold to produce a rate capable of producing a measurable increase in Cys-GlcN-Ins.

Metal Chelation by Phenanthrolines

Stock solutions of 1,10-phenanthroline (Kodak) and 1,7-phenanthroline (Aldrich) were prepared in dimethylsulphoxide. Purified amidase (90 ng) in 42 μL of assay buffer was incubated with 0.1-5 mM (n=4), of phenanthrolines at room temp. for 10 min. The ligase reaction was initiated by the sequential addition of reaction components i.e. 1 mM each of ATP, $MgCl_2$ and DTT with 1 mM L-Cys and 600 μM GlcN-Ins. After 10 min. of incubation at 37° C., the reaction was stopped and derivatized by the addition of 8 mM mBBr in acetonitrile, and acidified by 10 mM methanesulfonic acid followed by HPLC analysis as described earlier (Id.).

Zn Supplementation

Purified MshC (131 ng) was incubated with 2, 10, 50 or 100 μM zinc chloride in 25 μL of the assay buffer at room temp or at 37° C. The ligase reaction was initiated by the sequential addition of 1 mM each of ATP, $MgCl_2$ and DTT, 100 μM L-Cys and 50 μM GlcN-Ins. At 2 and 4 min 12.5 μL aliquots were withdrawn and analyzed for thiol content as described above.

Cloning of mshC (cysS2) in pACE.

mshC/Rv2130c was earlier cloned in pRSETA into BamHI/HindIII sites under T7 promoter in *E. coli* BL21 DE3 pLysS (Sareen et al., 2002, supra). While there was activity in the soluble fraction, the bulk of the protein was found to accumulate in the form of insoluble inclusion bodies. Attempts to solubilize and reactivate the protein proved unsuccessful. Cloning of the native MshC protein and expression in *M. smegmatis* as a more suitable host was therefore examined.

Figure 14:
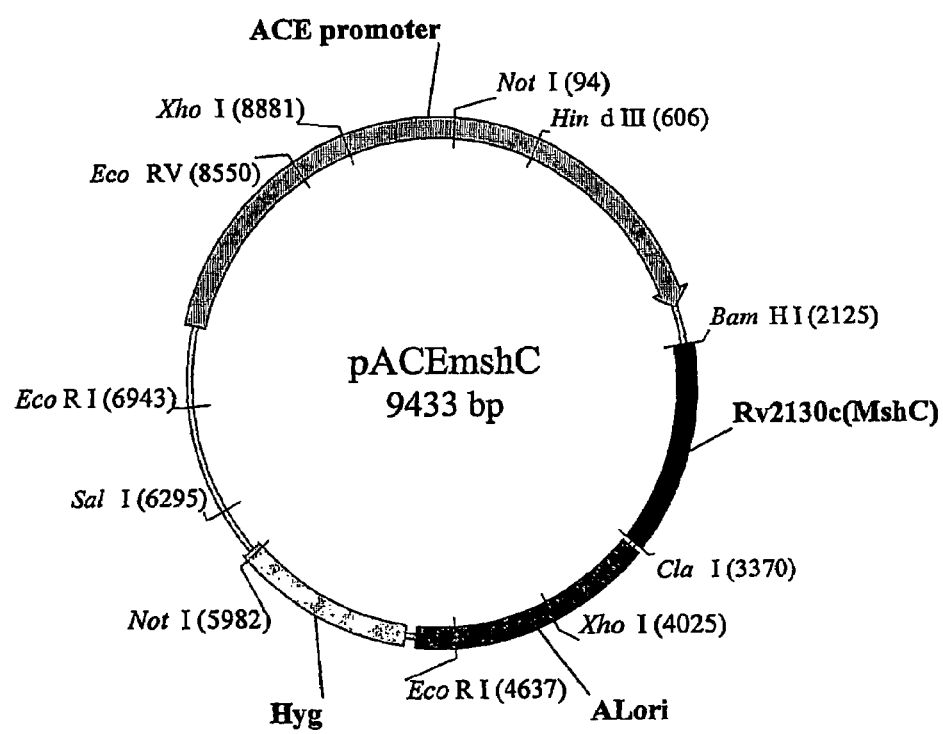
FIG. 14 is a restriction map of the pACE expression vector containing cloned mshC.

The expression was then tried in *M. smegmatis* under the acetamidase promoter of pACE (DeSmet et al., (1999) *Microbiol.* 145, 3177-3184) and pALACE (Koledin et al., 2002, supra) vectors, at the restriction sites, BamHI and ClaI. The mshC gene in pRSETA was restriction digested with BamH I and Hind III, subcloned in the vector pSODIT-2 at the two respective sites. The gene was then digested from this vector with BamHI and ClaI and was further subcloned at the respective sites in pACE. The *M. tuberculosis* mshC (Rv2130c) was cloned into pACE, a shuttle plasmid for *E. coli* and mycobacteria, having a cloning site downstream of an inducible *M. smegmatis* acetamidase promoter (De Smet, 1999, supra.) to produce pACE::mshC FIG. 14). The pACE::MshC was used to electrotransform the *M. smegmatis* I64 mutant, which is deficient in MshC activity (Rawat, et al. (2002) *Antimicrob. Agents Chemother.* 46, 3348-3355.). *M. smegmatis* mc2155 contains native MshC protein, which is translated in more than one form and would contaminate the recombinant *M. tuberculosis* MshC protein. Thus, a mycothiol mutant, I64, deficient in MshC was used as a host for expression of *M. tuberculosis* mshC. Strain I64 is deficient in MshC ligase activity due to a Leu205Pro amino acid substitution resulting from a single point chemical mutation (Rawat, et al., 2002, supra) and produces much reduced levels of mycothiol (Table 9).

The electrocompetent cells of mutant I64 were made by repeated washing of the cells cultured to exponential phase ($A_{600}$=0.5), with sterile 10% glycerol. After electroporation, the cells were supplemented with one mL of 7H9+1% Glucose and shaken at 37° C. for 4 hours before plating onto 7H9+1% glucose plates, supplemented with 75 μg/mL hygromycin.

Growth of Recombinant MshC Culture and pACEMshC Expression

*M. smegmatis* MshC mutant I64 complemented with *M. tuberculosis* mshC (Rv2130c), hereafter denoted I64::pACEmshC, was grown in 7H9 medium supplemented with 0.05% Tween 80, 10% OADC (BBL) and hygromycin (75 μg/ml) at 37° C. and 250 rpm. The culture was propagated on a large scale in the same media but with 1% glucose instead of 10% OADC. The induction was initiated at $A_{600}$=0.3 with acetamide by centrifuging the cells at 8000 g for 15 min and resuspending them in a new media without glucose and instead, 0.4% acetamide as the carbon source, while maintaining the antibiotic selection pressure. After 28 h of cultivation at 37° C. and 250 rpm, the bacterial cells were collected by centrifugation at 8000 g for 15 min. The cell pellets, about 2.3 g/liter, were stored at −70° C. until further use.

Overexpression of the MshC ligase in pACEmshC transformed *M. smegmatis* strain I64 with acetamide induction yielded protein in the soluble fraction of the cell-free extract. Following induction of pACEmshC by 0.4% acetamide in the mutant strain I64, the MSH content was measured and found to be complemented to a level 150% that of the wild type strain $mc^2155$ (Table 9). The MSH biosynthesis intermediates, GlcN-Ins and GlcNAc-Ins, were found to accumulate in mutant I64 to a level ~20-fold higher than that of the wild-type strain. Upon MshC induction in the complemented I64 strain the levels of both MSH precursors dropped to values typical of the wild-type strain and the MSH content increased 150-fold to a value above the wild-type level (Table 9).

TABLE 9

Mycothiol and precursor levels in *M. smegmatis* parent and mutant strains

| M. smegmatis strain | cellular content (μmol/(g residual dry weight)) | | |
|---|---|---|---|
| | GlcNAc-Ins | GlcN-Ins | MSH |
| mc²155 (parent) | ≦0.2 | 1.0 ± 0.2 | 10 |
| mutant I64 | 4 ± 2 | 19 ± 1 | 0.1 |
| mutant I64::pACEmshC | <0.05 | 0.4 ± 0.1 | 15 ± 1 |

Purification of Recombinant Ligase

All operations were carried out at 4° C. in the presence of 3 mM 2-mercaptoethanol and 5 mM $MgCl_2$ unless stated otherwise. Twenty grams of I64::pACEmshC cells (wet wt.) from 9 liter broth was suspended in 80 ml of 50 mM HEPES buffer (25% cell suspension), pH 7.5 in the presence of 35 μM of the protease inhibitors TPCK and TLCK. The cells were disrupted by ultrasonication (Branson Sonifier 200) in an ice bath. The cell debris was removed by centrifugation at 100,000 g for 1 h at 4° C. The supernatant obtained was used as the source of the enzyme. The cell free extract thus obtained was subjected to 20% ammonium sulfate precipitation in ice, for 2 h followed by centrifugation at 28,000 g for 30 min. The supernatant was further subjected to 20%-45% ammonium sulfate precipitation in ice for an overnight and the precipitated proteins were pelleted by centrifugation at 28,000 g for 30 min. The protein pellet (4.8 g) was resuspended in 48 ml of the 50 mM HEPES, pH 7.5 containing 35 μM of TPCK and TLCK and was desalted by passing it through Sephadex G-25 column.

Figure 15:
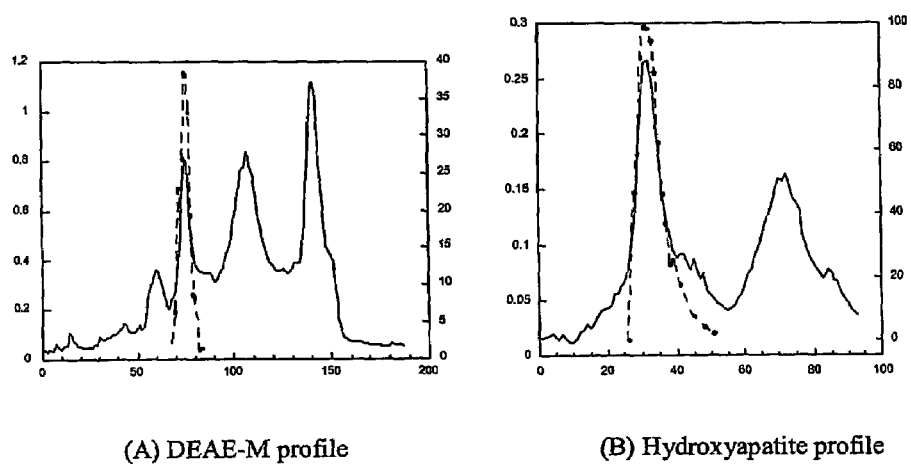
FIG. 15 shows chromatographic profiles for purification of MshC: (A) DEAE ion exchange; and (B) hydroxyl apatite.

The 150 ml material obtained from G-25 column was applied on DEAE 650-M column (5.2×10.6, 225 ml) pre-equilibrated with 50 mM HEPES, pH 7.5. The enzyme was eluted at 0.2 M NaCl by running a linear gradient of 0-0.5 M NaCl in 15 column volumes of the buffer at 300 ml/h (FIG. 15A). The fractions containing the enzyme activity were combined (235 ml) and were diluted to twice the volume (480 ml) with Milli-Q water to lower the salt concentration.

The diluted solution was applied to a Bio-gel HTP column (2.6×11.3, 60 ml) at 120 ml/h, which was pre-equilibrated with 10 mM potassium phosphate buffer, pH 6.8 and 100 mM NaCl. The bound proteins were eluted with a linear gradient of 10 mM to 100 mM phosphate concentration and 100 to 0 mM NaCl concentration in 15 column volumes. The active fractions were collected (76 ml) and fractions 29, 31, 33, 34, 35, 36, 37 were analyzed for purity on 12.5% SDS-PAGE. There were few impurities left (FIG. 15B), so fractions 29-37 were pooled, precipitated with 80% ammonium sulfate, and taken up in 50 mM HEPES buffer pH 7.5 for gel filtration chromatography on Sephacryl-200 column (247 ml) at 10 ml/h in 50 mM HEPES, pH 7.5 and 150 mM NaCl. (Table 10) Fractions 49-54 were analyzed on SDS-PAGE before pooling. The pooled enzyme was concentrated in 10 kD membrane filters (Sigma) and stored in 50% glycerol at −70° C. in 30 μL aliquots for the detailed characterization studies.

Amidase activity was found to be soluble in the cytoplasmic fraction on sonication of the cells and the level of activity was found to be ~400-fold greater than in $M.$ smegmatis mc$^2$155 (Sareen, et al., 2002, supra.) the parent strain of mutant I64. The recombinant protein eluted as a single peak with apparent $M_r$=34 kD on the S-200 column (actual Mr 45,591). Thus, the $M.$ tuberculosis MshC protein exists as a monomer in its native form. This contrasts with its ortholog from $M.$ smegmatis, which forms dimers and tetramers in the native state (Sareen, et al., 2002, supra.).

TABLE 10

Purification of $M.$ tuberculosis Cys:GlcN-Ins ligase (MshC)

| Step | protein[a] (mg) | total activity (nmol min$^{-1}$) | specific activity (nmol min$^{-1}$ mg$^{-1}$) | yield (%) | Purif. factor |
|---|---|---|---|---|---|
| Crude extract | 1670 | 14600 | 8.7 | (100) | (1) |
| 20-45% SAS | 540 | 14000 | 26.0 | 96.0 | 3.0 |
| DEAE ion exchange | 94 | 2590 | 27.5 | 17.7 | 3.7 |
| Hydroxyl apatite | 10 | 1076 | 108 | 7.4 | 12.4 |
| S-200 gel filtration | 0.6 | 93 | 155 | 0.64 | 17.8 |

[a]Protein concentration based upon $A_{280}$ value, where 1 AU = 0.58 mg/ml for purified MshC.

Metal Analysis

The purified enzyme was analyzed by Inductively coupled plasma-atomic emission spectroscopy (ICP) at the San Diego Gas & Electric Environmental Analysis laboratory for 26 metal ions; Al, Sb, As, Ba, Be, B, Cd, Ca, Cr, Co, Cu, Fe, Pb, Mg, Mn, Mo, Ni, K, Se, Si, Na, Sr, Th, Ti, V and Zn. The enzyme sample was diluted to 1 mg/ml and buffer was also submitted for background metal analysis.

Figure 16:
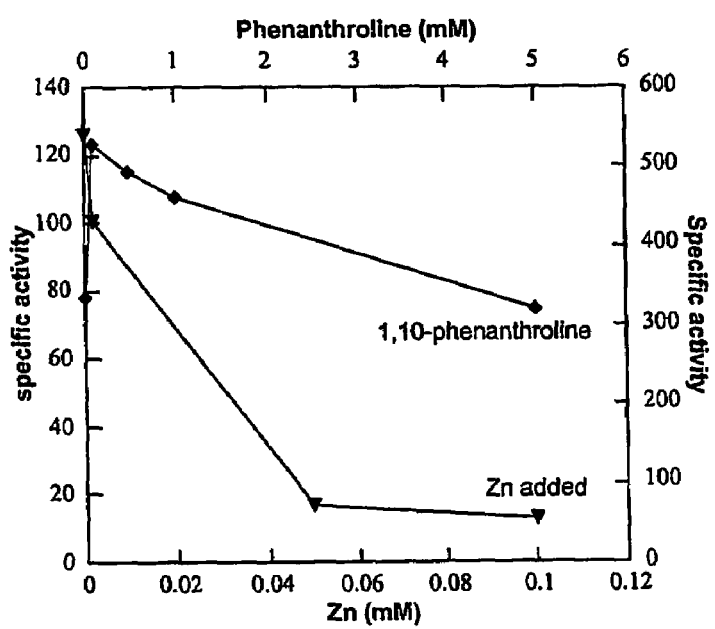
FIG. 16 is a graph showing the effect of 1,10-phenanthroline and $Zn^{2+}$ on the activity of MshC.
Figure 17:
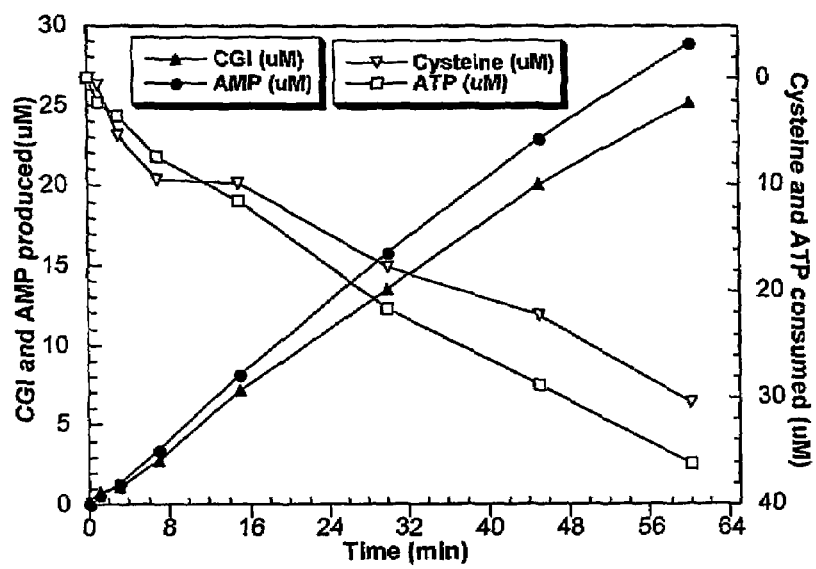
FIG. 17 is a graph showing the stoichiometry of MshC ligase reaction.

The ICP showed that there is 0.7 mol of Zinc ion/mol of enzyme. Attempts to inactivate the enzyme by chelating the metal present with 1,10-phenanthroline produced no significant loss of activity (FIG. 16) and supplementation of the enzyme with $Zn^{2+}$ led to a loss in activity (FIG. 16). Thus, if $Zn^{2+}$ is required for activity, it must be quite tightly bound and not easily removed or complexed by 1,10-phenanthroline. In addition there must be residues capable of binding $Zn^{2+}$ in a fashion which distorts or blocks the active site in a fashion which interferes with enzyme activity.

Testing of MshC for Cys-tRNA Ligase Activity

The initial reaction of cysteinyl-tRNA synthetase and MshC is the formation of enzyme bound AMP-cys. Since $E.$ coli cys-tRNA synthetase and $M.$ tuberculosis MshC (cysS2) are homologs, they have been used to focus on the second reaction, the tRNA charging reaction of cys-tRNA synthetase and MshC. It was found that the reactions were complete in 1 min at room temperature and gave stable filter counts after that time. The rates for the formation of tRNA$^{cys}$ were 11±2.5 (n=5) and 0±0.2 (n=4) nmole/min/mg protein for $E.$ coli cys-tRNA synthetase and $M.$ tuberculosis MshC, respectively. Thus $M.$ tuberculosis MshC, annotated as cysS2 or cysteinyl-tRNA synthetase 2, will not charge $E.$ coli tRNAs in this assay. The foregoing shows that the activity of MshC is the ATP dependent formation of Cys-GlcN-Ins, an intermediate in the mycothiol biosynthesis pathway, and not the synthesis of tRNA$^{cys}$.

Stoichiometry of the Reaction Catalyzed by MshC

Purified MshC was utilized to establish the stoichiometry of the reaction catalyzed. It had been initially assumed that the ATP-dependent production of Cys-GlcN-Ins yielded ADP as a coproduct by analogy with the enzymology of γ-glutamylcysteine biosynthesis, the intermediate precursor of glutathione (Newton, et al. (2000) $J.$ Bacteriol. 182, 6958-6963; Bornemann, et al. (1997) Biochem. $J.$ 325, 623-9.). However, when MshC was identified as a homolog of cysteinyl-tRNA synthetase (CysS), where the overall reaction produces AMP plus pyrophosphate, it appeared likely that the product of the MshC catalyzed reaction was also AMP. To verify this the levels of Cys, ATP, AMP and Cys-GlcN-Ins were monitored over 60 min in a reaction initiated with 100 μM Cys, 100 μM GlcN-Ins, and 200 μM ATP. The results (FIG. 15) show that AMP is indeed the product derived from ATP. After 60 min the reaction was 30% complete and for each equivalent of Cys utilized 0.82 equivalents of Cys-GlcN-Ins was produced, accompanied by the utilization of 1.19 equivalents of ATP and the production of 0.95 equivalents of AMP. This establishes the reaction stoichiometry as indicated in FIG. 1.

Enzyme Kinetics and Substrate Specificity

The factors influencing the enzymatic assay of MshC activity at 37° C. were explored in 50 mM HEPES buffer, pH 7.5 containing 1 mM DTT. With 100 μM GlcN-Ins, 0.5 mM Cys, and 0.5 mM ATP as substrates, the reaction rate increased sharply with $Mg^{2+}$ concentration up to 100 μM, then leveled and became constant from 1-5 mM $Mg^{2+}$. Under the same conditions but with 5 mM $Mg^{2+}$ and varying the ATP concentration, the rate increased up to 100 μM ATP, remained constant to 1 mM ATP, and then declined 2.2-fold at 5 mM ATP. Based upon these results 1 mM each of $Mg^{2+}$ and ATP were selected as standard assay concentrations. The apparent $K_m$ values were estimated from Eadie-Hofstee plots, which were linear over the indicated range of concentration. With 1 mM each of ATP and GlcN-Ins, the apparent $K_m$ for L-Cys (5 μM to 1.6 mM, n=10) was determined to be 85±20 μM and the apparent $V_{max}$ was 1450±200 nmol min$^{-1}$ mg$^{-1}$. For 1 mM ATP and 0.5 mM Cys, the apparent $K_m$ for GlcN-Ins (10 μM to 3 mM, n=6) was determined to be 280±43 μM and the apparent $V_{max}$ was 1160±120 nmol min$^{-1}$ mg$^{-1}$. The apparent $K_m$ for GlcN-Ins of 280±43 μM is about 4-fold higher than the value reported for the enzyme purified from $M.$ smegmatis.

Several thiols related to cysteine were tested as alternative substrates to Cys, each examined at concentrations ranging from 80 μM to 1.6 mM. The results obtained at the highest concentration are given in Table 11. The enantiomer, D-Cys, was a poor substrate. Neither β-mercaptopropionic acid nor cysteamine, derived from Cys by removal of the amino and carboxyl groups, respectively, produced evidence of reaction. Nor was significant activity detected with AcCys, L-homocysteine, L-serine, or L-alanine. Thus, the enzyme is highly specific for Cys. The specificity is less stringent for GlcN-Ins, with GlcN having ~1% the activity of GlcN-Ins increasing linearly over the range of concentration studied.

Inhibition of MshC

Various compounds were tested over the concentration range 80-1600 μM as inhibitors of the ligase activity measured with 70 μM L-Cys and 50 μM GlcN-Ins. Results for the highest level tested are shown in Table 11. Only very minor inhibition was produced by the amino acids D-Cys, L-homocysteine, L-α-aminobutyric acid, L-serine, and L-alanine. β-mercaptopropionic acid (deaminated Cys) and N-acetyl-cysteine also produced minor inhibition. Of all compounds tested the best inhibitor was cysteamine (decarboxylated Cys) which produced a 3-fold reduction in rate at 1.6 mM. Mycothiol also produced minimal inhibition at concentrations of 1 and 5 mM, representing physiologic levels.

TABLE 11

Substrate specificity and inhibition of MshC

| compound | relative spec. act.[a] | inhibition [inhibitor] (μM) | % inhibition[b] |
|---|---|---|---|
| Cys (70 μM) | (100)[c] | — | — |
| D-Cys | ≤0.7 | 1600 | 15 ± 8 |
| β-mercaptopropionate | ≤0.004 | 1600 | −20 ± 20 |
| cysteamine | ≤0.16 | 1600 | 65 ± 10 |
| AcCys | ≤0.24 | 1600 | 20 ± 6 |
| L-homocysteine | ≤0.2 | 1600 | 0 ± 5 |
| L-serine | ≤0.008 | 5000 | 15 ± 8 |
| L-alanine | ≤0.016 | 5000 | 4 ± 8 |
| D-GlcN (1.6 mM)[d] | 1.2 | — | — |
| MSH | — | 1000 | 4 ± 3 |
| MSH | — | 5000 | 7 ± 5 |

[a]Ligase activity determined at 37° C. with 50 μM GlcN-Ins and 1.6 mM test substrate, unless otherwise noted. Relative specific activity calculated from maximal peak intensity at highest test concentration and assuming linear dependence upon concentration.
[b]Inhibition determined with 50 μM GlcN-Ins and 70 μM Cys under standard assay conditions.
[c]Specific activity 108 nmol min$^{-1}$ mg$^{-1}$.
[d]In place of GlcN-Ins with 100 μM Cys.

The MshC ligase was also tested for feedback inhibition by Cys-GlcN-Ins. The intracellular level of Cys-GlcN-Ins was found to be 5-10 μM in *M. tuberculosis*, when analyzed at different growth time points (Buchmeier, Newton, Koledin and Fahey, unpublished). So, it was logical to analyze Cys-GlcN-Ins in the concentration range of 1-10 μM with levels of the Cys and GlcN-Ins substrates near their $K_m$ values, 70 and 300 μM, respectively. The apparent $K_m$ value for Cys of 70±15 μM found here is nearly double the value found earlier for the *M. smegmatis* enzyme. Cys-GlcN-Ins produced <1.0 and 3.6% inhibition when tested at 0.7 μM and 6.6 μM, respectively, which shows that there is no significant feedback inhibition at physiological levels of the reaction product.

EXAMPLE 13

Essentiality of Mycothiol in *M. tuberculosis*

The use of conditional null mutants to establish essentiality in *M. tuberculosis* has not yet been accomplished so the present example employed the general approach used by Parish and Stoker (Parish, et al. (2000), J. Bacteriol. 182: 5715-20) to test the essentiality of the glnE. A second copy of the mshC gene was introduced into wild type *M. tuberculosis* using an integrative vector pCV125 (kindly provided by Med-immune) which was modified to contain the spectinomycin/streptomycin (Sp/Sm) cassette from pKRP13. This vector containing the mshC gene has been constructed and tested on *M. smegmatis* strain I64, a chemical mutant defective in mshC and MSH production (Rawat, 2002, supra.). It was shown to be effective in restoring MSH production in *M. smegmatis* I64. pCV125 integrates into the att site in the *M. tuberculosis* chromosome and will stably introduce a second copy of the mshC gene into a second location of the chromosome. The mshC ORF plus its ribosomal binding site (71 bp upstream of the ATG start codon) was amplified by PCR using genomic *M. tuberculosis* (Erdman) DNA. The forward primer 5'-TC-CCCCGGGACGCGTGGCGCTGAT-3' (SEQ ID NO: 45), contains a SmaI restriction site, and the reverse primer 5'-GGACTAGTCTACAGGTCCACCCCGAGCAG-3' (SEQ ID NO: 46), contains a SpeI restriction site which was used for directional cloning. The PCR fragment was ligated with pCR 2.1 (Invitrogen) using T4 DNA ligase and used to transform TOP 10F' (Invitrogen) *E. coli*. After selection on agar plates (LB, ampicillin 100 μg/ml) and growth in broth, plasmid DNA was analyzed by restriction analysis and sequencing. The SmaI/SpeI fragment containing the mshC gene from this plasmid was cloned between the SmaI and SpeI sites within the aph gene in pCV125. This resulted in a vector containing a copy of the mshC gene that is transcribed from the aph promoter. Vector DNA was introduced into wild type *M. tuberculosis* by electroporation with selection on 7H11 plates containing streptomycin. As a control, pCV125 with no extra DNA was introduced into other aliquots of *M. tuberculosis*. Streptomycin resistant colonies were grown up, chromosomal DNA was extracted, and the presence of 2 copies of the mshC gene were confirmed by Southern hybridization. NcoI digests were initially used because this enzyme cuts outside of the mshC gene and will allow for easy identification of differences in flanking sequences between the native copy of mshC and the introduced copy. SacI digests were also used to analyze the original and the introduced copies of mshC within the genomic DNA of transformants.

After the presence of the second copy of the mshC gene was confirmed using Southern hybridization, 2×-mshC was infected with the specialized transducing phage containing the mshC knockout construct. The specialized transducing phage is a variant of a mycobacteriophage described by Bardarov et al. (Bardarov, et al. (2002), supra; Bardarov, et al. (1997) *Proc. Natl. Acad. Sci.* 94:10961-6.) and was a gift from J. Cox. The specialized transducing phage containing the mshC knockout DNA was constructed by amplifying ~500 bp of the upstream fragment (protein N-terminal region of mshC) comprising 102 bp of the mshC gene and 370 bp of downstream sequence, and ~500 bp of a middle fragment (residues 195-708) of the mshC gene. This results in a deletion of the residues encoding the active site "HGLH" (SEQ ID NO: 47) region of the protein. Each primer set incorporated suitable endonuclease sites to allow subcloning of the PCR product into plasmid pJSC284 such that a hygromycin resistance cassette was inserted within the mshC ORF. After verifying the fragment incorporation, the plasmid was digested with PacI, treated with alkaline phosphatase to prevent plasmid rejoining during subsequent ligation and ligated into the PacI site of the specialized transducing phage phAE87. DNA was packaged into λ phage using Gigapack III Gold packaging extract (Stratagene) and this was used to infect HB101 *E. coli* grown on maltose to promote phage uptake. Colonies were selected on hygromycin. Cosmid DNA was extracted from the hyg$^r$ colonies and was used to transform *M. smegmatis* mc$^2$155. The transformation plates were incubated at 30° C. until plaques appeared (2-3 days). Plaques were picked and a high titer phage stock was prepared from *M. smegmatis* mc$^2$155.

For infection of *M. tuberculosis*, 10 ml of bacteria was washed with MP buffer and resuspended in 1 ml MP buffer at 39° C. (Buchmeier et al. (2000) *Molec. Microbiol.* 35:1375-1382.). Phage was added at a multiplicity of infection of 10 and the mixture was incubated at 39° C. for 4 hr to allow for phage infection. The bacteria were spun down, resuspended in 500 ml MP buffer and plated on 7H11 plates containing hygromycin (50 mg/ml). Hygromycin resistant colonies appeared in 3 to 5 weeks. Individual colonies were grown up for analysis by Southern hybridization (to verify the presence of the mshC knockout) and for measurement of MSH content. The allelic exchange substrate should recombine preferentially with the native copy of the mshC gene and not with the introduced copy since the flanking sequences of the introduced mshC gene differ from the flanking sequences of mshC in the phage mutagenesis construct. The corA knockout phage construct was included as a positive control for the transduction procedures.

In initial experiments with *M. tuberculosis* with only the original copy of mshC, the phAEΔmshC phasmid produced hygromycin resistant transformants that contained parental mycothiol levels. This experiment was repeated several times with a total of 67 hygromycin clones analyzed by Southern blot. All clones were found to have the original copy of mshC intact. Representative clones such as clone 49 (Table 12) were examined for mycothiol content and found to have the parental levels of mycothiol. Thus, no authentic mshC mutants were detected in the 67 clones examined from transformation of the parental strain of *M. tuberculosis* Erdman.

Initially the integrative plasmid delivering the second copy of mshC was tested on a chemical mutant of mshC in *M. smegmatis* (strain I64) which produces about 1% of the parental level of mycothiol (Rawat, et al., 2002, supra.). Incorporation of the *M. tuberculosis* mshC gene resulted in the production of 150% of the parental level of mycothiol in this mycothiol mutant (results not shown). This same plasmid was used to transform *M. tuberculosis* Erdman to make the merodiploid host 2×mshc identified as strain 1682 in a Southern blot. There is a single SacI site in mshC which generates 2 bands in the original copy observed in the *M. tuberculosis* Erdman (Erd) strain as well as in the second copy as observed in 1682, the 2×mshC host strain in another Southern blot. The mycothiol content 2×mshC strain is nearly twice the parental level (Table 12). One of the substrates of MshC, GlcN-Ins, is reduced by 64% by the presence of the second copy of mshC in the 2×mshC strain 1682 (Table 12). This is consistent with ligase substrate depletion due to a higher level of cellular MshC activity. The Southern blots taken together with the mycothiol analyses verify the presence of a functional second copy of mshC in the 2×mshC host strain.

TABLE 12

Mycothiol and precursor levels in *M. tuberculosis* Erdman mshC knockout strains[a].

| Host and Control strains | $OD_{600}$ | GlcNAc-Ins | GlcN-Ins | MSH |
|---|---|---|---|---|
| | | nmoles/$10^9$ Cells | | |
| *M. tuberculosis* Erdman (parent) | 0.50 | 1.7 ± 0.7 | 8.9 ± 0.2 | 13.7 ± 0.2 |
| Strain 3 | 0.41 | ≦0.7 | 7.3 ± 0.1 | 12.1 ± 1.3 |
| 1682 Erdman (+2 nd copy MshC) | 0.85 | 0.9 ± 0.1 | 3.2 ± 0.1 | 26.2 ± 1.2 |
| Strain 49 | 0.47 | 1.7 ± 0 | 9.2 ± 0.1 | 21.5 ± 0.5 |
| mshC knockout strains in (2x mshC) *M. tuberculosis* Erdman 1682 | | | | |
| Strain 14 | 0.36 | ≦1.4 | 14.1 ± 0.2 | 12 ± 0.3 |
| Strain 16 | 0.37 | ≦0.6 | 5.7 ± 0.3 | 14.6 ± 0.1 |
| Strain 18 | 0.43 | ≦1.2 | 12 ± 1 | 10.2 ± 0.1 |
| Strain 157 | 0.58 | 1.5 ± 0.7 | 12 ± 1.4 | 10.2 ± 0.1 |
| Strain 158 | 0.52 | 1.7 ± 0.4 | 15 ± 1 | 11.8 ± 0.1 |
| Strain 172 | 0.49 | 1.0 ± 0.5 | 8.5 ± 0.2 | 11.3 ± 0.2 |

[a]Results expressed as mean and range of duplicate samples.

This organism served as a primary host for the attempted mshC knockout experiments. Using this host 6 of 12 or 50% of the hygromycin resistant transformants were found to be authentic knockouts in the original copy of mshC (Table 13). Strains identified as 14, 16, 18, 157, 158, and 172 all lack the original copy of mshC, as was seen in a Southern blot, but do contain the second copy of the gene. These strains also make parental levels of mycothiol and its precursor GlcN-Ins (Table 12), demonstrating the second mshC gene if fully functional. In one case, strain 3, it appears that the second copy and not the original copy of mshC was interrupted by the knockout phasmid. As a positive control for the transformation efficiency, a transformation of *M. tuberculosis* Erdman (without a second corA copy) with a phasmid carrying a knockout construct for the non-essential magnesium transporter corA was successful in knocking out corA in 6 of 18 or 33% of the transformants (results not shown). An empty plasmid pCV125 control strain of *M. tuberculosis* host Erdman was transformed with the mshC knockout phasmid (phAEΔmshC) and 0 out of 7 of the transformants were authentic mshC knockouts by Southern blot (results not shown). Thus, no transformants can be found without mycothiol in any of the above experiments. Additionally no authentic mshC knockout strains can be found by Southern analysis, except when a second copy of mshC is supplied. These results clearly support that mshC specifically, and mycothiol generally, are essential for the survival of *M. tuberculosis* in laboratory culture. These experiments demonstrate the essentiality of mycothiol and validate the mycothiol biosynthesis genes as possible drug targets.

TABLE 13

*M. tuberculosis* Erdman directed knockouts in mycothiol biosynthesis gene mshC (Rv 2130c).

| | Knockouts by Southern blot | Transformants Examined[a] | Knockout Efficiency |
|---|---|---|---|
| *M. tuberculosis* Erdman + empty vector (for 2x mshC) (negative control) | 0 | 7 | 0% |
| *M. tuberculosis* Erdman + phasmid phAEΔcorA (positive control) | 6 | 18 | 33% |
| *M. tuberculosis* Erdman + phasmid phAEΔmshC | 0 | 67 | 0% |
| *M. tuberculosis* Erdman 2x mshC (strain 1682) + phasmid phAEΔmshC | 6 | 12 | 50% |

[a]Transformants are hygromycin resistant colonies appearing within 5 weeks.

Although the invention has been described with reference to the above examples, it will be understood that modifications and variations are encompassed within the spirit and scope of the invention. Accordingly, the invention is limited only by the following claims.

What is claimed is:

1. A method for identifying an inhibitor of cysteine:glucosaminyl inositol ligase comprising:
   a) contacting a candidate compound with a cysteine:glucosaminyl inositol ligase in the presence of a cysteine and a glucosaminyl inositol, under suitable conditions, and
   b) determining the presence or absence of ligation of the cysteine to the glucosaminyl inositol,
   wherein the cysteine:glucosaminyl inositol ligase is characterized as having:
      i) an amino acid sequence with 54% or more sequence identity to SEQ ID NO: 2 or 4, and
      ii) cysteine:glucosaminyl inositol ligase activity, and
   wherein the substantial absence of the ligation is indicative of a candidate compound that inhibits activity of the ligase.

2. The method of claim 1, wherein the cysteine is L-cysteine.

3. The method of claim 1, wherein the glucosaminyl inositol comprises D-glucosamine.

4. The method of claim 1, wherein the glucosaminyl inositol is derivatized with monobromobimane (mBBr).

5. The method of claim 1, wherein the conditions comprise the presence of ATP.

6. The method of claim 5, wherein the glucosaminyl inositol is 1D-myo-inosityl 2-amino-2-deoxy-α-D-glucopyranoside.

7. The method of claim 1, wherein the ligase is produced in an actinomycete.

8. The method of claim 1, wherein the candidate compound is a polypeptide, polynucleotide or small molecule.

* * * * *